United States Patent [19]
Glücksmann

[11] Patent Number: 6,037,173
[45] Date of Patent: Mar. 14, 2000

[54] ISOLATED NUCLEIC ACID ENCODING TRBP

[75] Inventor: M. Alexandra Glücksmann, Somerville, Mass.

[73] Assignee: Millennium Pharmaceuticals, Inc., Cambridge, Mass.

[21] Appl. No.: 08/840,146

[22] Filed: Apr. 11, 1997

[51] Int. Cl.$^7$ ............................ C12N 15/85; C12N 15/63; C07H 21/04
[52] U.S. Cl. ........................ 435/325; 435/320.1; 435/366; 536/23.1; 536/23.5; 536/24.31
[58] Field of Search ............................. 435/6, 320.1, 325, 435/366; 536/23.1, 23.5, 24.31

[56] References Cited

U.S. PATENT DOCUMENTS 5,602,009  2/1997  Evans et al. ........................... 435/69.7

FOREIGN PATENT DOCUMENTS

WO 94/10338  5/1994  WIPO .
WO 96 21728  7/1996  WIPO .

OTHER PUBLICATIONS

Yamagata, K. et al., "Mutation in the Hepatocyte nuclear factor 4–alpha gene in maturity–onset diabetes of the young MODY1," *Nature*, vol. 384, pp. 458–460, Dec. 5, 1996.
Berendsen, A glimpse of the holy grail, *Science*, vol. 282., pp. 642–643, Oct. 1998.
White, Genbank, Accession #Z93097, Mar. 20, 1997.
Woon Lee et. al., Interaction of Thyroid–Hormone Receptor with a Conserved Transcriptional Mediator, *Nature,* vol. 374, pp. 91–94 (Mar. 1995).
Woon Lee et. al., "Two Classes of Proteins Dependent on Either the Presence or Absence of Thyroid Hormone for Interaction with the Thyroid Hormone Receptor", *Molecular Endocrinolgy,* vol. 9, No. 2, pp. 244–254 (1995); and.
Zhang et. al., "Ligant–dependent Cross–talk between Steroid and Thryoid Hormone Receptors", *The Journal of Biological Chemistry,* vol. 271, No. 25, pp. 14825–14838 (Jun. 21, 1996).

*Primary Examiner*—Nancy Degen
*Assistant Examiner*—Andrew Wang
*Attorney, Agent, or Firm*—Foley, Hoag & Eliot LLP; Beth E. Arnold, Esq.; Isabelle M. Clauss

[57] ABSTRACT

The invention provides nucleic acids encoding a TRBP polypeptide, fragments thereof and homologs thereof The invention also provides TRBP polypeptides, fragments thereof and homologs thereof, and TRBP binding proteins. Methods for treating diseases or conditions characterized by an aberrant TRBP activity, e.g., by administering to the subject a TRBP therapeutic, are also disclosed. Diseases or conditions that can be treated according to the methods of the invention include thyroid-related disorders, metabolic disorders, and diabetes. Also disclosed are methods for predicting whether a subject is at risk of developing a disease associated with an aberrant TRBP activity, by determining, e.g., whether the subject has a genetic lesion in a TRBP gene and assays for identifying TRBP therapeutics.

16 Claims, 9 Drawing Sheets

Input file fih353; Output File fih353tr
Sequence length 2241

CGCCATTGGTTCTCTAGATGCATGCCCGAGCGGCCGCCAGTGTGCTCTAAAGGCCTCAATTTCCTTAGACAGATGTAAG

CAGTTGAATTGACTAACAACTATCCAACCCCAACCTACTGGGCAAGTTGCCTCCTTTGGGGTCAAACACTATCCAACTT

CAGTTTCCCAACGTCATAAAGGAGAACTCTAAAAGTTGAGAATCGAAACTGATGACAGACTGACTAGACGGCCAGCCTG

TTAAGGTGGCCCCAGATATTCCAGCCTCAGCCCAGAGTCCTCCTGTGCCCCTACTGCAGCAAGGGTGTCTCCAAGAAGG

GGGACCTGGAGTCAGCCCGTCACACCTGGTTTCCTCTCTGCTANGGTCCCTCCTCCCACAGAGCACTGGAGGGCAGCTG

AAGAAGAGCTACCTTAAAAAAGGAAGTGTGTGCCAGGGAACTGGGTAGGAACCTGGCTATATATCTGCCCAGCAGCGGT

```
                   M   A   L   M   Q   E   L   Y   S   T   P   A   S   R   L   D   16
ACTCTCGGGACAGAG   ATG GCA CTG ATG CAG GAA CTG TAT AGC ACA CCA GCC TCC AGG CTG GAC   48

S   F   V   A   Q   W   L   Q   P   H   R   E   W   K   E   E   V   L   D   A   36
TCC TTC GTG GCT CAG TGG CTG CAG CCC CAC CGG GAG TGG AAG GAA GAA GTG CTA GAC GCT   108

V   R   T   V   E   E   F   L   R   Q   E   H   F   Q   G   K   R   G   L   D   56
GTG CGG ACC GTG GAA GAA TTT CTG AGG CAG GAG CAT TTC CAG GGG AAG CGT GGG CTG GAC   168

Q   D   V   R   V   L   K   V   V   K   V   G   S   F   G   N   G   T   V   L   76
CAG GAT GTG CGG GTG CTG AAG GTA GTC AAG GTG GGC TCC TTC GGG AAT GGC ACG GTT CTC   228

R   S   T   R   E   V   E   L   V   A   F   L   S   C   F   H   S   F   Q   E   96
AGG AGC ACC AGA GAG GTG GAG CTG GTG GCG TTT CTG AGC TGT TTC CAC AGC TTC CAG GAG   288

A   A   K   H   H   K   D   V   L   R   L   I   W   K   T   M   W   Q   S   Q   116
GCA GCC AAG CAT CAC AAA GAT GTT CTG AGG CTG ATA TGG AAA ACC ATG TGG CAA AGC CAG   348

D   L   L   D   L   G   L   E   D   L   R   M   E   Q   R   V   P   D   A   L   136
GAC CTG CTG GAC CTC GGG CTC GAG GAC CTG AGG ATG GAG CAG AGA GTC CCC GAT GCT CTT   408

V   F   T   I   Q   T   R   G   T   A   E   P   I   T   V   T   I   V   P   A   156
GTC TTC ACC ATC CAG ACC AGG GGG ACT GCG GAG CCC ATC ACG GTC ACC ATT GTG CCT GCC   468

Y   R   A   L   G   P   S   L   P   N   S   Q   P   P   P   E   V   Y   V   S   176
TAC AGA GCC CTG GGG CCT TCT CTT CCC AAC TCC CAG CCA CCC CCT GAG GTC TAT GTG AGC   528

L   I   K   A   C   G   G   P   G   N   F   C   P   S   F   S   E   L   Q   R   196
CTG ATC AAG GCC TGC GGT GGT CCT GGA AAT TTC TGC CCA TCC TTC AGC GAG CTG CAG AGA   588

N   F   V   K   H   R   P   T   K   L   K   S   L   L   R   L   V   K   H   W   216
AAT TTC GTG AAA CAT CGG CCA ACT AAG CTG AAG AGC CTC CTG CGC CTG GTG AAA CAC TGG   648

Y   Q   Q   Y   V   K   A   R   S   P   R   A   N   L   P   P   L   Y   A   L   236
TAC CAG CAG TAT GTG AAA GCC AGG TCC CCC AGA GCC AAT CTG CCC CCT CTC TAT GCT CTT   708
```

Fig. 1A

```
      E   L   L   T   I   Y   A   W   E   M   G   T   E   E   D   E   N   F   M   L   256
     GAA CTT CTA ACC ATC TAT GCC TGG GAA ATG GGT ACT GAA GAA GAC GAG AAT TTC ATG TTG  768

D   E   G   F   T   T   V   M   D   L   L   L   E   Y   E   V   I   C   I   Y   276
     GAC GAA GGC TTC ACC ACT GTG ATG GAC CTG CTC CTG GAG TAT GAA GTC ATC TGT ATC TAC  828

W   T   K   Y   Y   T   L   H   N   A   I   I   E   D   C   V   R   K   Q   L   296
     TGG ACC AAG TAC TAC ACA CTC CAC AAT GCA ATC ATT GAG GAT TGT GTC AGA AAA CAG CTC  888

K   K   E   R   P   I   I   L   D   P   A   D   P   T   L   N   V   A   E   G   316
     AAA AAA GAG AGG CCC ATC ATC CTG GAT CCG GCC GAC CCC ACC CTC AAC GTG GCA GAA GGG  948

Y   R   W   D   I   V   A   Q   R   A   S   Q   C   L   K   Q   D   C   C   Y   336
     TAC AGA TGG GAC ATC GTT GCT CAG AGG GCC TCC CAG TGC CTG AAA CAG GAC TGT TGC TAT 1008

D   N   R   E   N   P   I   S   S   W   N   V   K   R   A   R   D   I   H   L   356
     GAC AAC AGG GAG AAC CCC ATC TCC AGC TGG AAC GTG AAG AGG GCA CGA GAC ATC CAC TTG 1068

T   V   E   Q   R   G   Y   P   D   F   N   L   I   V   N   P   Y   E   P   I   376
     ACA GTG GAG CAG AGG GGT TAC CCA GAT TTC AAC CTC ATC GTG AAC CCT TAT GAG CCC ATA 1128

R   K   V   K   E   K   I   R   R   T   R   G   Y   S   G   L   Q   R   L   S   396
     AGG AAG GTT AAA GAG AAA ATC CGG AGG ACC AGG GGC TAC TCT GGC CTG CAG CGT CTG TCC 1188

F   Q   V   P   G   S   E   R   Q   L   L   S   S   R   C   S   L   A   K   Y   416
     TTC CAG GTT CCT GGC AGT GAG AGG CAG CTT CTC AGC AGC AGG TGC TCC TTA GCC AAA TAT 1248

G   I   F   S   H   T   H   I   Y   L   L   E   T   I   P   S   E   I   Q   V   436
     GGG ATC TTC TCC CAC ACT CAC ATC TAT CTG CTG GAG ACC ATC CCC TCC GAG ATC CAG GTC 1308

F   V   K   N   P   D   G   G   S   Y   A   Y   A   I   N   P   N   S   F   I   456
     TTC GTG AAG AAT CCT GAT GGT GGG AGC TAC GCC TAT GCC ATC AAC CCC AAC AGC TTC ATC 1368

L   G   L   K   Q   Q   I   E   D   Q   Q   G   L   P   K   K   Q   Q   Q   L   476
     CTG GGT CTG AAG CAG CAG ATT GAA GAC CAG CAG GGG CTT CCT AAA AAG CAG CAG CAG CTG 1428

E   F   Q   G   Q   V   L   Q   D   W   L   G   L   G   I   Y   G   I   Q   D   496
     GAA TTC CAA GGC CAA GTC CTG CAG GAC TGG TTG GGT CTG GGG ATC TAT GGC ATC CAA GAC 1488

S   D   T   L   I   L   S   K   K   K   G   E   A   L   F   P   A   S   *       515
     AGT GAC ACT CTC ATC CTC TCG AAG AAG AAA GGA GAG GCT CTG TTT CCA GCC AGT TAG     1545

TTTTCTCTGGGAGACTTCTCTGTACATTTCTGCCATGTACTCCAGAACTCATCCTGTCAATCACTCTGTCCCATTGTCT

ACTGGGAAGGTCCCAGGTCTTCACCAGTTTTACAATGAGTTATCCCAGGCCAGACGTGGTAGCTCACACCTGTAATCCC

AGAACTTTGGGAAGCCCAAGTGGGAGGAACGCTTGAACCCAGGATTCAA
```

Fig. 1B

CLUSTAL W(1.4) multiple sequence alignment

```
gi|7031031|  ----------------------------------------------------------
Contig1_2    GCCATTGGTTCTCTAGATGCATGCCCGAGCGGCCGCCAGTGTGCTCTAAAGGCCTCAATT gi|7031031|  ----------------------------------------------------------
Contig1_2    TCCTTAGACAGATGTAAGCAGTTGAATTGACTAACAACTATCCAACCCCAACCTACTGGG gi|7031031|  ----------------------------------------------------------
Contig1_2    CAAGTTGCCTCCTTTGGGGTCAAACACTATCCAACTTCAGTTTCCCAACGTCATAAAGGA gi|7031031|  ----------------------------------------------------------
Contig1_2    GAACTCTAAAAGTTGAGAATCGAAACTGATGACAGACTGACTAGACGGCCAGCCTGTTAA gi|7031031|  ----------------------------------------------------------
Contig1_2    GGTGGCCCCAGATATTCCAGCCTCAGCCCAGAGTCCTCCTGTGCCCCTACTGCAGCAAGG gi|7031031|  ----------------------------------------------------------
Contig1_2    GTGTCTCCAAGAAGGGGGACCTGGAGTCAGCCCGTCACACCTGGTTTCCTCTCTGCTANG gi|7031031|  ----------------------------------------------------------
Contig1_2    GTCCCTCCTCCCACAGAGCACTGGAGGGCAGCTGAAGAAGAGCTACCTTAAAAAAGGAAG gi|7031031|  ----------------------------------------------------------
Contig1_2    TGTGTGCCAGGGAACTGGGTAGGAACCTGGCTATATATCTGCCCAGCAGCGGTACTCTCG gi|7031031|  ----------------------------------------------------------
Contig1_2    GGACAGAGATGGCACTGATGCAGGAACTGTATAGCACACCAGCCTCCAGGCTGGACTCCT gi|7031031|  ----------------------------------------------------------
Contig1_2    TCGTGGCTCAGTGGCTGCAGCCCCACCGGGAGTGGAAGGAAGAAGTGCTAGACGCTGTGC gi|7031031|  ----------------------------------------------------------
Contig1_2    GGACCGTGGAAGAATTTCTGAGGCAGGAGCATTTCCAGGGGAAGCGTGGGCTGGACCAGG gi|7031031|  ----------------------------------------------------------
Contig1_2    ATGTGCGGGTGCTGAAGGTAGTCAAGGTGGGCTCCTTCGGGAATGGCACGGTTCTCAGGA gi|7031031|  ----------------------------------------------------------
Contig1_2    GCACCAGAGAGGTGGAGCTGGTGGCGTTTCTGAGCTGTTTCCACAGCTTCCAGGAGGCAG gi|7031031|  ----------------------------------------------------------
Contig1_2    CCAAGCATCACAAAGATGTTCTGAGGCTGATATGGAAAACCATGTGGCAAAGCCAGGACC
```

Fig. 2A

```
gi|703103|     ------------------------------------------------------------
Contig1_2      TGCTGGACCTCGGGCTCGAGGACCTGAGGATGGAGCAGAGAGTCCCCGATGCTCTTGTCT gi|703103|     ------------------------------------------------------------
Contig1_2      TCACCATCCAGACCAGGGGGACTGCGGAGCCCATCACGGTCACCATTGTGCCTGCCTACA gi|703103|     ------------------------------------------------------------
Contig1_2      GAGCCCTGGGGCCTTCTCTTCCCAACTCCCAGCCACCCCCTGAGGTCTATGTGAGCCTGA gi|703103|     ------------------------------------------------------------
Contig1_2      TCAAGGCCTGCGGTGGTCCTGGAAATTTCTGCCCATCCTTCAGCGAGCTGCAGAGAAATT gi|703103|     ------------------------------------------------------------
Contig1_2      TCGTGAAACATCGGCCAACTAAGCTGAAGAGCCTCCTGCGCCTGGTGAAACACTGGTACC gi|703103|     ------------------------------------------------------------
Contig1_2      AGCAGTATGTGAAAGCCAGGTCCCCCAGAGCCAATCTGCCCCCTCTCTATGCTCTTGAAC gi|703103|     ------------------------------------------------------------
Contig1_2      TTCTAACCATCTATGCCTGGGAAATGGGTACTGAAGAAGACGAGAATTTCATGTTGGACG gi|703103|     -----TTCACCACTGTGATGGACCTGCTCCTGGAGTATGAAGTCATCTGTATCTACTGGA
Contig1_2      AAGGCTTCACCACTGTGATGGACCTGCTCCTGGAGTATGAAGTCATCTGTATCTACTGGA
                    ************************************************ gi|703103|     CCAAGTACTACACACTCCACAATGCAATCATTGAGGATTGTGTCAGAAAACAGCTCAAAA
Contig1_2      CCAAGTACTACACACTCCACAATGCAATCATTGAGGATTGTGTCAGAAAACAGCTCAAAA
               ************************************************************ gi|703103|     AAGAGAGGCCCATCATCCTGGATCCGGCCGACCCCACCCTCAACGTGGCAGAAGGGTACA
Contig1_2      AAGAGAGGCCCATCATCCTGGATCCGGCCGACCCCACCCTCAACGTGGCAGAAGGGTACA
               ************************************************************ gi|703103|     GATGGGACATCGTTGCTCAGAGGGCCTCCCAGTGCCTGAAACAGGACTGTTGCTATGACA
Contig1_2      GATGGGACATCGTTGCTCAGAGGGCCTCCCAGTGCCTGAAACAGGACTGTTGCTATGACA
               ************************************************************ gi|703103|     ACAGGGAGAAGGGGATCTCCAGCTGGAACGTGAAGAGGGCACGAGACATCCACTTGACAG
Contig1_2      ACAGGGAGAACCCCATCTCCAGCTGGAACGTGAAGAGGGCACGAGACATCCACTTGACAG
               *******   ********************************************** gi|703103|     TGGAGCAGAGGGGTTACCCAGATTTCAACCTCATCGTGAACCCTTATGAGCCCATAAGGA
Contig1_2      TGGAGCAGAGGGGTTACCCAGATTTCAACCTCATCGTGAACCCTTATGAGCCCATAAGGA
               ************************************************************
```

Fig. 2B

```
gi|703103|   AGGTTAAAGAGAAAATCCGGAG-ACCAGGGGCTACTCTGGCCTGCAGCGTCTGTCCTTCC
Contig1_2    AGGTTAAAGAGAAAATCCGGAGGACCAGGGGCTACTCTGGCCTGCAGCGTCTGTCCTTCC
             ******************* ************************************ gi|703103|   AGGTTCCTGGCAGTGAGAGGCAGCTTCTCAGCAGCAGGTGCTCCTTAGCCAAATAT----
Contig1_2    AGGTTCCTGGCAGTGAGAGGCAGCTTCTCAGCAGCAGGTGCTCCTTAGCCAAATATGGGA
             ******************************************************** gi|703103|   ------------------------------------------------------------
Contig1_2    TCTTCTCCCACACTCACATCTATCTGCTGGAGACCATCCCCTCCGAGATCCAGGTCTTCG gi|703103|   ------------------------------------------------------------
Contig1_2    TGAAGAATCCTGATGGTGGGAGCTACGCCTATGCCATCAACCCCAACAGCTTCATCCTGG gi|703103|   ------------------------------------------------------------
Contig1_2    GTCTGAAGCAGCAGATTGAAGACCAGCAGGGGCTTCCTAAAAAGCAGCAGCAGCTGGAAT gi|703103|   ------------------------------------------------------------
Contig1_2    TCCAAGGCCAAGTCCTGCAGGACTGGTTGGGTCTGGGGATCTATGGCATCCAAGACAGTG gi|703103|   ------------------------------------------------------------
Contig1_2    ACACTCTCATCCTCTCGAAGAAGAAAGGAGAGGCTCTGTTTCCAGCCAGTTAGTTTTCTC gi|703103|   ------------------------------------------------------------
Contig1_2    TGGGAGACTTCTCTGTACATTTCTGCCATGTACTCCAGAACTCATCCTGTCAATCACTCT gi|703103|   ------------------------------------------------------------
Contig1_2    GTCCCATTGTCTACTGGGAAGGTCCCAGGTCTTCACCAGTTTTACAATGAGTTATCCCAG gi|703103|   ------------------------------------------------------------
Contig1_2    GCCAGACGTGGTAGCTCACACCTGTAATCCCAGAACTTTGGGAAGCCCAAGTGGGAGGAA gi|703103|   ------------------------------------------------------------
Contig1_2    CGCTTGAACCCAGGATTCAA
```

Fig. 2C

CLUSTAL W(1.4) multiple sequence alignment

TRBP
TRIP14

Contig1_2      MALMQELYSTPASRLDSFVAQWLQPHREWKEEVLDAVRTVEEFLRQEHFQGKRGLDQDVR
gi|703104      ------------------------------------------------------------

Contig1_2      VLKVVKVGSFGNGTVLRSTREVELVAFLSCFHSFQEAAKHHKDVLRLIWKTMWQSQDLLD
gi|703104      ------------------------------------------------------------

Contig1_2      LGLEDLRMEQRVPDALVFTIQTRGTAEPITVTIVPAYRALGPSLPNSQPPPEVYVSLIKA
gi|703104      ------------------------------------------------------------

Contig1_2      CGGPGNFCPSFSELQRNFVKHRPTKLKSLLRLVKHWYQQYVKARSPRANLPPLYALELLT
gi|703104      ------------------------------------------------------------

Contig1_2      IYAWEMGTEEDENFMLDEGFTTVMDLLLEYEVICIYWTKYYTLHNAIIEDCVRKQLKKER
gi|703104      --------------------FTTVMDLLLEYEVICIYWTKYYTLHNAIIEDCVRKQLKKER
                                   ****************************************

Contig1_2      PIILDPADPTLNVAEGYRWDIVAQRASQCLKQDCCYDNRENPISSWNVKRARDIHLTVEQ
gi|703104      PIILDPADPTLNVAEGYRWDIVAQRASQCLKQDCCYDNREKGISSWNVKRARDIHLTVEQ
               **************************************  ***************

Contig1_2      RGYPDFNLIVNPYEPIRKVKEKIRRTRGYSGLQRLSFQVPGSERQLLSSRCSLAKYGIFS
gi|703104      RGYPDFNLIVNPYEPIRKVKEKIRR--------------PG--ATLACSVC---------
               ***********************                 * .* *

Contig1_2      HTHIYLLETIPSEIQVFVKNPDGGSYAYAINPNSFILGLKQQIEDQQGLPKKQQQLEFCG
gi|703104      ----------PSRFLAVR-----GSFSAAGAP----------------------------
                           ..    **  * *

Contig1_2      QVLQDWLGLGIYGIQDSDTLILSKKKGEALFPAS
gi|703104      ----------------------------------

Fig. 3

ATGGCACTGATGCAGGAACTGTATAGCACACCAGCCTCCAGGCTGGACTCCTTCGTGGCTCAGTG
GCTGCAGCCCCACCGGGAGTGGAAGGAAGAGGTGCTAGACGCTGTGCGGACCGTGGAGGAGTTTC
TGAGGCAGGAGCATTTCCAGGGGAAGCGTGGGCTGGACCAGGATGTGCGGGTGCTGAAGGTAGTC
AA...........intron1........GGGTGGTGAGCATTCAGTGAGACAGTGCATGTGAAGT
GCCGCAGGGTTGCCTGGCTCATGGCAGTGGGCCTCAGGGTGACGGGGCTCTGTGTTCTSMAGGTG
GGCTCCTTCGGGAATGGCACGGTTCTCAGGAGCACCAGAGAGGTGGAGCTGGTGGCGTTTCTGAG
CTGTTTCCACAGCTTCCAGGAGGCAGCCAAGCATCACAAAGATGTTCTGAGGCTGATATGGAAAA
CCATGTGGCAAAGCCAGGACCTGCTGGACCTCGGGCTCGAGGACCTGAGGATGGAGCAGAGAGTC
CCCGATGCTCTTGTCTTCACCATCCAGACCAGGGGGACTGCGGAGCCCATCACGGTCACCATTGT
GCCTGCCTACAGAGCCCTG......intron2.........GGATACTTCCAATGTAAAGGCAGG
CTCTCCCCAAAATACTACTTACCACCCTCTGGCTTCCTCAATCCCCAATCTCTTCCTTTGCTCCT
TCACTCCTCAGGGCCTTCTCTTCCCAACTCCCAGCCACCCCCTGAGGTCTATGTGAGCCTGATCA
AGGCCTGCGGTGGTCCTGGAAATTTCTGCCCATCCTTCAGCGAGCTGCAGAGAAATTTCGTGAAA
CATCGGCCAACTAAGCTGAAGAGCCTCCTGCGCCTGGTGAAACACTGGTACCAGCA........i
ntron3........GTATGTGAAAGCCAGGTCCCCCAGAGCCAATCTGCCCCCTCTCTATGCTCT
TGAACTTCTAACCATCTATGCYTGGGAAATGGGTACTGAAGAAGACGAGAATTTCATGTTGGACG
AAGGCTTCACCACTGTGATGGACCTGCTCCTGGAGTATGAAGTCATCTGTATCTACTGGACCAAG
TACTACACACTCCACAATGCAATCATTGAGGATTGTGTCAGAAAACAGCTCAAAAAAGAGAG...
...intron4......GATATCACAATTCTCAGTGGCTGGACGAAATAATTGCCGAGAAGGTTTT
TTNCTGGCTTGAAGGCCTTCAAACCATTATAAGCCTGGGCACCCTTTTCCTGTGTTACAGGCCCA
TCATCCTGGATCCGGCCGACCCCACCCTCAACGTGGCAGAAGGGTACAGATGGGACATCGTTGCT
CAGAGGGCCTCCCAGTGCCTGAAACAGGACTGTTGCTATGACAACAGGGAGAACCCCATCTCCAG
CTGGAACGTGAAGGTAATGGCTCCTCTCTGGGCTTTCAAGGGCTTGAAGGTCAGAACGACAGATA
AACTACTCAGTATTTACTCATTCAGTTCTGTGTTGATGGAGAACA..............intron5
..................GTGTGCGTGTGTGTATATGTAAGATAGGACAGTGAGGACATTGNAAT
CAGACAAGAAGGGGATNAAACTNTCTTTTCCTNTCCTTCCAGAGGGCACGAGACATCCACTTGAC
AGTGGAGCAGAGGGGTTACCCAGATTTCAACCTCATCGTGAACCCTTATGAGCCCATAAGGAAGG
TTAAAGAGAAAATCCGGAGGACCAGGGGCTACTCTGGCCTGCAGCGTCTGTCCTTCCAGGTTCCT
GGCAGTGAGAGGCAGCTTCTCAGCAGCAGGTGCTCCTTAGCCAAATATGGGATCTTCTCCCACAC
TCACATCTATCTGCTGGAGACCATCCCCTCCGAGATCCAGGTCTTCGTGAAGAATCCTGATGGTG
GGAGCTACGCCTATGCCATCAACCCCAACAGCTTCATCCTGGGTCTGAAGCAGCAGATTGAAGAC
CAGCAGGGGCTTCCTAAAAAGCAGCAGCAGCTGGAATTCCAAGGCCAAGTCCTGCAGGACTGGTT
GGGTCTGGGGATCTATGGCATCCAAGACAGTGACACTCTCATCCTCTCGAAG.....intron6.
.....AAGAAAGGAGAGGCTCTGTTTCCAGCCAGTTAGTTTTCTC....

Fig. 4

TRBP
2,5A

```
fih353prot  -----STPASRLDSFVAQWLQPHREWKEEVLDAVRTVEEFLRQEHFQGKRGLDQDVRVLK
gi|220081   MMDLRNTPAKSLDKFIEDYLLPDTCFRMQINHAIDIICGFLKERCFRGS---SYPVCVSK
                 *  *  * *    ... *. . **..  *.*         * * * fih353prot  VVKVGSFGNGTVLRSTREVELVAFLSCFHSFQEAAKHHKDVLRLIWKTMWQSQD--LLDL
gi|220081   VVKGGSSGKGTTLRGRSDADLVVFLSPLTTFQDQLNRRGEFIQEIRRQLEACQRERAFSV
            *** ** * ** **     .** ***   .**.  .. .....*... .*        .

fih353prot  GLEDLRMEQRVPDALVFTIQTRGTAEPITVTIVPAYRALGPSLPNSQPPPEVYVSLIKAC
gi|220081   KFEVQAPRWGNPRALSFVLSSLQLGEGVEFDVLPAFDALGQLTGSYKPNPQIYVKLIEEC
             *      * ** *  ..    *.    ... *      .* *..  * fih353prot  GGP---GNFCPSFSELQRNFVKHRPXKLKSLLRLVKHWYQQYVKARSPRANLPPLYALEL
gi|220081   TDLQKEGEFSTCFTELQRDFLKQRPTKLKSLIRLVKHWYQNCKKKLG---KLPPQYALEL
             *  .  *.**** *.*** *.* * ******. *        * *** fih353prot  LTIYAWEMGTEEDENFMLDEGFTTVMDLLLEYEVICIYWTKYYTLHNAIIEDCVRKQLKK
gi|220081   LTVYAWERGS-MKTHFNTAQGFRTVLELVINYQQLCIYWTKYYDFKNPIIEKYLRRQLTK
            **.**** *.    .*   .** **..*..* . ******** .* *** .*.** **

fih353prot  ERPIILDPADPTLNVAEG--YRWDIVAQRASQCLKQDCCYDNRENPISSWNVKRARDIHL
gi|220081   PRPVILDPADPTGNLGGGDPKGWRQLAQEAEAWLNYPCFKNWDGSPVSSW----------
             .****** *. *   * *  .**   *  ..* * * *   .*** fih353prot  TVEQRGYPDFNLIVNPYEPIRKVKEKIRRTGYSGLQRLSFQVPGSERQLLSSRCSLAKY
gi|220081   ----------ILLVRP----------------------------PASS-------------
                      *.* *                                * * fih353prot  GIFSHTHIYLLETIPSEIQVFVKNPDGGSYAYAINPNSFILGLKQQIEDQQGLPKKQQQL
gi|220081   ----------LPFIPAPLHEA---------------------------------------
                      *  **. ..

fih353prot  EFQGQVLQDWLGLGIYGIQDSDTLILSKKKGEALFPAS
gi|220081   -------------------------------------
```

Fig. 5

TRBP
UBIQUITIN

| | |
|---|---|
| fih353prot | STPASRLDSFVAQWLQPHREWKEEVLDAVRTVEEFLRQEHFQGKRGLDQDVRVLKVVKVG |
| gi\|1490419 | ------------------------------------------------------------ |

| | |
|---|---|
| fih353prot | SFGNGTVLRSTREVELVAFLSCFHSFQEAAKHHKDVLRLIWKTMWQSQDLLDLGLEDLRM |
| gi\|1490419 | --------------------------------------MQIFVKTLTG------------ |
| | ... **. |

| | |
|---|---|
| fih353prot | EQRVPDALVFTIQTRGTAEPITVTIVPAYRALGPSLPNSQPPPEVYVSLIKACGGPGNFC |
| gi\|1490419 | -------KTITLEVE---PSDTIENVKAKIQDKEGIPPDQ---Q--R-LIFAG------- |
| | *..     *. **       . * *    .    ** * |

| | |
|---|---|
| fih353prot | PSFSELQRNFVKHRPXKLKSLLRLVKHWYQQYVKARSPRANLPPLYALELLTIYAWEMGT |
| gi\|1490419 | -----------KQLE-----------------DGR-----------------------T |
| | *.                             *                         * |

| | |
|---|---|
| fih353prot | EEDENFMLDEGFTTVMDLLLEYEVICIYWTKYYTLHNAIIEDCVRKQLKKERPIILDPAD |
| gi\|1490419 | LSDYNIQKESTLHLVLRLRGGMQIFVKTLT------------------------------ |
| | * *   .    *.*   ..    * |

| | |
|---|---|
| fih353prot | PTLNVAEGYRWDIVAQRASQCLKQDCCYDNRENPISSWNVKRARDIHLTVEQRGYPDFNL |
| gi\|1490419 | --------------------------------------------GKTITLEVE-------- |
| | .  * * ** |

| | |
|---|---|
| fih353prot | IVNPYEPIRKVKEKIRRTRGYSG-LQRLSFQVPGSERQLLSSRCSLAKYGIFSHTHIYLL |
| gi\|1490419 | ---PSDTIENVKAKIQDKEGIPPDQQRLIFAG----KQLEDGR-TLSDYNIQKESTLHLV |
| | *. *  ** **.  *      *** *    .**   *.*. *.*   . .*. |

| | |
|---|---|
| fih353prot | ETIPSEIQVFVKNPDGGSYAYAINPNSFILGLKQQIEDQQGLPKKQQQLEFQGQVLQDWL |
| gi\|1490419 | LRLRGGMQIFVKTLTGKTITLEVEPSDTIENVKAKIQDKEGIPPDQQRLIFAGKQLEDGR |
| | .  .*.***. *...  *      *  *..*  .*.*...*.*  .* *.* |

| | |
|---|---|
| fih353prot | GLGIYGIQDSDTLILSKKKGEALFPAS |
| gi\|1490419 | TLSDYNIQKESTLHLVLR----LRGGC |
| | *  *.**  ** *   .    * . |

Fig. 6

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
      (A) LENGTH: 2241 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 490..2031

(xi) SEQUENCE DESCRIPTION: SEQ ID NO:1:

```
CGCCATTGGT TCTCTAGATG CATGCCCGAG CGGCCGCCAG TGTGCTCTAA AGGCCTCAAT        60

TTCCTTAGAC AGATGTAAGC AGTTGAATTG ACTAACAACT ATCCAACCCC AACCTACTGG       120

GCAAGTTGCC TCCTTTGGGG TCAAACACTA TCCAACTTCA GTTTCCCAAC GTCATAAAGG       180
```

-continued

```
AGAACTCTAA AAGTTGAGAA TCGAAACTGA TGACAGACTG ACTAGACGGC CAGCCTGTTA      240

AGGTGGCCCC AGATATTCCA GCCTCAGCCC AGAGTCCTCC TGTGCCCCTA CTGCAGCAAG      300

GGTGTCTCCA GAAGGGGGA CCTGGAGTCA GCCCGTCACA CCTGGTTTCC TCTCTGCTAN       360

GGTCCCTCCT CCCACAGAGC ACTGGAGGGC AGCTGAAGAA GAGCTACCTT AAAAAAGGAA      420

GTGTGTGCCA GGGAACTGGG TAGGAACCTG GCTATATATC TGCCCAGCAG CGGTACTCTC      480

GGGACAGAG ATG GCA CTG ATG CAG GAA CTG TAT AGC ACA CCA GCC TCC          528
          Met Ala Leu Met Gln Glu Leu Tyr Ser Thr Pro Ala Ser
            1               5                  10

AGG CTG GAC TCC TTC GTG GCT CAG TGG CTG CAG CCC CAC CGG GAG TGG        576
Arg Leu Asp Ser Phe Val Ala Gln Trp Leu Gln Pro His Arg Glu Trp
 15              20                  25

AAG GAA GAA GTG CTA GAC GCT GTG CGG ACC GTG GAA GAA TTT CTG AGG        624
Lys Glu Glu Val Leu Asp Ala Val Arg Thr Val Glu Glu Phe Leu Arg
 30              35                  40                          45

CAG GAG CAT TTC CAG GGG AAG CGT GGG CTG GAC CAG GAT GTG CGG GTG        672
Gln Glu His Phe Gln Gly Lys Arg Gly Leu Asp Gln Asp Val Arg Val
                 50                  55                  60

CTG AAG GTA GTC AAG GTG GGC TCC TTC GGG AAT GGC ACG GTT CTC AGG        720
Leu Lys Val Val Lys Val Gly Ser Phe Gly Asn Gly Thr Val Leu Arg
             65                  70                  75

AGC ACC AGA GAG GTG GAG CTG GTG GCG TTT CTG AGC TGT TTC CAC AGC        768
Ser Thr Arg Glu Val Glu Leu Val Ala Phe Leu Ser Cys Phe His Ser
         80                  85                  90

TTC CAG GAG GCA GCC AAG CAT CAC AAA GAT GTT CTG AGG CTG ATA TGG        816
Phe Gln Glu Ala Ala Lys His His Lys Asp Val Leu Arg Leu Ile Trp
     95                  100                 105

AAA ACC ATG TGG CAA AGC CAG GAC CTG CTG GAC CTC GGG CTC GAG GAC        864
Lys Thr Met Trp Gln Ser Gln Asp Leu Leu Asp Leu Gly Leu Glu Asp
110                 115                 120                 125

CTG AGG ATG GAG CAG AGA GTC CCC GAT GCT CTT GTC TTC ACC ATC CAG        912
Leu Arg Met Glu Gln Arg Val Pro Asp Ala Leu Val Phe Thr Ile Gln
                130                 135                 140

ACC AGG GGG ACT GCG GAG CCC ATC ACG GTC ACC ATT GTG CCT GCC TAC        960
Thr Arg Gly Thr Ala Glu Pro Ile Thr Val Thr Ile Val Pro Ala Tyr
            145                 150                 155

AGA GCC CTG GGG CCT TCT CTT CCC AAC TCC CAG CCA CCC CCT GAG GTC       1008
Arg Ala Leu Gly Pro Ser Leu Pro Asn Ser Gln Pro Pro Pro Glu Val
        160                 165                 170

TAT GTG AGC CTG ATC AAG GCC TGC GGT GGT CCT GGA AAT TTC TGC CCA       1056
Tyr Val Ser Leu Ile Lys Ala Cys Gly Gly Pro Gly Asn Phe Cys Pro
    175                 180                 185

TCC TTC AGC GAG CTG CAG AGA AAT TTC GTG AAA CAT CGG CCA ACT AAG       1104
Ser Phe Ser Glu Leu Gln Arg Asn Phe Val Lys His Arg Pro Thr Lys
190                 195                 200                 205

CTG AAG AGC CTC CTG CGC CTG GTG AAA CAC TGG TAC CAG CAG TAT GTG       1152
Leu Lys Ser Leu Leu Arg Leu Val Lys His Trp Tyr Gln Gln Tyr Val
                210                 215                 220

AAA GCC AGG TCC CCC AGA GCC AAT CTG CCC CCT CTC TAT GCT CTT GAA       1200
Lys Ala Arg Ser Pro Arg Ala Asn Leu Pro Pro Leu Tyr Ala Leu Glu
            225                 230                 235

CTT CTA ACC ATC TAT GCC TGG GAA ATG GGT ACT GAA GAA GAC GAG AAT       1248
Leu Leu Thr Ile Tyr Ala Trp Glu Met Gly Thr Glu Glu Asp Glu Asn
        240                 245                 250

TTC ATG TTG GAC GAA GGC TTC ACC ACT GTG ATG GAC CTG CTC CTG GAG       1296
Phe Met Leu Asp Glu Gly Phe Thr Thr Val Met Asp Leu Leu Leu Glu
    255                 260                 265
```

```
TAT GAA GTC ATC TGT ATC TAC TGG ACC AAG TAC TAC ACA CTC CAC AAT      1344
Tyr Glu Val Ile Cys Ile Tyr Trp Thr Lys Tyr Tyr Thr Leu His Asn
270             275                 280                 285

GCA ATC ATT GAG GAT TGT GTC AGA AAA CAG CTC AAA AAA GAG AGG CCC      1392
Ala Ile Ile Glu Asp Cys Val Arg Lys Gln Leu Lys Lys Glu Arg Pro
                290                 295                 300

ATC ATC CTG GAT CCG GCC GAC CCC ACC CTC AAC GTG GCA GAA GGG TAC      1440
Ile Ile Leu Asp Pro Ala Asp Pro Thr Leu Asn Val Ala Glu Gly Tyr
            305                 310                 315

AGA TGG GAC ATC GTT GCT CAG AGG GCC TCC CAG TGC CTG AAA CAG GAC      1488
Arg Trp Asp Ile Val Ala Gln Arg Ala Ser Gln Cys Leu Lys Gln Asp
        320                 325                 330

TGT TGC TAT GAC AAC AGG GAG AAC CCC ATC TCC AGC TGG AAC GTG AAG      1536
Cys Cys Tyr Asp Asn Arg Glu Asn Pro Ile Ser Ser Trp Asn Val Lys
335                 340                 345

AGG GCA CGA GAC ATC CAC TTG ACA GTG GAG CAG AGG GGT TAC CCA GAT      1584
Arg Ala Arg Asp Ile His Leu Thr Val Glu Gln Arg Gly Tyr Pro Asp
350                 355                 360                 365

TTC AAC CTC ATC GTG AAC CCT TAT GAG CCC ATA AGG AAG GTT AAA GAG      1632
Phe Asn Leu Ile Val Asn Pro Tyr Glu Pro Ile Arg Lys Val Lys Glu
                370                 375                 380

AAA ATC CGG AGG ACC AGG GGC TAC TCT GGC CTG CAG CGT CTG TCC TTC      1680
Lys Ile Arg Arg Thr Arg Gly Tyr Ser Gly Leu Gln Arg Leu Ser Phe
                385                 390                 395

CAG GTT CCT GGC AGT GAG AGG CAG CTT CTC AGC AGC AGG TGC TCC TTA      1728
Gln Val Pro Gly Ser Glu Arg Gln Leu Leu Ser Ser Arg Cys Ser Leu
            400                 405                 410

GCC AAA TAT GGG ATC TTC TCC CAC ACT CAC ATC TAT CTG CTG GAG ACC      1776
Ala Lys Tyr Gly Ile Phe Ser His Thr His Ile Tyr Leu Leu Glu Thr
        415                 420                 425

ATC CCC TCC GAG ATC CAG GTC TTC GTG AAG AAT CCT GAT GGT GGG AGC      1824
Ile Pro Ser Glu Ile Gln Val Phe Val Lys Asn Pro Asp Gly Gly Ser
430                 435                 440                 445

TAC GCC TAT GCC ATC AAC CCC AAC AGC TTC ATC CTG GGT CTG AAG CAG      1872
Tyr Ala Tyr Ala Ile Asn Pro Asn Ser Phe Ile Leu Gly Leu Lys Gln
                450                 455                 460

CAG ATT GAA GAC CAG CAG GGG CTT CCT AAA AAG CAG CAG CAG CTG GAA      1920
Gln Ile Glu Asp Gln Gln Gly Leu Pro Lys Lys Gln Gln Gln Leu Glu
                465                 470                 475

TTC CAA GGC CAA GTC CTG CAG GAC TGG TTG GGT CTG GGG ATC TAT GGC      1968
Phe Gln Gly Gln Val Leu Gln Asp Trp Leu Gly Leu Gly Ile Tyr Gly
            480                 485                 490

ATC CAA GAC AGT GAC ACT CTC ATC CTC TCG AAG AAG AAA GGA GAG GCT      2016
Ile Gln Asp Ser Asp Thr Leu Ile Leu Ser Lys Lys Lys Gly Glu Ala
        495                 500                 505

CTG TTT CCA GCC AGT TAGTTTTCTC TGGGAGACTT CTCTGTACAT TTCTGCCATG      2071
Leu Phe Pro Ala Ser
510

TACTCCAGAA CTCATCCTGT CAATCACTCT GTCCCATTGT CTACTGGGAA GGTCCCAGGT   2131

CTTCACCAGT TTTACAATGA GTTATCCCAG GCCAGACGTG GTAGCTCACA CCTGTAATCC   2191

CAGAACTTTG GGAAGCCCAA GTGGAGGAA CGCTTGAACC CAGGATTCAA                2241

(2) INFORMATION FOR SEQ ID NO:2:

(i) SEQUENCE CHARACTERISTICS:
        (A) LENGTH: 514 amino acids
        (B) TYPE: amino acid
        (D) TOPOLOGY: linear
```

(ii) MOLECULE TYPE: protein (xi) SEQUENCE DESCRIPTION: SEQ ID NO:2:

```
Met Ala Leu Met Gln Glu Leu Tyr Ser Thr Pro Ala Ser Arg Leu Asp
 1               5                  10                  15

Ser Phe Val Ala Gln Trp Leu Gln Pro His Arg Glu Trp Lys Glu Glu
                20                  25                  30

Val Leu Asp Ala Val Arg Thr Val Glu Glu Phe Leu Arg Gln Glu His
            35                  40                  45

Phe Gln Gly Lys Arg Gly Leu Asp Gln Asp Val Arg Val Leu Lys Val
        50                  55                  60

Val Lys Val Gly Ser Phe Gly Asn Gly Thr Val Leu Arg Ser Thr Arg
65                  70                  75                  80

Glu Val Glu Leu Val Ala Phe Leu Ser Cys Phe His Ser Phe Gln Glu
                85                  90                  95

Ala Ala Lys His His Lys Asp Val Leu Arg Leu Ile Trp Lys Thr Met
                100                 105                 110

Trp Gln Ser Gln Asp Leu Leu Asp Leu Gly Leu Glu Asp Leu Arg Met
            115                 120                 125

Glu Gln Arg Val Pro Asp Ala Leu Val Phe Thr Ile Gln Thr Arg Gly
        130                 135                 140

Thr Ala Glu Pro Ile Thr Val Thr Ile Val Pro Ala Tyr Arg Ala Leu
145                 150                 155                 160

Gly Pro Ser Leu Pro Asn Ser Gln Pro Pro Glu Val Tyr Val Ser
                165                 170                 175

Leu Ile Lys Ala Cys Gly Gly Pro Gly Asn Phe Cys Pro Ser Phe Ser
                180                 185                 190

Glu Leu Gln Arg Asn Phe Val Lys His Arg Pro Thr Lys Leu Lys Ser
            195                 200                 205

Leu Leu Arg Leu Val Lys His Trp Tyr Gln Gln Tyr Val Lys Ala Arg
        210                 215                 220

Ser Pro Arg Ala Asn Leu Pro Pro Leu Tyr Ala Leu Glu Leu Leu Thr
225                 230                 235                 240

Ile Tyr Ala Trp Glu Met Gly Thr Glu Glu Asp Glu Asn Phe Met Leu
                245                 250                 255

Asp Glu Gly Phe Thr Thr Val Met Asp Leu Leu Glu Tyr Glu Val
                260                 265                 270

Ile Cys Ile Tyr Trp Thr Lys Tyr Tyr Thr Leu His Asn Ala Ile Ile
            275                 280                 285

Glu Asp Cys Val Arg Lys Gln Leu Lys Lys Glu Arg Pro Ile Ile Leu
        290                 295                 300

Asp Pro Ala Asp Pro Thr Leu Asn Val Ala Glu Gly Tyr Arg Trp Asp
305                 310                 315                 320

Ile Val Ala Gln Arg Ala Ser Gln Cys Leu Lys Gln Asp Cys Cys Tyr
                325                 330                 335

Asp Asn Arg Glu Asn Pro Ile Ser Ser Trp Asn Val Arg Ala Arg
                340                 345                 350

Asp Ile His Leu Thr Val Glu Gln Arg Gly Tyr Pro Asp Phe Asn Leu
            355                 360                 365

Ile Val Asn Pro Tyr Glu Pro Ile Arg Lys Val Lys Glu Lys Ile Arg
        370                 375                 380

Arg Thr Arg Gly Tyr Ser Gly Leu Gln Arg Leu Ser Phe Gln Val Pro
385                 390                 395                 400
```

```
Gly Ser Glu Arg Gln Leu Leu Ser Ser Arg Cys Ser Leu Ala Lys Tyr
            405                 410                 415

Gly Ile Phe Ser His Thr His Ile Tyr Leu Leu Glu Thr Ile Pro Ser
            420                 425                 430

Glu Ile Gln Val Phe Val Lys Asn Pro Asp Gly Gly Ser Tyr Ala Tyr
            435                 440                 445

Ala Ile Asn Pro Asn Ser Phe Ile Leu Gly Leu Lys Gln Gln Ile Glu
            450                 455                 460

Asp Gln Gln Gly Leu Pro Lys Lys Gln Gln Leu Glu Phe Gln Gly
465                 470                 475                 480

Gln Val Leu Gln Asp Trp Leu Gly Leu Gly Ile Tyr Gly Ile Gln Asp
            485                 490                 495

Ser Asp Thr Leu Ile Leu Ser Lys Lys Lys Gly Glu Ala Leu Phe Pro
            500                 505                 510

Ala Ser
```

(2) INFORMATION FOR SEQ ID NO:3:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:3:

CATGCTCCTT GGGATGT                                            17

(2) INFORMATION FOR SEQ ID NO:4:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:4:

TGAGGATTGC TTAAAGA                                            17

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:5:

ATCTCAGTGG TATTTGTGAG C                                      21

(2) INFORMATION FOR SEQ ID NO:6:

(i) SEQUENCE CHARACTERISTICS:
        (A) LENGTH: 20 base pairs
        (B) TYPE: nucleic acid (C) STRANDEDNESS: single
            (D) TOPOLOGY: linear (ii) MOLECULE TYPE: other nucleic acid
            (A) DESCRIPTION: /desc = "oligonucleotide"

(xi) SEQUENCE DESCRIPTION: SEQ ID NO:6:

TCTGAGTCAC CTGGACAACC                                            20

(2) INFORMATION FOR SEQ ID NO:7:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO:7:

CUACUACUAC UAGTGAACTG CACTGTGACA AGCTGC                           36

(2) INFORMATION FOR SEQ ID NO:8:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO:8:

CUACUACUAC UACACCTGAG GAGTGAATTG GTCG                             34

(2) INFORMATION FOR SEQ ID NO:9:

(i) SEQUENCE CHARACTERISTICS:
            (A) LENGTH: 470 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:9:

TTCACCACTG TGATGGACCT GCTCCTGGAG TATGAAGTCA TCTGTATCTA CTGGACCAAG    60

TACTACACAC TCCACAATGC AATCATTGAG GATTGTGTCA GAAAACAGCT CAAAAAAGAG   120

AGGCCCATCA TCCTGGATCC GGCCGACCCC ACCCTCAACG TGGCAGAAGG GTACAGATGG   180

GACATCGTTG CTCAGAGGGC CTCCCAGTGC CTGAAACAGG ACTGTTGCTA TGACAACAGG   240

GAGAAGGGGA TCTCCAGCTG GAACGTGAAG AGGGCACGAG ACATCCACTT GACAGTGGAG   300

CAGAGGGGTT ACCCAGATTT CAACCTCATC GTGAACCCTT ATGAGCCCAT AAGGAAGGTT   360

AAAGAGAAAA TCCGGAGACC AGGGGCTACT CTGGCCTGCA GCGTCGTTCC TTCCAGGTTC   420

CTGGCAGTGA GAGGCAGCTT CTCAGCAGCA GGTGCTCCTT AGCCAAATAT              470

(2) INFORMATION FOR SEQ ID NO:10:

(i) SEQUENCE CHARACTERISTICS:
            (A) LENGTH: 153 amino acids
            (B) TYPE: amino acid (C) STRANDEDNESS:
        (D) TOPOLOGY: linear (ii) MOLECULE TYPE: protein (xi) SEQUENCE DESCRIPTION: SEQ ID NO:10:

Phe Thr Thr Val Met Asp Leu Leu Leu Glu Tyr Glu Val Ile Cys Ile
1               5                   10                  15

Tyr Trp Thr Lys Tyr Tyr Thr Leu His Asn Ala Ile Ile Glu Asp Cys
                20                  25                  30

Val Arg Lys Gln Leu Lys Lys Glu Arg Pro Ile Ile Leu Asp Pro Ala
            35                  40                  45

Asp Pro Thr Leu Asn Val Ala Glu Gly Tyr Arg Trp Asp Ile Val Ala
        50                  55                  60

Gln Arg Ala Ser Gln Cys Leu Lys Gln Asp Cys Cys Tyr Asp Asn Arg
65                  70                  75                  80

Glu Lys Gly Ile Ser Ser Trp Asn Val Lys Arg Ala Arg Asp Ile His
                85                  90                  95

Leu Thr Val Glu Gln Arg Gly Tyr Pro Asp Phe Asn Leu Ile Val Asn
            100                 105                 110

Pro Tyr Glu Pro Ile Arg Lys Val Lys Glu Lys Ile Arg Arg Pro Gly
        115                 120                 125

Ala Thr Leu Ala Cys Ser Val Cys Pro Ser Arg Phe Leu Ala Val Arg
    130                 135                 140

Gly Ser Phe Ser Ala Ala Gly Ala Pro
145                 150

(2) INFORMATION FOR SEQ ID NO:11:

(i) SEQUENCE CHARACTERISTICS:
        (A) LENGTH: 197 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

ATGGCACTGA TGCAGGAACT GTATAGCACA CCAGCCTCCA GGCTGGACTC CTTCGTGGCT        60

CAGTGGCTGC AGCCCCACCG GGAGTGGAAG GAAGAGGTGC TAGACGCTGT GCGGACCGTG       120

GAGGAGTTTC TGAGGCAGGA GCATTTCCAG GGGAAGCGTG GGCTGGACCA GGATGTGCGG       180

GTGCTGAAGG TAGTCAA                                                      197

(2) INFORMATION FOR SEQ ID NO:12:

(i) SEQUENCE CHARACTERISTICS:
        (A) LENGTH: 381 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

GGGTGGTGAG CATTCAGTGA GACAGTGCAT GTGAAGTGCC GCAGGGTTGC CTGGCTCATG        60

GCAGTGGGCC TCAGGGTGAC GGGGCTCTGT GTTCTSMAGG TGGGCTCCTT CGGGAATGGC       120

ACGGTTCTCA GGAGCACCAG AGAGGTGGAG CTGGTGGCGT TTCTGAGCTG TTTCCACAGC       180

TTCCAGGAGG CAGCCAAGCA TCACAAAGAT GTTCTGAGGC TGATATGGAA AACCATGTGG       240

```
CAAAGCCAGG ACCTGCTGGA CCTCGGGCTC GAGGACCTGA GGATGGAGCA GAGAGTCCCC      300

GATGCTCTTG TCTTCACCAT CCAGACCAGG GGGACTGCGG AGCCCATCAC GGTCACCATT      360

GTGCCTGCCT ACAGAGCCCT G                                                 381
```

(2) INFORMATION FOR SEQ ID NO:13:

(i) SEQUENCE CHARACTERISTICS:
        (A) LENGTH: 275 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

```
GGATACTTCC AATGTAAAGG CAGGCTCTCC CCAAAATACT ACTTACCACC CTCTGGCTTC       60

CTCAATCCCC AATCTCTTCC TTTGCTCCTT CACTCCTCAG GGCCTTCTCT TCCCAACTCC      120

CAGCCACCCC CTGAGGTCTA TGTGAGCCTG ATCAAGGCCT GCGGTGGTCC TGGAAATTTC      180

TGCCCATCCT TCAGCGAGCT GCAGAGAAAT TTCGTGAAAC ATCGGCCAAC TAAGCTGAAG      240

AGCCTCCTGC GCCTGGTGAA ACACTGGTAC CAGCA                                 275
```

(2) INFORMATION FOR SEQ ID NO:14:

(i) SEQUENCE CHARACTERISTICS:
        (A) LENGTH: 243 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

```
GTATGTGAAA GCCAGGTCCC CCAGAGCCAA TCTGCCCCCT CTCTATGCTC TTGAACTTCT       60

AACCATCTAT GCYTGGGAAA TGGGTACTGA AGAAGACGAG AATTTCATGT TGGACGAAGG      120

CTTCACCACT GTGATGGACC TGCTCCTGGA GTATGAAGTC ATCTGTATCT ACTGGACCAA      180

GTACTACACA CTCCACAATG CAATCATTGA GGATTGTGTC AGAAAACAGC TCAAAAAGA      240

GAG                                                                    243
```

(2) INFORMATION FOR SEQ ID NO:15:

(i) SEQUENCE CHARACTERISTICS:
        (A) LENGTH: 355 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

```
GATATCACAA TTCTCAGTGG CTGGACGAAA TAATTGCCGA GAAGGTTTTT TNCTGGCTTG       60

AAGGCCTTCA AACCATTATA AGCCTGGGCA CCCTTTTCCT GTGTTACAGG CCCATCATCC      120

TGGATCCGGC CGACCCCACC CTCAACGTGG CAGAAGGGTA CAGATGGGAC ATCGTTGCTB      180

CAGAGGGCCT CCCAGTGCCT GAAACAGGAC TGTTGCTATG ACAACAGGGA GAACCCCATC      240

TCCAGCTGGA ACGTGAAGGT AATGGCTCCT CTCTGGGCTT TCAAGGGCTT GAAGGTCAGA      300

ACGACAGATA AACTACTCAG TATTTACTCA TTCAGTTCTG TGTTGATGGA GAACA          355
```

(2) INFORMATION FOR SEQ ID NO:16:

(i) SEQUENCE CHARACTERISTICS:
        (A) LENGTH: 554 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

```
GTGTGCGTGT GTGTATATGT AAGATAGGAC AGTGAGGACA TTGNAATCAG ACAAGAAGGG    60

GATNAAACTN TCTTTTCCTN TCCTTCCAGA GGGCACGAGA CATCCACTTG ACAGTGGAGC   120

AGAGGGGTTA CCCAGATTTC AACCTCATCG TGAACCCTTA TGAGCCCATA GGAAGGTTA    180

AAGAGAAAAT CCGGAGGACC AGGGGCTACT CTGGCCTGCA GCGTCTGTCC TTCCAGGTTC   240

CTGGCAGTGA GAGGCAGCTT CTCAGCAGCA GGTGCTCCTT AGCCAAATAT GGATCTTCT    300

CCCACACTCA CATCTATCTG CTGGAGACCA TCCCCTCCGA GATCCAGGTC TTCGTGAAGA   360

ATCCTGATGG TGGGAGCTAC GCCTATGCCA TCAACCCCAA CAGCTTCATC CTGGGTCTGA   420

AGCAGCAGAT TGAAGACCAG CAGGGGCTTC CTAAAAAGCA GCAGCAGCTG GAATTCCAAG   480

GCCAAGTCCT GCAGGACTGG TTGGGTCTGG GGATCTATGG CATCCAAGAC AGTGACACTC   540

TCATCCTCTC GAAG                                                    554
```

(2) INFORMATION FOR SEQ ID NO:17:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

```
AAGAAAGGAG AGGCTCTGTT TCCAGCCAGT TAGTTTTCTC                          40
```

(2) INFORMATION FOR SEQ ID NO:18:

(i) SEQUENCE CHARACTERISTICS:
        (A) LENGTH: 506 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:18:

```
Ser Thr Pro Ala Ser Arg Leu Asp Ser Phe Val Ala Gln Trp Leu Gln
  1               5                  10                  15

Pro His Arg Glu Trp Lys Glu Glu Val Leu Asp Ala Val Arg Thr Val
                 20                  25                  30

Glu Glu Phe Leu Arg Gln Glu His Phe Gln Gly Lys Arg Gly Leu Asp
             35                  40                  45

Gln Asp Val Arg Val Leu Lys Val Val Lys Val Gly Ser Phe Gly Asn
     50                  55                  60

Gly Thr Val Leu Arg Ser Thr Arg Glu Val Glu Leu Val Ala Phe Leu
 65                  70                  75                  80

Ser Cys Phe His Ser Phe Gln Glu Ala Ala Lys His His Lys Asp Val
                 85                  90                  95
```

```
Leu Arg Leu Ile Trp Lys Thr Met Trp Gln Ser Gln Asp Leu Leu Asp
            100                 105                 110

Leu Gly Leu Glu Asp Leu Arg Met Glu Gln Arg Val Pro Asp Ala Leu
            115                 120                 125

Val Phe Thr Ile Gln Thr Arg Gly Thr Ala Glu Pro Ile Thr Val Thr
            130                 135                 140

Ile Val Pro Ala Tyr Arg Ala Leu Gly Pro Ser Leu Pro Asn Ser Gln
145                 150                 155                 160

Pro Pro Pro Glu Val Tyr Val Ser Leu Ile Lys Ala Cys Gly Gly Pro
                165                 170                 175

Gly Asn Phe Cys Pro Ser Phe Ser Glu Leu Gln Arg Asn Phe Val Lys
            180                 185                 190

His Arg Pro Xaa Lys Leu Lys Ser Leu Leu Arg Leu Val Lys His Trp
            195                 200                 205

Tyr Gln Gln Tyr Val Lys Ala Arg Ser Pro Arg Ala Asn Leu Pro Pro
            210                 215                 220

Leu Tyr Ala Leu Glu Leu Leu Thr Ile Tyr Ala Trp Glu Met Gly Thr
225                 230                 235                 240

Glu Glu Asp Glu Asn Phe Met Leu Asp Glu Gly Phe Thr Thr Val Met
                245                 250                 255

Asp Leu Leu Leu Glu Tyr Glu Val Ile Cys Ile Tyr Trp Thr Lys Tyr
            260                 265                 270

Tyr Thr Leu His Asn Ala Ile Ile Glu Asp Cys Val Arg Lys Gln Leu
            275                 280                 285

Lys Lys Glu Arg Pro Ile Ile Leu Asp Pro Ala Asp Pro Thr Leu Asn
290                 295                 300

Val Ala Glu Gly Tyr Arg Trp Asp Ile Val Ala Gln Arg Ala Ser Gln
305                 310                 315                 320

Cys Leu Lys Gln Asp Cys Cys Tyr Asp Asn Arg Glu Asn Pro Ile Ser
            325                 330                 335

Ser Trp Asn Val Lys Arg Ala Arg Asp Ile His Leu Thr Val Glu Gln
            340                 345                 350

Arg Gly Tyr Pro Asp Phe Asn Leu Ile Val Asn Pro Tyr Glu Pro Ile
            355                 360                 365

Arg Lys Val Lys Glu Lys Ile Arg Arg Thr Arg Gly Tyr Ser Gly Leu
            370                 375                 380

Gln Arg Leu Ser Phe Gln Val Pro Gly Ser Glu Arg Gln Leu Leu Ser
385                 390                 395                 400

Ser Arg Cys Ser Leu Ala Lys Tyr Gly Ile Phe Ser His Thr His Ile
            405                 410                 415

Tyr Leu Leu Glu Thr Ile Pro Ser Glu Ile Gln Val Phe Val Lys Asn
            420                 425                 430

Pro Asp Gly Gly Ser Tyr Ala Tyr Ala Ile Asn Pro Asn Ser Phe Ile
            435                 440                 445

Leu Gly Leu Lys Gln Gln Ile Glu Asp Gln Gly Leu Pro Lys Lys
            450                 455                 460

Gln Gln Gln Leu Glu Phe Gln Gly Gln Val Leu Gln Asp Trp Leu Gly
465                 470                 475                 480

Leu Gly Ile Tyr Gly Ile Gln Asp Ser Asp Thr Leu Ile Leu Ser Lys
            485                 490                 495

Lys Lys Gly Glu Ala Leu Phe Pro Ala Ser
            500                 505
```

-continued (2) INFORMATION FOR SEQ ID NO:19:

(i) SEQUENCE CHARACTERISTICS:
        (A) LENGTH: 365 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:19:

```
Met Met Asp Leu Arg Asn Thr Pro Ala Lys Ser Leu Asp Lys Phe Ile
1               5                   10                  15
Glu Asp Tyr Leu Leu Pro Asp Thr Cys Phe Arg Met Gln Ile Asn His
            20                  25                  30
Ala Ile Asp Ile Ile Cys Gly Phe Leu Lys Glu Arg Cys Phe Arg Gly
        35                  40                  45
Ser Ser Tyr Pro Val Cys Val Ser Lys Val Lys Gly Gly Ser Ser
    50                  55                  60
Gly Lys Gly Thr Thr Leu Arg Gly Arg Ser Asp Ala Asp Leu Val Val
65                  70                  75                  80
Phe Leu Ser Pro Leu Thr Thr Phe Gln Asp Gln Leu Asn Arg Arg Gly
                85                  90                  95
Glu Phe Ile Gln Glu Ile Arg Arg Gln Leu Glu Ala Cys Gln Arg Glu
            100                 105                 110
Arg Ala Phe Ser Val Lys Phe Glu Val Gln Ala Pro Arg Trp Gly Asn
        115                 120                 125
Pro Arg Ala Leu Ser Phe Val Leu Ser Ser Leu Gln Leu Gly Glu Gly
    130                 135                 140
Val Glu Phe Asp Val Leu Pro Ala Phe Asp Ala Leu Gly Gln Leu Thr
145                 150                 155                 160
Gly Ser Tyr Lys Pro Asn Pro Gln Ile Tyr Val Lys Ile Leu Ile Glu
                165                 170                 175
Glu Cys Thr Asp Leu Gln Lys Glu Gly Glu Phe Ser Thr Cys Phe Thr
            180                 185                 190
Glu Leu Gln Arg Asp Phe Leu Lys Gln Arg Pro Thr Lys Leu Lys Ser
        195                 200                 205
Leu Ile Arg Leu Val Lys His Trp Tyr Gln Asn Cys Lys Lys Lys Leu
    210                 215                 220
Gly Lys Leu Pro Pro Gln Tyr Ala Leu Glu Leu Leu Thr Val Tyr Ala
225                 230                 235                 240
Trp Glu Arg Gly Ser Met Lys Thr His Phe Asn Thr Ala Gln Gly Phe
                245                 250                 255
Arg Thr Val Leu Glu Leu Val Ile Asn Tyr Gln Gln Leu Cys Ile Tyr
            260                 265                 270
Trp Thr Lys Tyr Tyr Asp Phe Lys Asn Pro Ile Ile Glu Lys Tyr Leu
        275                 280                 285
Arg Arg Gln Leu Thr Lys Pro Arg Pro Val Ile Leu Asp Pro Ala Asp
    290                 295                 300
Pro Thr Gly Asn Leu Gly Gly Gly Asp Pro Lys Gly Trp Arg Gln Leu
305                 310                 315                 320
Ala Gln Glu Ala Glu Ala Trp Leu Asn Tyr Pro Cys Phe Lys Asn Trp
                325                 330                 335
Asp Gly Ser Pro Val Ser Ser Trp Ile Leu Leu Val Arg Pro Pro Ala
            340                 345                 350
```

-continued

```
Ser Ser Leu Pro Phe Ile Pro Ala Pro Leu His Glu Ala
        355             360             365
```

(2) INFORMATION FOR SEQ ID NO:20:

(i) SEQUENCE CHARACTERISTICS:
        (A) LENGTH: 229 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:20:

```
Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Met Gln Ile Phe
65                  70                  75                  80

Val Lys Thr Leu Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
                100                 105                 110

Pro Pro Lys Gln Gln Arg Leu Ile Phe Ala Gly Lys Gln Leu Glu Asp
            115                 120                 125

Gly Arg Thr Leu Ser Asp Tyr Asn Ile Gln Lys Glu Ser Thr Leu His
    130                 135                 140

Leu Val Leu Arg Leu Arg Gly Gly Met Gln Ile Phe Val Lys Thr Leu
145                 150                 155                 160

Thr Gly Lys Thr Ile Thr Leu Glu Val Glu Pro Ser Asp Thr Ile Glu
                165                 170                 175

Asn Val Lys Ala Lys Ile Gln Asp Lys Glu Gly Ile Pro Pro Asp Gln
                180                 185                 190

Gln Arg Leu Ile Phe Ala Gly Lys Gln Leu Glu Asp Gly Arg Thr Leu
            195                 200                 205

Ser Asp Tyr Asn Ile Gln Lys Glu Ser Thr Leu His Leu Val Leu Arg
        210                 215                 220

Leu Arg Gly Gly Cys
225
```

ISOLATED NUCLEIC ACID ENCODING TRBP

1. Background of the Invention

Thyroid hormones, which include thyroxine ($T_4$) and triidothyronine ($T_3$) are involved in regulating organic metabolism and energy balance, growth and development, and the activity of the nervous system of an individual. Thyroid hormones stimulate carbohydrate and lipid catabolism in most cells of the body and increase the rate of protein synthesis. Since their overall effect is to stimulate catabolism, thyroid hormones increase the basal metabolic rate. As a result of catabolism, heat is give off, raising body temperature, a phenomenon termed calorigenic effect. Furthermore, thyroid hormones regulate tissue growth, in particular in children. Thyroid hormones are also involved in increasing the reactivity of the nervous system, thereby resulting in increased blood flow, increased and more forceful heartbeats, increased blood pressure, increased motility of the gatrointestinal tract and overall increased nervousness.

Abnormal levels of thyroid hormones or abnormal processing of thyroid hormones by cells can result in various disorders and conditions. For example, deficiency of thyroid hormones during fetal development can result in fewer and smaller neurons, defective myelination of axons, and mental retardation. During the early years of life, deficiency of thyroid hormones result in small stature and poor development of certain organs, such as the brain and reproductive structures, which can result in cretinism, characterized by dwarfism and mental retardation.

In the adult, hypothyroidism can produce myxedema, characterized by swelling of the facial tissues. A person having myxedema has a slow heart rate, low body temperature, sensitivity to cold, hypersensitivity to certain drugs (e.g., narcotics, barbiturates, and anesthetics), dry hair and skin, muscular weakness, general lethargy, and a tendency to easily gain weight. Due to the slowing of the heart rate, a person suffering from myxedema may overwork the heart muscles, causing the heart to enlarge. A person having myxedema may also lack mental alertness, due to dulling of nerve reactivity. The symptoms of myxedema can be alleviated by the administration of thyroid hormones.

Other diseases characterized by hypothyroidism include autoimmune diseases, such as atrophic (idiopathic) and Hashimoto's thyroiditis.

An excess of thyroid hormones, which can result, e.g., from hypersecretion of thyroid hormones or from an abnormality in the response of cells to thyroid hormone may also cause various disorders, generally termed thyrotoxicosis. The most common cause of thyrotoxicosis (excessive amounts of thyroid hormones) is Graves's disease, also called exophthalmic goiter. This disease is characterized by an enlarged thyroid, a goiter, which may be two or three times its normal size. The disease is also characterized by edema behind the eye, which causes the eye to protrude (exophthalmos). Other characteristic symptoms of this disease include an abnormally high metabolic rate, which can produce a range of effects including an increased pulse, high body temperature, heat intolerance, moist, flushed skin, loss of body weight. A person suffering from a disease characterized by excessive thyroid hormone levels has an increased response of the nervous system, causing the person to become irritable. This person may exhibit tremors of the extended fingers. Such diseases are treated classically by administration to the subject of antithyroid drugs that suppress the production of thyroid hormones, by treatment with radioactive iodine that selectively destroys thyroid cells, or by surgical removal of at least a portion of the thyroid gland.

An excessive level of thyroid hormone may also be caused by ingestion of excess iodine or lower than average iodine intake, or alternatively it may be caused genetically, and results in a condition termed simple goiter. Transient thyrotoxicosis is also frequently associated with thyroiditis. Yet other conditions resulting in thyrotoxicosis include toxic multinodular goiter, toxic adenoma, factitious thyrotoxicosis, thyrotoxicosis due to excess thyroid stimulating hormone (TSH), toxic thyroid carcinoma, toxic struma ovarii, and familial dysalbuminemic hyperthyroxinemia (FDH).

Thyroid hormones exert their wide ranging biological effects by interacting with thyroid hormone receptors which are present on a wide variety of cells. Thyroid hormone receptors (TRs) include TR-alpha (TR-α), TR-beta1 (TR-β1), and TR-beta2 (TR-β2), which are members of the steroid/thyroid superfamily of receptors, belong to the class of nuclear hormone receptors or nuclear receptors. This superfamily of protein includes, but is not limited to, glucocorticoid receptors (GR), mineralocorticoid receptors, progesterone receptors, estrogen receptors, the estrogen-related receptors, vitamin D3 receptors, retinoic acid receptors (RAR), retinoic X receptors (RXR), aldosterone receptors, and androgen receptors, which share structural homologies. Nuclear receptors are intracellular receptors which mediate the effects of steroid and thyroid hormones, as well as the metabolites of vitamin A (retinoic acid) and other hormones. Upon hormone binding, some receptors are translocated from the cytoplasm to the nucleus where they control the transcriptional expression of certain hormone-responsive genes. This involves the binding of the receptors, often in homo- or heterodimeric form, to specific sequences in the target gene promoter.

Sequence comparisons (Krust et al., EMBO J. 5:891, 1986) and structure-function analyses (Giguere et al., Cell 46:645, 1986; Kumar et al., Cell 51:941, 1987; Kumar and Chambon, Cell 55:145, 1988; and Green and Chambon, Nature 325:75, 1987) have shown that the receptors are composed of a series of conserved domains. The most highly conserved domain is the DNA binding domain located in region C (Krust et al., supra; Green and Chambon supra; and Evans and Hollenberg, Cell 52:1, 1988) containing a 66–68 amino acid core composed of two zinc fingers (Schwabe et al., Nature 348:458, 1990; Hard et al., Science 249:157, 1990; and Luisi et al., Nature 352:497, 1991) which is essential for recognition of regulatory elements (REs). Three amino acids adjacent to the N-terminal zinc finger of the DNA binding domain, known as the P-box, are critical for DNA sequence recognition (Mader et al., Nature 338:271, 1989; Umesomo and Evans, Cell 57:1139, 1989; and Danielson et al., 57 Cell 1131, 1989). The ligand binding domain, located C-terminal to the DNA binding domain in region E, is less well conserved among the receptors and contains a ligand-inducible transcriptional activation function (Green and Chambon, supra; Evans, supra; Wahli and Martinez, supra; Gronemeyer, supra; Giguere et al., Cell 46:645, 1986; and Kumar et al., Cell 51:941, 1987). Transcriptional activating domains have also been identified in the poorly conserved N-terminal A/B regions of the glucocorticoid and estrogen receptors (Giguere et al., supra; Kumar et al., supra; and Tora et al., Cell 59:447, 1989). Nuclear receptors and nucleic acids encoding such are further disclosed, e.g., U.S. Pat. No. 5,602,009, U.S. Pat. No. 5,552,271, U.S. Pat. No. 5,614,620 (androgen receptor), U.S. Pat. No. 5,606,021 (mineralocorticoid receptors), and U.S. Pat. No. 5,597,705

(thyroid hormone receptors). Nuclear hormone receptor binding elements are also further described in U.S. Pat. No. 5,597,693.

Furthermore, nuclear hormone receptors can have mutually antagonistic activities, such as transcriptional interference (Xhang et al. (1996) J. Biol. Chem. 271:14825). It has been proposed that this interference is due to the interaction of the activation domains of nuclear receptors with a common but limiting target protein in their signalling pathways. For example, several members of the steroid/thyroid superfamily have been shown to interact with basal transcription initiation factors, e.g., TFIIB, or TATA binding protein (TBP) or proteins from the TATA box-binding protein complex TFIID (Tong et al. (1995) J. Biol. Chem. 270:10601; Salovsky et al. (1995) Mol. Cell. Biol. 15:1554; and Jacq, et al. (1994) Cell 79:107). TRs have been shown to interact, e.g., with the related receptors for 9-cis-retinoic acid (9-cis-RA) and RXR. TR/RXR heterodimers have stronger DNA binding affinity relative to either receptor alone (Yu et al. (1991) Cell 67:1251). The yeast two-hybrid system has also been used to isolate cDNA encoding proteins that interact with the thyroid hormone receptor. (Lee et al. (1991) Endocrinology 9:243–254; PCT patent application having publication No. WO 94/10338).

2. Summary of the Invention

The invention is based at least in part on the discovery of a gene encoding a protein referred to herein as TRBP (Thyroid Hormone Receptor Binding Protein). A nucleic acid encoding a full length human TRBP has been isolated and has the nucleotide sequence set forth in SEQ ID No. 1. The nucleic acid encodes a protein of 514 amino acids having the amino acid sequence set forth in SEQ ID No. 2. A BAC clone of genomic DNA containing a human TRBP gene encoding the TRBP protein having SEQ ID No. 2 has been deposited with the American Type Culture Collection (ATCC) on Apr. 11, 1997 and has been assigned ATCC Designation Number 98407.

Accordingly, in one aspect, the invention provides nucleic acids encoding a TRBP protein, a portion thereof or a homolog thereof The invention also provides nucleic acids comprising a nucleotide sequence set forth in SEQ ID No. 1, a portion thereof or a homolog thereof Also within the scope of the invention are nucleic acids comprising a portion of the genomic sequence of the gene encoding TRBP e.g., comprising intronic sequences. As described herein, human genomic TRBP contains at least 7 exons and 6 introns, as shown in FIG. 4.

TRBP comprises a region having an amino acid sequence similarity to a portion of a protein termed thyroid receptor interacting protein 14 (TRIP14) (Lee et al. (1995) Endocrinology 9:243–254), which is capable of interacting with the rat thyroid hormone receptor β1 (TRβ1). Accordingly, the invention provides proteins and nucleic acids encoding such proteins which are capable of interacting with nuclear hormone receptors, such as a thryroid hormone receptor.

In another aspect, the invention provides methods for preventing or treating a disease, which is caused by, or contributed to by, an aberrant TRBP activity. In a preferred embodiment, the disease is a thyroid-related disorder or a metabolic disorder. In another preferred embodiment, the disease is diabetes, such as type II diabetes. In fact, the gene encoding TRBP is located on human chromosome 12q in a region which has been identified as containing one or more genes involved in type II diabetes such as non-insulin dependent diabetes mellitus (NIDDM). In preferred embodiments, a disease, e.g., diabetes (type II) is treated or prevented by administering to the subject a pharmaceutically effective amount of a compound that is capable of modulating a TRBP bioactivity, e.g., expression of a TRBP gene or binding of a TRBP polypeptide to a nuclear hormone receptor.

In a further aspect, the invention provides methods for modulating a TRBP activity, such as the expression of a gene encoding TRBP or a gene located downstream of TRBP in a biochemical pathway in which TRBP is involved. In another aspect of the invention, an activity of TRBP is modulated by administering to the subject a compound which modulates the interaction of TRBP with another molecule, e.g., a protein. A preferred protein is a nuclear receptor. An even more preferred receptor is a thyroid hormone receptor. Pharmaceutical compositions that modulate the expression of a gene, e.g., TRBP gene, or a TRBP activity can be a protein, a peptide, a peptidomimetic, or other small molecule or nucleic acid (e.g., gene replacement therapies, antisense, ribozyme and triplex nucleic acid constructs).

In a preferred embodiment, the pharmaceutical composition is comprised of an agonist of a normal (functional) TRBP bioactivity. For example, to ameliorate disease symptoms involving insufficient TRBP protein level or a TRBP protein having a less potent activity than the wild-type TRBP, an agonist therapeutic can be administered to the subject. The agonist can be, e.g., a compound which is capable of modulating TRBP gene expression or expression of a gene located downstream of TRBP in the biochemical pathway in which TRBP is involved. The agonist can also be a compound that is capable of modulating an interaction between TRBP and another molecule, e.g., a nuclear receptor.

In another preferred embodiment, the pharmaceutical composition is comprised of an antagonist of a TRBP bioactivity. For example, to ameliorate disease symptoms involving excessive TRBP protein levels or a TRBP protein having a more potent activity than the wild-type TRBP, an antagonist gene therapeutic or antagonist protein therapeutic can be administered to the subject. The antagonist can be, e.g., a compound that is capable of modulating TRBP gene expression or expression of a gene located downstream of TRBP in the biochemical pathway in which TRBP is involved. The antagonist can also be a compound that is capable of modulating an interaction of TRBP with another molecule, e.g., a nuclear receptor.

In yet another aspect, the invention provides assays, for screening test compounds to identify compounds that modulate a TRBP activity such as by modulating the expression of a TRBP gene. Such screening techniques can be performed in vitro or in vivo, in a cell or in an animal. In one embodiment, the assay comprises combining a TRAP protein, a TRBP binding partner, and a test compound under conditions wherein, but for the test compound, the TRBP protein and TRBP binding partner are able to interact, and detecting the formation of a TRBP/TRBP binding partner complex. A difference in formation of a TRBP protein TRBP binding partner complex in the presence of a test compound relative to in the absence of the test compound indicates that the test compound modulates a TRBP activity. Another assay for identifying a compound which modulates a TRBP activity or the expression of a TRBP gene, comprises contacting a cell expressing a TRBP polypeptide with a test compound and monitoring a TRBP activity, such as expression of a gene which is regulated by TRBP or a TRBP binding partner.

In a further embodiment, the invention provides screening assays to identify compounds suitable for treating a disease associated with an aberrant TRBP activity, e.g., diabetes type II or a metabolic disorder. In a disease in which the aberrant TRBP activity results from under-or-over-expression of the gene encoding TRBP or from an excessive or poor affinity for at least one other protein, a compound suitable for treating the disease can be identified by screening for compounds modulating the expression of the TRBP gene. Alternatively, compounds for treating such diseases can be identified by screening for compounds which modulate the interaction between TRBP and another molecule, e.g. protein.

The invention provides methods and kits for determining whether a subject is at risk of developing a disease associated with an aberrant TRBP activity, e.g., diabetes type II or a metabolic disorder. In one embodiment, the diagnostic method consists of determining a TRBP activity, such as the TRBP protein or mRNA level in cells from a subject. A higher or lower level of a TRBP activity, e.g., TRBP protein or mRNA level, relative to the TRBP activity in similar cells from a healthy subject which is not at risk of developing the disease, may be indicative that the subject is at risk of developing a disease contributed to by or caused by an aberrant TRBP level.

In another embodiment, the diagnostic methods and kits for determining whether a subject has or is at risk of developing a disease associated with an aberrant TRBP activity e.g., a thyroid-related disorder or type II diabetes include detecting, in a biological sample obtained from the subject, the presence or absence of a genetic lesion characterized by at least one of: (i) a mutation in a TRBP gene; (ii) the mis-expression of a TRBP gene; or (iii) an error or mutation in the promoter regulating a TRBP gene that may lead to aberrant expression. In preferred embodiments, detecting the genetic lesion includes ascertaining the existence of at least one of: (a) a deletion of one or more nucleotides from a wildtype gene; (b) an addition of one or more nucleotides to a wildtype gene; (c) a substitution of one or more nucleotides of a wildtype gene; (d) a gross chromosomal rearrangement of a wildtype gene; (e) an alteration in the level of a messenger RNA transcript of a gene; (f) the presence of a non-wild type splicing pattern of a messenger RNA transcript of a gene; and/or (h) an aberrant level of a protein.

For example, detecting the genetic lesion can include: (i) providing probes or primers comprised of an oligonucleotide which hybridizes to a sense or antisense sequence of a TRBP gene or gene fragment (wildtype or mutant); (ii) contacting the probes or primers to an appropriate nucleic acid containing biological sample obtained from the subject; and (iii) detecting, by hybridization of the probes or primers to the nucleic acid, the presence or absence of the genetic lesion.

In a preferred embodiment, the diagnostic methods and/ or kits utilize a set of primers for amplifying (e.g. via PCR or LCR) at least one region of a TRBP gene and means for analyzing the amplification product for differences (e.g. mutations) from the normal, wildtype coding sequence.

In another preferred embodiment, the diagnostic methods and/ or kits utilize a probe to determine its ability to hybridize under appropriately stringent conditions to a complementary nucleic acid sequence in the biological sample, wherein an inability of a probe, which is comprised of a wildtype TRBP sequence to hybridize to the sample nucleic acid is indicative of the presence of a mutation in the sample nucleic acid; or the ability of a probe, which is comprised of a mutant TRBP sequence to hybridize to the sample nucleic acid comprising a TRBP sequence or portion thereof is indicative of the presence of a mutation in the sample nucleic acid.

In yet a further preferred embodiment, the diagnostic methods and kits employ at least one antibody to at least one epitope, which is characteristic of a wildtype or mutant TRBP protein in an immunoassay procedure to detect the presence of a TRBP mutation in a biological sample obtained from a subject.

Other features and advantages of the invention will be apparent from the following detailed description and claims.

3. Brief Description of the Figures

FIG. 1 shows the nucleotide sequence of a full length human TRBP nucleic acid including 5' and 3' untranslated regions (SEQ ID No. 1) and the putative amino acid sequence (SEQ ID No. 2) of the encoded human TRBP protein.

FIG. 2 shows an alignment of the nucleic acid sequence SEQ ID No. 1 encoding human TRBP protein (bottom line) and the nucleic acid sequence having GenBank Accession No. L40387 (SEQ ID NO:9) encoding human TRIP14 (top line).

FIG. 3 shows an alignment of the amino acid sequence SEQ ID No. 2 of human TRBP protein (bottom line) and the amino acid sequence encoded by the nucleic acid having GenBank Accession No. L40387 (SEQ ID NO:10) encoding human TRIP14 (top line).

FIG. 4 shows the intron/exon boundaries in the human TRBP gene (SEQ ID NOS. 11–17, respectively). The underlined sequences represent the exons of TRBP.

FIG. 5 shows an alignment of a portion of the amino acid sequence SEQ ID No. 2 (SEQ ID NO:18) of human TRBP protein (top line) and the amino acid sequence (SEQ ID NO:19) of the human 2,5A oligoadenylate synthase having GenBank Accession No. D00068 (bottom line).

FIG. 6 shows an alignment of a portion of the amino acid sequence SEQ ID NO. 2 (SEQ ID NO:18) of human TRBP protein (top line) and the amino acid sequences (SEQ ID NO:20) of the ubiquitin protein having ATCC Designation No. 449869 (bottom line).

4. Detailed Description of the Invention 4.1. General

The invention pertains to nucleic acids encoding thyroid hormone receptor binding proteins (TRBPs). Preferred nucleic acids comprise the nucleic acid sequence SEQ ID No. 1 encoding a protein having SEQ ID No. 2, or nucleic acid sequences homologous thereto, or portions thereof The invention further provides isolated TRBP proteins. Preferred TRBP proteins comprise the amino acid sequence SEQ ID No. 2, amino acid sequences homologous thereto or portions thereof The gene encoding TRBP is located on human chromosome 12q between the markers AfMa82Za5 and AfM16Syb12, a chromosomal region identified as containing one or more genes involved in type II diabetes. One such gene is the gene MODY3, which encodes the nuclear hepatic factor-1α (HNF-1α), which cosegregates with maturity-onset diabetes of the young (MODY), a form of non-insulin dependent diabetes mellitus (NIDDM). In fact, mutations in the HNF-1α gene have been found in families. Further Mahtani et al. (Mathani et al. (1996) Mature Genetics 1α:90–94) report evidence of the existence of another gene in this chromosomal region, referred to as NIDDM2, that causes NIDDM associated with low insulin secretion.

Based on the location of the TRBP gene in a chromosomal region linked to type II diabetes, it is likely that one or more genetic lesions in the TRBP gene cause or contribute to diabetes. Alternatively, such genetic mutations could also result in other diseases, e.g. metabolic disorders, such as thyroid disorders. In fact, TRBP is significantly homologous to a protein fragment termed thyroid hormone receptor interacting protein 14 (TRIP 14) (Lee et al. (1995) J. Endocrinol. 9:243–254), which is capable of interacting with a thyroid hormone receptor. Accordingly, the invention provides diagnostic methods for determining whether a subject is at risk of developing a disease associated with an aberrant TRBP activity, e.g. diabetes type II or a metabolic disorder. Also within the scope of the invention are methods for treating such disorders and assays for isolating compounds for treating such diseases.

For convenience, the meaning of certain terms and phrases employed in the specification, examples, and appended claims are provided below.

4.2 Definitions

The term "agonist", as used herein, is meant to refer to an agent that upregulates (e.g. potentiates or supplements) a TRBP bioactivity. A TRBP agonist can be a compound that upregulates expression of a TRBP gene. Alternatively, a TRBP agonist can be a compound which increases signalling from a TRBP protein, e.g., a compound that is capable of binding to TRBP such as a small molecule. A TRBP agonist can also be a compound which modulates the expression or activity of a protein which is located downstream or upstream of TRBP or which interacts with TRBP.

"Antagonist" as used herein is meant to refer to an agent that downregulates (e.g. suppresses or inhibits) a TRBP bioactivity. An antagonist can be a compound that downregulates expression of a TRBP gene. Alternatively, a TRBP antagonist can be a compound which decreases signalling from a TRBP protein, e.g., a compound that is capable of binding to TRBP. A preferred TRBP antagonist inhibits the interaction between a TRBP protein and another molecule. A TRBP antagonist can also be a compound which modulates the expression or activity of a protein which is located downstream or upstream of Delta3 or which interacts with TRBP.

"Biological activity" or "bioactivity" or "activity" or "biological function", which are used interchangeably, for the purposes herein means an effector or antigenic function that is directly or indirectly performed by a TRBP polypeptide (whether in its native or denatured conformation), or by any subsequence thereof Biological activities include binding to a second protein, binding to a receptor, e.g., nuclear receptor, such as a thyroid hormone receptor, binding and/or activation or inactivation, in the presence or absence of a receptor ligand; regulation of expression of target genes, e.g., modulation of transcription from a promoter comprising a binding site directly or indirectly targeted by TRBP or a TRBP-binding protein; induction of cellular differentiation, mitogenic or growth promoting activity; induction of cell death; and/or immune modulation, whether presently known or inherent. A TRBP bioactivity can be modulated by affecting directly a TRBP protein. Alternatively, a TRBP bioactivity can be modulated by modulating the level of a TRBP protein, such as by modulating expression of a TRBP gene. Antigenic functions include possession of an epitope or antigenic site that is capable of cross-reacting with antibodies raised against a naturally occurring or denatured TRBP polypeptide or fragment thereof Biologically active TRBP polypeptides include polypeptides having both an effector and antigenic function, or only one of such functions. TRBP includes antagonist polypeptides and native TRBP, provided that such antagonists include an epitope of a native TRBP. An effector function of TRBP can be the ability to bind to a thyroid hormone receptor and regulate expression of a variety of specific target genes.

As used herein the term "bioactive fragment of a TRBP protein" refers to a fragment of a full-length TRBP protein, wherein the fragment specifically mimics or antagonizes the activity of a wild-type TRBP protein. The bioactive fragment preferably is a fragment capable of binding to a second protein, e.g., a receptor.

The term "an aberrant activity", as applied to an activity of a protein such as TRBP, refers to an activity which differs from the activity of the wild-type or native protein or which differs from the activity of the protein in a healthy subject. An activity of a protein can be aberrant because it is stronger than the activity of its native counterpart. Alternatively, an activity can be aberrant because it is weaker or absent related to the activity of its native counterpart. An aberrant activity can also be a change in an activity. For example an aberrant protein can interact with a different protein or nucleic acid sequence relative to its native counterpart. A cell can have an aberrant TRBP activity due to overexpression or underexpression of the gene encoding TRBP.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric protein" or "fusion protein" is a fusion of a first amino acid sequence encoding one of the subject TRBP polypeptides with a second amino acid sequence defining a domain (e.g. polypeptide portion) foreign to and not substantially homologous with any domain of a TRBP protein. A chimeric protein may present a foreign domain which is found (albeit in a different protein) in an organism which also expresses the first protein, or it may be an "interspecies", "intergenic", etc. fusion of protein structures expressed by different kinds of organisms. In general, a fusion protein can be represented by the general formula X-TRBP-Y, wherein TRBP represents a portion of the protein which is derived from a TRBP protein, and X and Y are independently absent or represent amino acid sequences which are not related to a TRBP sequence in an organism, including naturally occurring mutants.

"Complementary" sequences as used herein refer to sequences which have sufficient complementarity to be able to hybridize, forming a stable duplex.

A "delivery complex" shall mean a targeting means (e.g. a molecule that results in higher affinity binding of a gene, protein, polypeptide or peptide to a target cell surface and/or increased cellular or nuclear uptake by a target cell). Examples of targeting means include: sterols (e.g. cholesterol), lipids (e.g. a cationic lipid, virosome or liposome), viruses (e.g. adenovirus, adeno-associated virus, and retrovirus) or target cell specific binding agents (e.g. ligands recognized by target cell specific receptors). Preferred complexes are sufficiently stable in vivo to prevent significant uncoupling prior to internalization by the target cell. However, the complex is cleavable under appropriate conditions within the cell so that the gene, protein, polypeptide or peptide is released in a functional form.

As is well known, genes or a particular polypeptide may exist in single or multiple copies within the genome of an individual. Such duplicate genes may be identical or may have certain modifications, including nucleotide substitutions, additions or deletions, which all still code for polypeptides having substantially the same activity. The term "DNA sequence encoding a TRBP polypeptide" may thus refer to one or more genes within a particular individual. Moreover, certain differences in nucleotide sequences may exist between individual organisms, which are called alleles. Such allelic differences may or may not result in differences in amino acid sequence of the encoded polypeptide yet still encode a protein with the same biological activity.

"Diabetes" is a term used to refer to disorders, which relate to alterations in glucose homeostasis. In the mildest forms of diabetes, this alteration is detected only after challenge with a carbohydrate load, while in moderate to severe forms of disease, hyperglycemia is always present. Type I diabetes, insulin dependent diabetes mellitus or IDDM is the result of a progressive autoimmune destruction of the pancreatic β-cells with subsequent insulin deficiency. The more prevalent Type II, non-insulin dependent diabetes mellitus or NIDDM, is associated with peripheral insulin resistance, elevated hepatic glucose production, and inappropriate insulin secretion. Type II diabetes that develops during the age of 20–30 years old and is associated with chronic hyperglycemia and monogenic inheritance is referred to as maturity onset diabetes of the young (MODY). Other forms of Type II diabetes develop in an individual sometime after 20–30 years of age (e.g. late-onset NIDDM).

"Differential expression", as used herein, refers to both quantitative as well as qualitative differences in a gene's temporal and/or tissue expression patterns. Differentially expressed genes may represent "fingerprint genes," and/or "target genes."

A disease, disorder or condition "associated with" or "characterized by" an aberrant TRBP activity refers to a disease, disorder or condition in a subject which is caused by or contributed to by an aberrant TRBP activity.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are identical at that position. A degree of homology or similarity or identity between nucleic acid sequences is a function of the number of identical or matching nucleotides at positions shared by the nucleic acid sequences. A degree of identity of amino acid sequences is a function of the number of identical amino acids at positions shared by the amino acid sequences. A degree of homology or similarity of amino acid sequences is a function of the number of amino acids, i.e. structurally related, at positions shared by the amino acid sequences. An "unrelated" or "non-homologous" sequence shares less than 40% identity, though preferably less than 25% identity, with one of the TRBP sequences of the present invention.

The term "interact" as used herein is meant to include detectable interactions (e.g. biochemical interactions) between molecules, such as interaction between two proteins as can be detected using, for example, a yeast two hybrid assay. The term interact is also meant to include "binding" interactions between molecules. Interactions may, for example, be protein—protein, protein-nucleic acid, nucleic acid-nucleic acid, and protein-small molecule or nucleic acid-small molecule in nature.

A metabolic disease refers to a disease, condition, or disorder of a metabolic pathway, relating, e.g., to growth and development or to the activity of the nervous system. A preferred metabolic disease is thyroid hormone-related disorder.

The term "isolated" as used herein with respect to nucleic acids, such as DNA or RNA, refers to molecules separated from other DNAs, or RNAs, respectively, that are present in the natural source of the macromolecule. For example, an isolated nucleic acid encoding one of the subject TRBP polypeptides preferably includes no more than 10 kilobases (kb) of nucleic acid sequence which naturally immediately flanks the TRBP gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

The term "modulation" as used herein refers to both upregulation (i.e., activation or stimulation (e.g., by agonizing or potentiating)) and downregulation (i.e. inhibition or suppression (e.g., by antagonizing, decreasing or inhibiting)) the activity of a protein.

The "non-human animals" of the invention include mammalians such as rodents, non-human primates, sheep, dog, cow, chickens, amphibians, reptiles, etc. Preferred non-human animals are selected from the rodent family including rat and mouse, most preferably mouse, though transgenic amphibians, such as members of the Xenopus genus, and transgenic chickens can also provide important tools for understanding and identifying agents which can affect, for example, embryogenesis and tissue formation. The term "chimeric animal" is used herein to refer to animals in which the recombinant gene is found, or in which the recombinant is expressed in some but not all cells of the animal. The term "tissue-specific chimeric animal" indicates that one of the recombinant TRBP gene is present and/or expressed or disrupted in some tissues but not others.

The term "nuclear hormone receptor" used interchangeably herein with the terms "nuclear receptor" and "nuclear hormone-like receptor" refers broadly to protein or protein complexes which are cell surface receptors, which upon binding a ligand are internalized and migrate to the cell nucleus where they are involved in regulating transcription of target genes. Examples of nuclear hormone receptors include the members of the steroid/thyroid superfamily of receptors, including, but not limited to, glucocorticoid receptor (GR), mineralocorticoid receptor, progesterone receptor, estrogen receptor, estrogen-related receptors, vitamin D3 receptor, thyroid hormone receptor (TR), retinoic acid receptor (RAR), retinoic X receptor (RXR), aldosterone receptor, androgen receptor, and the like. The receptors of the steroid/thyroid superfamily have structurally dual functionally similar. A thyroid hormone receptor can be a TR-alpha or a TR-beta. Another nuclear hormone receptor is the hepatocyte nuclear factor 4 (HNF4).

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the term "promoter" means a DNA sequence that regulates expression of a selected DNA sequence operably linked to the promoter, and which effects expression of the selected DNA sequence in cells. The term encompasses "tissue specific" promoters, i.e. promoters, which effect expression of the selected DNA sequence only in specific cells (e.g. cells of a specific tissue). The term also covers so-called "leaky" promoters, which regulate expression of a selected DNA primarily in one tissue, but cause expression in other tissues as well. The term also encompasses non-tissue specific promoters and promoters that constitutively express or that are inducible (i.e. expression levels can be controlled).

The terms "protein", "polypeptide" and "peptide" are used interchangeably herein when referring to a gene product.

The term "recombinant protein" refers to a polypeptide of the present invention which is produced by recombinant DNA techniques, wherein generally, DNA encoding a TRBP polypeptide is inserted into a suitable expression vector which is in turn used to transform a host cell to produce the heterologous protein. Moreover, the phrase "derived from", with respect to a recombinant TRBP gene, is meant to include within the meaning of "recombinant protein" those proteins having an amino acid sequence of a native TRBP protein, or an amino acid sequence similar thereto which is generated by mutations including substitutions and deletions (including truncation) of a naturally occurring form of the protein.

"Small molecule" as used herein, is meant to refer to a composition, which has a molecular weight of less than about 5 kD and most preferably less than about 4 kD. Small molecules can be nucleic acids, peptides, polypeptides, peptidomimetics, carbohydrates, lipids or other organic (carbon containing) or inorganic molecules. Many pharmaceutical companies have extensive libraries of chemical and/or biological mixtures, often fungal, bacterial, or algal extracts, which can be screened with any of the assays of the invention.

As used herein, the term "specifically hybridizes" or "specifically detects" refers to the ability of a nucleic acid molecule of the invention to hybridize to at least approximately 6, 12, 20, 30, 50, 100, 150, 200, 300, 350, 400 or 425 consecutive nucleotides of a vertebrate, preferably a TRBP gene.

The term, "thyroid-related disorder or condition" refers to any disease, disorder or condition which is characterized by an abnormal thyroid-related activity. A thyroid-related disorder can be a metabolic disorder, e.g. catabolic disorder, a nervous system disorder, a disorder effecting the stature of an individual, thyroiditis, Hashimoto's thyroiditis, thyrotoxicosis, and Grave's disease. A thyroid-related disorder can be due to an abnormal processing of the thyroid hormones, e.g., abnormal intracellular signalling transmitted by a thyroid hormone receptor. For example, a thyroid-related disorder can result from an aberrant TRBP activity, e.g., a deficient interaction of a thyroid hormone receptor with a TRBP protein. A thyroid-related disorder can also result from aberrant TRBP protein levels in cells of a subject.

As used herein, the term "Thyroid hormone Receptor Binding Protein gene" or "TRBP gene" or "recombinant TRBP gene" refers to a nucleic acid molecule (e.g. genomic DNA) encoding a TRBP polypeptide of the present invention, including exon and (optionally) intron sequences. A "recombinant gene" refers to nucleic acid encoding a TRBP polypeptide and comprising TRBP-encoding exon sequence, though it may optionally include intron sequences which are either derived from a chromosomal TRBP gene or from an unrelated chromosomal gene. The term "intron" refers to a DNA sequence present in a given TRBP gene which is not translated into protein and is generally found between exons.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of one of the TRBP genes is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring forms of TRBP protein.

As used herein, the term "transfection" means the introduction of a nucleic acid, e.g., via an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of an TRBP polypeptide or, in the case of anti-sense expression from the transferred gene, the expression of a naturally-occurring form of the TRBP protein is disrupted.

As used herein, the term "transgene" means a nucleic acid sequence (encoding, e.g., one of the TRBP polypeptides, or an antisense transcript thereto) which has been introduced into a cell. A transgene could be partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can also be present in a cell in the form of an episome. A transgene can include one or more transcriptional regulatory sequences and any other nucleic acid, such as introns, that may be necessary for optimal expression of a selected nucleic acid.

A "transgenic animal" refers to any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of one of the TRBP protein, e.g. either agonistic or antagonistic forms. However, transgenic animals in which the recombinant TRBP gene is silent are also contemplated, as for example, the FLP or CRE recombinase dependent constructs described below. Moreover, "transgenic animal" also includes those recombinant animals in which gene disruption of one or more TRBP genes is caused by human intervention, including both recombination and antisense techniques.

The term "TRBP therapeutic" refers to various forms of TRBP polypeptides, as well as peptidomimetics, which can modulate at least one activity of a TRBP protein, e.g., binding to a thyroid hormone receptor (TR) in the presence or absence of thyroid hormone ($T_3$) or ($T_4$), by mimicking or potentiating (agonizing) or inhibiting (antagonizing) the effects of a naturally-occurring TRBP protein. A TRBP therapeutic which mimics or potentiates the activity of a wild-type TRBP protein is a "TRBP agonist". Conversely, a TRBP therapeutic which inhibits the activity of a wild-type TRBP protein is a "TRBP antagonist".

The terms "TRBP polypeptide" and "TRBP protein" are intended to encompass polypeptides comprising the amino acid sequence SEQ ID No. 2, fragments thereof, and homologs thereto and include agonist and antagonist polypeptides.

The term "treating" as used herein is intended to encompass curing as well as ameliorating at least one symptom of the condition or disease.

The term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

4.3 Nucleic Acids and Gene Therapeutics

Preferred nucleic acids of the invention are obtained from vertebrates. Particularly preferred vertebrate TRBP nucleic acids are mammalian. Regardless of species, particularly preferred TRBP nucleic acids encode polypeptides that are at least about 90% similar or identical to an amino acid sequence of a vertebrate TRBP. Preferred nucleic acids encode a TRBP polypeptide comprising an amino acid sequence, which is at least about 50%, 60%, 70%, 75%, 80%, 85%, 90%, or 95% homologous or identical to a sequence of SEQ ID No. 2. In an even more preferred embodiment, the nucleic acid of the invention encodes a TRBP polypeptide which is at least about 98% similar or identical to a sequence in SEQ ID No. 2, and even more preferably at least about 99% similar or identical to a sequence in SEQ ID No. 2. Most preferred nucleic acids encode a TRBP protein having an overall amino acid sequence homology or identity of at least about 90%, preferably at least about 92%, at least about 95%, at least about 98%, and even more preferably at least about 99% with the amino acid sequence set forth in SEQ ID No. 2.

Further preferred nucleic acids encode a protein comprising an N-terminal portion of the sequence SEQ ID No. 2. Preferred nucleic acids comprise an amino acid sequence of at least about 5, preferably at least about 7, at least about 10, at least about 12, at least about 15, at least about 17, at least about 18, at least about 19, and even more preferably at least about 20 consecutive amino acid residues located in an N-terminal portion of a TRBP protein, preferably between amino acid residue 1 and about amino acid residue 191 of SEQ ID No. 2. Particularly preferred nucleic acids encode a protein comprising at least about 5, preferably at least about 7, at least about 10, at least about 12, at least about 15, at least about 17, at least about 18, at least about 19, and even more preferably at least about 20 consecutive amino acids located between amino acid residue 1 and amino acid residue 191 of SEQ ID No. 2 and an amino acid sequence located downstream of residue 191 of SEQ ID No. 2.

Yet other preferred nucleic acids comprise a nucleic acid sequence encoding at least about 81 consecutive amino acids of SEQ ID No. 2. In an even more preferred embodiment, the nucleic acid encodes a protein comprising at least about 130, or at least about 172 consecutive amino acids of SEQ ID No. 2.

In another embodiment, the invention provides a nucleic acid encoding a TRBP polypeptide comprising an amino acid sequence which is at least about 70%, at least about 80%, at least about 85%, at least about 90%, at least about 95% and more preferably at least about 98% homologous or identical to a sequence of at least about 10, preferably at least about 12, at least about 15, at least about 17, at least about 20, and most preferably at least about 25 consecutive amino acid residues located in a portion of SEQ ID No. 2. A preferred portion of SEQ ID No. 2 is an N-terminal portion, preferably a portion from about amino acid residue 1 to about amino acid residue 191 of SEQ ID No. 2. Also within the scope of the invention are nucleic acids encoding a TRBP polypeptide comprising an amino acid sequence which is at least about 99% homologous or identical to at least about 126 consecutive amino acids of SEQ ID No. 2.

Even more preferred nucleic acid sequences encode a TRBP polypeptide having at least about 2, preferably at least about 3, at least about 5, at least about 7 or at least about 10 consecutive amino acids of SEQ ID No. 2, said nucleotide sequence not being present in the nucleic acid sequences having GenBank Accession Nos. F06909, L40387, AA115315, U49869, and D00068. Yet other preferred nucleic acid sequences encode a TRBP polypeptide having an amino acid sequence which is at least about 70%, at least about 80%, at least about 85%, at least about 90%, at least about 95%, at least about 98% or at least about 99% homologous or identical to the amino acid sequence of at least about 3, at least about 5, at least about 7, at least about 10, at least about 12, or at least about 15 consecutive amino acids of SEQ ID No. 2, said nucleotide sequence not being present in the nucleic acid sequences having GenBank Accession Nos. F06909, L40387, AA115315, U49869, and D00068.

In another embodiment, the invention provides nucleic acids comprising a nucleotide sequence from SEQ ID No. 1. Preferred nucleic acids comprise at least about 100 consecutive nucleotides, at least about 150 consecutive nucleotides, at least about 200 consecutive nucleotides, at least about 250 consecutive nucleotides, at least about 300 consecutive nucleotides, at least about 301, at least about 350 consecutive nucleotides, at least about 400 consecutive nucleotides, at least about 450 consecutive nucleotides, or at least about 500 consecutive nucleotides from SEQ ID No. 1. Also within the scope of the invention are nucleic acids comprising a sequence of at least about 6, at least about 9, at least about 12, at least about 15, at least about 18, or preferably at least about 20 or at least about 30 consecutive nucleic acid residues located in the 5' end of SEQ ID No. 1. Preferred nucleic acids comprise at least about 6, at least 9, at least 12, at least 15, at least 18, or preferably at least about 20 consecutive nucleic acid residues of the sequence from nucleotide 1 to about nucleotide 574 of SEQ ID No. 1. Other preferred nucleic acids comprise at least about 6, at least about 9, at least about 12, at least about 15, at least about 18, or preferably at least about 20 or at least about 30 consecutive nucleic acid residues in the sequence from nucleotide 1 to about nucleotide 574 of SEQ ID NO.1 and further comprise a nucleic acid sequence located downstream of about nucleotide 574.

Also within the scope of the invention are nucleic acids comprising at least about 30, at least about 40, at least about 50, at least about 53, at least about 60 or more preferably at least about 70 consecutive nucleotides from a 5' portion of a sequence having SEQ ID No. 1, preferably from about nucleotide 1 to about nucleotide 778 of SEQ ID No. 1.

Nucleic acids having a sequence that differs from the reported sequences due to degeneracy in the genetic code are also within the scope of the invention. Such nucleic acids encode functionally equivalent peptides (i.e., peptides having the same biological activity) but differ in sequence from the sequence shown in the sequence listing due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence of a polypeptide. However, it is expected that DNA sequence polymorphisms that do lead to changes in the amino acid sequences of the subject polypeptides will exist among mammalians. One skilled in the art will appreciate that these variations in one or more nucleotides (e.g., up to about 3–5% of the nucleotides) of the nucleic acids encoding polypeptides may exist among individuals of a given species due to natural allelic variation.

Other nucleic acids of the invention comprise a nucleotide sequence which is at least about 70%, at least about 75%, at least about 80%, at least about 85%, at least about 90%, at least about 95%, more preferably at least about 98%, and most preferably at least about 99% identical to SEQ ID No. 1 or a portion of SEQ ID No. 1. A portion can be nucleotides 1 to about nucleotides 574 or about 581 of SEQ ID No. 1. A portion can also be at least about 200, preferably at least about 250, at least about 300, at least about 350, at least about 378, or preferably at least about 400 consecutive nucleotides of SEQ ID No. 1.

Yet other preferred nucleic acids of the invention include nucleic acids encoding a TRBP protein having a biological activity, e.g, binding to a protein, e.g., the thyroid hormone receptor. In one example, preferred nucleic acids encode a TRBP protein comprising at least about 81 consecutive amino acids, or at least about 130 consecutive amino acids from SEQ ID No. 2. Assays for determining biological activity of a TRBP protein are described infra.

Also within the scope of the invention are nucleic acids corresponding essentially to exons of the TRBP gene. The intron/exon boundaries of the human TRBP gene comprising the nucleotide sequence set forth in SEQ ID No. 1 is shown in FIG. 4. The human TRBP gene comprises at least 7 exons, numbered from 1 to 7, and at least 6 introns, numbered 1 to 6. Exon 1 of the human TRBP gene comprises the nucleic acid sequence from about nucleotide 1 to about nucleotide 197 of SEQ ID No.1 (FIGS. 1 and 4). Exon 2 of the human TRBP gene has essentially the nucleotide sequence from about nucleotide 198 to about nucleotide 480 of SEQ ID No. (FIGS. 1 and 4). Exon 3 of the human TRBP gene has essentially the nucleotide sequence from about nucleotide 481 to about nucleotide 657 of SEQ ID No.1 (FIGS. 1 and 4). Exon 4 of the human TRBP gene has essentially the nucleotide sequence from about nucleotide 658 to about nucleotide 899 of SEQ ID No. 1 (FIGS. 1 and 4). Exon 5 of the human TRBP gene has essentially the sequence from about nucleotide 900 to about nucleotide 1047 of SEQ ID No. I FIGS. 1 and 4). Exon 6 of the human TRBP gene has essentially the sequence from about nucleotide 1048 to about nucleotide 1512 of SEQ ID No.1 (FIGS. 1 and 4). Exon 7 of the human TRBP gene comprises from about nucleotide 1513 to 1752 of SEQ ID No. 1 (FIGS. 1 and 4). Accordingly, any nucleic acid corresponding essentially to one or more exons from a TRBP gene, e.g., human TRBP, or comprising at least one exon of a TRBP gene, are within the scope of the invention.

A nucleic acid comprising the genomic sequence of human TRBP, containing the sequence shown in FIG. 4 has been deposited at the ATCC on Apr. 11, 1997 and has been assigned ATCC Designation No. 98407. This nucleic acid is in the form of a bacterial artificial chromosome (BAC) clone.

The TRBP gene or a portion thereof can be isolated form the BAC clone by methods known in the art. For example, the TRBP gene or a portion thereof can be isolated using restriction enzymes. A preferred method for isolating the TRBP gene or a portion thereof from the BAC clone is by polymerase chain reaction (PCR) using primers hybridizing to SEQ ID No. 1 or a sequence shown in FIG. 4. In one embodiment, a nucleic acid containing the exons of the human TRBP gene is prepared by PCR reactions amplifying each of the exons of the TRBP gene in the BAC clone or other genomic DNA ligation of the amplified nucleic acids. The nucleic acid can then be sequenced to confirm correct ligation of the exons. Alternatively, a cDNA encoding TRBP can be isolated by screening a cDNA library using a probe having a sequence from SEQ ID No. 1 or by RT-PCR (reverse transcribed PCR) amplification of mRNA from cells expressing TRBP, e.g., HeLa cells using primers hybridizing to a nucleic acid having a sequence set forth in SEQ ID No. 1.

Also within the scope of the invention are nucleic acids corresponding essentially to an intron or fragment thereof of a TRBP gene. Yet other nucleic acids within the scope of the invention comprise at least a portion of an intronic sequence from a TRBP gene, e.g, human TRBP. A portion can be at least about 6 nucleotides, preferably at least about 9, at least about 12, at least about 15, at least about 18, or even more preferably at least about 20 nucleotides. Nucleotide sequences of portions of introns from the human TRBP gene are shown, e.g., in FIG. 4. In one embodiment, nucleic acid probes comprising a portion of an intronic sequence from a TRBP gene are used, e.g,. in diagnostic methods, in which one desires to detect only the gene itself or one or more introns thereof.

Preferred nucleic acids of the invention comprise a nucleic acid sequence which is at least about 70%, at least about 75%, at least about 80%, at least about 85%, at least about 90%, at least about 95%, or at least about 98% homologous to a nucleic acid sequence of SEQ ID No. 1 or any of the above-cited nucleic acids. Preferred nucleic acids have an overall nucleotide sequence homology of at least about 90%, preferably at least about 92%, at least about 95%, at least about 98%, and even more preferably at least about 99% identity with the sequence set forth in SEQ ID No. 1.

Appropriate stringency conditions for identifying homologs of known genes, for example, 6.0×sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1–6.3.6. For example, the salt concentration in the wash step can be selected from a low stringency of about 2.0×SSC at 50° C to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. Nucleic acids can be obtained from mRNA present in any of a number of eukaryotic cells. It should also be possible to obtain nucleic acids of the present invention from genomic DNA from both adults and embryos. For example, a gene can be cloned from either a cDNA or a genomic library in accordance with protocols described herein, as well as those generally known to persons skilled in the art. Examples of tissues and/or libraries suitable for isolation of the subject nucleic acids include epithelial cells. A cDNA can be obtained by isolating total mRNA from a cell, e.g. a vertebrate cell, a mammalian cell, or a human cell, including embryonic cells. Double stranded cDNAs can then be prepared from the total mRNA, and subsequently inserted into a suitable plasmid or bacteriophage vector using any one of a number of known techniques. The gene encoding a protein can also be cloned using established polymerase chain reaction techniques in accordance with the nucleotide sequence information provided by the invention. The nucleic acid of the invention can be DNA or RNA For gene therapy, preferably the gene is administered to a subject in an expression vector, i.e. a nucleic acid encoding a polypeptide, operably linked to at least one transcriptional regulatory sequence. "Operably linked" is intended to mean that the nucleotide sequence is linked to a regulatory sequence in a manner which allows expression of the nucleotide sequence. Regulatory sequences are art-recognized and are selected to direct expression of the subject proteins. Accordingly, the term "transcriptional regulatory sequence" includes promoters, enhancers and other expression control elements. Such regulatory sequences are described in Goeddel; *Gene Expression Technology: Methods in Enzymology* 185, Academic Press, San Diego, Calif. (1990). In one embodiment, the expression vector includes a recombinant gene encoding a peptide having an agonistic activity of a TRBP polypeptide, or alternatively, encoding a peptide which is an antagonistic form of a TRBP polypeptide. Such expression vectors can be used to transfect cells and thereby produce polypeptides, including fusion proteins, encoded by nucleic acids as described herein. Moreover, the gene constructs of the present invention can also be used as a part of a gene therapy protocol to deliver nucleic acids encoding either an agonistic or antagonistic form of one of the subject TRBP proteins. Thus, the invention features expression vectors for in vivo or in vitro transfection and expression of a TRBP polypeptide, in particular for expression of a TRBP polypeptide in cells so as to reconstitute the function of, or alternatively, abrogate the function of a TRBP protein. This could be desirable, for example, when the naturally-occurring form of the protein is misexpressed; or to deliver a form of the protein which alters transcription of target genes in a tissue.

The invention also provides for a specific combination of nucleic acid sequences, which can be used for example in prognostic and diagnostic methods. Preferred combinations of primers for analyzing genomic DNA are comprised of a nucleic acid sequence, which is located at an intron/exon boundary of the gene, (see e.g., in FIG. 4 and the Examples). In assays involving genomic DNA, one can also use a primer corresponding to a region located in an intron and having, e.g, a sequence shown in FIG. 4. Other preferred combinations of primers comprise at least one primer corresponding to a region located between nucleotides 1 and about nucleotide 574 of SEQ ID No. 1.

4.4. TRBP Proteins and Protein Therapeutics

The invention provides isolated naturally occurring TRBP proteins as well as recombinantly produced or synthetic TRBP proteins.

Preferred TRBP proteins comprise an amino acid sequence from SEQ ID No. 2. Yet other preferred TRBP proteins are those which are encoded by any of the nucleic acid molecules described in the above-section drawn to "Nucleic Acids and Gene Therapeutics". For example, proteins comprising one or more particular motifs and/or domains or to arbitrary sizes, for example, at least 5, 10, 25, 50, 75, 100, 125, 150 amino acids in length are within the scope of the present invention.

In one embodiment the invention provides a TRBP polypeptide comprising a domain mediating the interaction with another molecule, such as a protein. The TRBP domain involved in binding to the thyroid hormone receptor is likely to involve the region between about amino acid 260 and about amino acid 416 of SEQ ID No. 2. In fact, this region contains the homology to TRIP14, which has been shown to bind to the thyroid hormone receptor β1 Wee et al. (1995) Endocrinology 9:243).

In addition, as described herein, TRBP has an overall amino acid sequence homology with the 2,5A oligoadenylate synthase, a protein capable of binding ATP and double stranded (ds) RNA. Accordingly, TRBP is likely to contain an ATP-binding domain and a domain capable of binding to ds RNA. Determination of the minimum portion of TRBP that is necessary for binding to another molecule, such as a thyroid hormone receptor, can be determined by, e.g., binding assays of TRBP deletion mutants. Such assays are further described herein. TRBP may also comprise a transcriptional activation or repression domain, a DNA binding domain, and additional domains interacting with other proteins, such as domains interacting with phosphorylated residues on another protein. Such domains can be identified by, e.g. analysis of deletion mutants and screening for a specific activity, e.g., transcriptional activity.

Accordingly, the invention provides TRBP polypeptides comprising a domain of a TRBP polypeptide having SEQ ID No. 2 or a homolog thereof Preferred TRBP polypeptides comprise at least a domain necessary for interaction with another molecule, e.g. protein. A preferred TRBP polypeptide of the invention comprises an amino acid sequence having at least a portion of SEQ ID No. 2 necessary for binding to a thyroid hormone receptor, e.g. about amino acid residue 260 to about amino acid residue 416 of SEQ ID No. 2.

The present invention also makes available isolated TRBP polypeptides, which are isolated from, or otherwise substantially free of other cellular proteins, especially other signal transduction factors and/or transcription factors which may normally be associated with the subject polypeptide. The term "substantially free of other cellular proteins" (also referred to herein as "contaminating proteins") or "substantially pure or purified preparations" are defined as encompassing preparations of polypeptides having less than about 20% (by dry weight) contaminating protein, and preferably having less than about 5% contaminating protein.

Functional forms of the subject polypeptides can be prepared, for the first time, as purified preparations by using a cloned gene as described herein. By "purified", it is meant, when referring to a peptide or DNA or RNA sequence, that the indicated molecule is present in the substantial absence of other biological macromolecules, such as other proteins. The term "purified" as used herein preferably means at least 80% by dry weight, more preferably in the range of 95–99% by weight, and most preferably at least about 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" do not encompass either natural materials in their native state or natural materials that have been separated into components (e.g., in an acrylamide gel) but not obtained either as pure (e.g. lacking contaminating proteins, or chromatography reagents such as denaturing agents and polymers, e.g. acrylamide or agarose) substances or solutions. In preferred embodiments, purified preparations will lack any contaminating proteins from the same animal from which the subject polypeptide is normally produced, as can be accomplished by recombinant expression of, for example, a human protein in a non-human cell.

Isolated peptidyl portions of TRBP proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a polypeptide of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a wild-type (e.g., "functional") or mutant TRBP protein.

According to the present invention, a polypeptide has biological activity if it is a specific agonist or antagonist. For example, a polypeptide agonist can effect increased expression of a functional TRBP gene; and/or increased activity of a functional TRBP protein. Further, a polypeptide antagonist can effect decreased expression of a functional or mutant TRBP gene or decreased activity of a functional or mutant TRBP protein.

The present invention further pertains to methods of producing the subject polypeptides. For example, a host cell transfected with a nucleic acid vector directing expression of a nucleotide sequence encoding the subject polypeptides can be cultured under appropriate conditions to allow expression of the peptide to occur. The cells may be harvested, lysed and the protein isolated. A cell culture includes host cells, media and other byproducts. Suitable media for cell culture are well known in the art. The recombinant polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant polypeptide is a fusion protein containing a domain which facilitates its purification, such as GST fusion protein or poly(His) fusion protein.

Moreover, it will be generally appreciated that, under certain circumstances, it may be advantageous to provide homologs of one of the subject TRBP polypeptides, which function in a limited capacity as one of either an agonist (mimetic) or an antagonist, in order to promote or inhibit only a subset of the biological activities of the naturally-occurring form of the protein. Thus, specific biological effects can be elicited by treatment with a homolog of limited function, and with fewer side effects relative to treatment with agonists or antagonists which are directed to all of the biological activities of naturally occurring forms of TRBP proteins.

Homologs of each of the subject proteins can be generated by mutagenesis, such as by discrete point mutation(s), or by truncation. For instance, mutation can give rise to homologs which retain substantially the same, or merely a subset, of the biological activity of the polypeptide from which it was derived. Alternatively, antagonistic forms of the protein can be generated which are able to inhibit the function of the naturally occurring form of the protein, such as by competitively binding to a downstream or upstream member of the biochemical pathway, which includes the TRBP protein. In addition, agonistic forms of the protein may be generated which are constitutively active. Thus, the TRBP protein and a homologs thereof, as provided herein may be either positive or negative regulators of gene expression.

The recombinant polypeptides of the present invention also include homologs of TRBP which are resistant to proteolytic cleavage, as for example, due to mutations which alter ubiquitination or other enzymatic targeting associated with the protein.

Polypeptide agonists or antagonists as discussed herein may also be chemically modified to create derivatives by forming covalent or aggregate conjugates with other chemical moieties, such as glycosyl groups, lipids, phosphate, acetyl groups and the like. Covalent derivatives of proteins can be prepared by linking the chemical moieties to functional groups on amino acid sidechains of the protein or at the N-terminus or at the C-terminus of the polypeptide.

Modification of the structure of the subject polypeptides can be for such purposes as enhancing therapeutic or prophylactic efficacy, stability (e.g., ex vivo shelf life and resistance to proteolytic degradation in vivo), or post-translational modifications (e.g., to alter phosphorylation pattern of protein). Such modified peptides, when designed to retain at least one activity of the naturally-occurring form of the protein, or to produce specific antagonists thereof, are considered functional equivalents of the polypeptides described in more detail herein. Such modified peptides can be produced, for instance, by amino acid substitution, deletion, or addition.

For example, it is reasonable to expect that an isolated replacement of a leucine with an isoleucine or valine, an aspartate with a glutamate, a threonine with a serine, or a similar replacement of an amino acid with a structurally related amino acid (i.e. isosteric and/or isoelectric mutations) will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be A grouped separately as aliphatic-hydroxyl; (4) aromatic=phenylalanine, tyrosine, tryptophan; (5) amide=asparagine, glutamine; and (6) sulfur-containing=cysteine and methionine. (see, for example, *Biochemistry*, 2nd ed., Ed. by L. Stryer, W H Freeman and Co.: 1981). Whether a change in the amino acid sequence of a peptide results in a functional homolog (e.g. functional in the sense that the resulting polypeptide mimics or antagonizes the wild-type form) can be readily determined by assessing the ability of the variant peptide to produce a response in cells in a fashion similar to the wild-type protein, or competitively inhibit such a response. Polypeptides in which more than one replacement has taken place can readily be tested in the same manner.

This invention further contemplates a method for generating sets of combinatorial mutants of the subject agonist or antagonist polypeptides as well as truncation mutants, and is especially useful for identifying potential variant sequences (e.g. homologs) that are functional in modulating TRBP activity. The purpose of screening such combinatorial libraries is to generate, for example, novel compounds which can act as either agonists or antagonist, comprise some, but not all TRBP activities, or alternatively, compounds which possess novel activities all together.

In one embodiment, the variegated library of variants is generated by combinatorial mutagenesis at the nucleic acid level, and is encoded by a variegated gene library. For instance, a mixture of synthetic oligonucleotides can be enzymatically ligated into gene sequences such that the degenerate set of potential sequences are expressible as individual polypeptides, or alternatively, as a set of larger fusion proteins (e.g. for phage display) containing the set of sequences therein.

There are many ways by which such libraries of potential TRBP homologs can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential sequences. The synthesis of degenerate oligonucleotides is well known in the art (see for example, Narang, S A (1983) *Tetrahedron* 39:3; Itakura et al. (1981) *Recombinant DNA, Proc 3rd Cleveland Sympos. Macromolecules*, ed. A. G. Walton, Amsterdam: Elsevier pp273–289; Itakura et al. (1984) *Annu. Rev. Biochem.* 53:323; Itakura et al. (1984) *Science* 198:1056; Ike et al. (1983) *Nucleic Acid Res.* 11:477). Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249:404–406; Cwirla et al. (1990) *PNAS* 87:6378–6382; as well as U.S. Pat. Nos. 5,223,409, 5,198,346, and 5,096,815).

Likewise, a library of coding sequence fragments can be provided for a clone in order to generate a variegated population of fragments for screening and subsequent selection of bioactive fragments. A variety of techniques are known in the art for generating such libraries, including chemical synthesis. In one embodiment, a library of coding sequence fragments can be generated by (i) treating a double stranded PCR fragment of a coding sequence with a nuclease under conditions wherein nicking occurs only about once per molecule; (ii) denaturing the double stranded DNA; (iii) renaturing the DNA to form double stranded DNA which can include sense/antisense pairs from different nicked products; (iv) removing single stranded portions from reformed duplexes by treatment with S1 nuclease; and (v) ligating the resulting fragment library into an expression vector. By this exemplary method, an expression library can be derived which codes for N-terminal, C-terminal and internal fragments of various sizes.

A wide range of techniques are known in the art for screening gene products of combinatorial libraries made by point mutations or truncation, and for screening cDNA libraries for gene products having a certain property. Such techniques will be generally adaptable for rapid screening of the gene libraries generated by the combinatorial mutagenesis of TRBP homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

Combinatorial mutagenesis has a potential to generate very large libraries of mutant proteins, e.g., in the order of $10^{26}$ molecules. Combinatorial libraries of this size may be technically challenging to screen even with high throughput screening assays. To overcome this problem, a new technique has been developed recently, recrusive ensemble mutagenesis (REM), which allows one to avoid the very high proportion of non-functional proteins in a random library and simply enhances the frequency of functional proteins, thus decreasing the complexity required to achieve a useful sampling of sequence space. REM is an algorithm which enhances the frequency of functional mutants in a library when an appropriate selection or screening method is employed (Arkin and Yourvan, 1992, *PNAS USA* 89:7811–7815; Yourvan et al., 1992, *Parallel Problem Solving from Nature*, 2., In Maenner and Manderick, eds., Elsevir Publishing Co., Amsterdam, pp. 401–410; Delgrave et al., 1993, *Protein Engineering* 6(3):327–331).

The invention also provides for reduction of the agonist or antagonist proteins to generate mimetics, e.g. peptide or non-peptide agents, which are able to modulate at least one activity of TRBP, such as disrupting binding of a TRBP polypeptide to another protein, such as the thyroid hormone receptor. Thus, such mutagenic techniques as described above are also useful to map the determinants of the proteins which participate in protein—protein interactions involved in, for example, binding of the subject polypeptides to proteins which may function upstream (including both activators (enhancers) and repressors of its activity) or to proteins and/or nucleic acids which may function downstream of the polypeptides, whether they are positively or negatively regulated by it. To illustrate, the critical residues of a subject polypeptide which are involved in molecular recognition of a component upstream or downstream of a TRBP protein can be determined and used to generate peptidomimetics which competitively inhibit binding of the authentic protein with that moiety. By employing, for example, scanning mutagenesis to map the amino acid residues of each of the subject proteins which are involved in binding other extracellular proteins, peptidomimetic compounds can be generated which mimic those residues of the protein which facilitate the interaction. Such mimetics may then be used to interfere with the normal function of a protein. For instance, non-hydrolyzable peptide analogs of such residues can be generated using benzodiazepine (e.g., see Freidinger et al. in *Peptides: Chemistry and Biology*, G. R. Marshall ed., ESCOM Publisher: Leiden, Netherlands, 1988), azepine (e.g., see Huffman et al. in *Peptides: Chemistry and Biology*, G. R. Marshall ed., ESCOM Publisher: Leiden, Netherlands, 1988), substituted gamma lactam rings (Garvey et al. in *Peptides: Chemistry and Biology*, G. R. Marshall ed., ESCOM Publisher: Leiden, Netherlands, 1988), keto-methylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill., 1985), β-turn dipeptide cores (Nagai et al. (1985) *Tetrahedron Lett* 26:647; and Sato et al. (1986) *J Chem Soc Perkin Trans* 1:1231), and β-aminoalcohols (Gordon et al. (1985) *Biochem Biophys Res Commun* 126:419; and Dann et al. (1986) *Biochem Biophys Res Commun* 134:71).

This invention also pertains to a host cell transfected to express a recombinant form of the subject polypeptides. The host cell may be any prokaryotic or eukaryotic cell. Thus, a nucleotide sequence derived from the cloning of vertebrate proteins, encoding all or a selected portion of the full-length protein, can be used to produce a recombinant form of a polypeptide via microbial or eukaryotic cellular processes. Ligating the polynucleotide sequence into a gene construct, such as an expression vector, and transforming or A transfecting into hosts, either eukaryotic (yeast, avian, insect or mammalian) or prokaryotic (bacterial cells), are standard procedures used in producing other well-known proteins, e.g. MAP kinase, p53, WT1, PTP phosphotases, SRC, and the like. Similar procedures, or modifications thereof, can be employed to prepare recombinant polypeptides by microbial means or tissue-culture technology in accord with the subject invention.

The recombinant gene products can be produced by ligating a nucleic acid encoding a protein, or a portion thereof, into a vector suitable for expression in either prokaryotic cells, eukaryotic cells, or both. Expression vectors for production of recombinant forms of the subject polypeptides include plasmids and other vectors. For instance, suitable vectors for the expression of a polypeptide include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al. (1983) in *Experimental Manipulation of Gene Expression*, ed. M. Inouye Academic Press, p. 83, incorporated by reference herein). These vectors can replicate in *E. coli* due the presence of the pBR322 ori, and in *S. cerevisiae* due to the replication determinant of the yeast 2 micron plasmid. In addition, drug resistance markers such as ampicillin can be used. In an illustrative embodiment, TRBP polypeptide is produced recombinantly utilizing an expression vector generated by sub-cloning the coding sequence of TRBP gene.

The preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press: 1989) Chapters 16 and 17.

In addition to viral transfer methods, such as those illustrated above, non-viral methods can also be employed to cause expression of a subject polypeptide in the tissue of an animal. Most nonviral methods of gene transfer rely on normal mechanisms used by mammalian cells for the uptake and intracellular transport of macromolecules. In preferred embodiments, non-viral targeting means of the present invention rely on endocytic pathways for the uptake of the subject gene by the targeted cell. Exemplary targeting means of this type include liposomal derived systems, poly-lysine conjugates, and artificial viral envelopes.

In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

When it is desirable to express only a portion of a protein, such as a form lacking a portion of the N-terminus, i.e. a truncation mutant which lacks the signal peptide, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al. (1987) *J. Bacteriol.* 169:751–757) and *Salmonella typhimurium* and its in vitro activity has been demonstrated on recombinant proteins (Miller et al. (1987) *PNAS* 84:2718–1722). Therefore, removal of an N-terminal methionine, if desired, can be achieved either in vivo by expressing polypeptides in a host which produces MAP (e.g., *E. coli* or CM89 or *S. cerevisiae*), or in vitro by use of purified MAP (e.g., procedure of Miller et al., supra).

In other embodiments transgenic animals, described in more detail below could be used to produce recombinant proteins.

In another embodiment, the coding sequences for the polypeptide can be incorporated as a part of a fusion gene including a nucleotide sequence encoding a different polypeptide. This type of expression system can be useful under conditions where it is desirable to produce an immunogenic fragment of a protein. For example, the VP6 capsid protein of rotavirus can be used as an immunologic carrier protein for portions of the polypeptide, either in the monomeric form or in the form of a viral particle. The nucleic acid sequences corresponding to the portion of a subject protein to which antibodies are to be raised can be incorporated into a fusion gene construct which includes coding sequences for a late vaccinia virus structural protein to produce a set of recombinant viruses expressing fusion proteins comprising epitopes as part of the virion. It has been demonstrated with the use of immunogenic fusion proteins utilizing the Hepatitis B surface antigen fusion proteins that recombinant Hepatitis B virions can be utilized in this role as well. Similarly, chimeric constructs coding for fusion proteins containing a portion of an agonist or antagonist protein and the poliovirus capsid protein can be created to enhance immunogenicity of the set of polypeptide antigens (see, for example, EP Publication No: 0259149; and Evans et al. (1989) Nature 339:385; Huang et al. (1988) J. Virol. 62:3855; and Schlienger et al. (1992) *J. Virol.* 66:2).

The Multiple Antigen Peptide system for peptide-based immunization can also be utilized to generate an immunogen, wherein a desired portion of a polypeptide is obtained directly from organo-chemical synthesis of the peptide onto an oligomeric branching lysine core (see, for example, Posnett et al. (1988) *JBC* 263:1719 and Nardelli et al. (1992) *J. Immunol.* 148:914). Antigenic determinants of proteins can also be expressed and presented by bacterial cells.

In addition to utilizing fusion proteins to enhance immunogenicity, it is widely appreciated that fusion proteins can also facilitate the expression of proteins, and accordingly, can be used in the expression of the polypeptides of the present invention. For example, agonist or antagonist polypeptides can be generated as glutathione-S-transferase (GST-fusion) proteins. Such GST-fusion proteins can enable easy purification of the agonist or antagonist polypeptide, as for example by the use of glutathione-derivatized matrices (see, for example, *Current Protocols in Molecular Biology*, eds. Ausubel et al. (N.Y.: John Wiley & Sons, 1991)). Such fusion proteins can also be used to isolate proteins which interact with TRBP. For example, a cell extract can be poured over an affinity column containing a TRBP fusion protein and the proteins binding to the column can then be eluted and identified.

In another embodiment, a fusion gene coding for a purification leader sequence, such as a poly-(His)/enterolinase cleavage site sequence at the N-terminus of the desired portion of the recombinant protein, can allow purification of the expressed fusion protein by affinity chromatography using a Ni2+ metal resin. The purification leader sequence can then be subsequently removed by treatment with enterokinase to provide the purified protein (e.g., see Hochuli et al. (1987) *J. Chromatography* 411:177; and Janknecht et al. *PNAS* 88:8972).

Techniques for making fusion genes are known to those skilled in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al. John Wiley & Sons: 1992).

4.5 Antisense, Ribozyme and Triplex Therapeutics

Another aspect of the invention relates to nucleic acids that are effective antisense, ribozyme and triplex antagonists of mutant or otherwise defective (e.g overexpressed) TRBP nucleic acids. As used herein, "antisense" therapy refers to administration or in situ generation of oligonucleotide molecules or their derivatives which specifically hybridize (e.g. bind) under cellular conditions, with the cellular mRNA and/or genomic DNA encoding one or more of the subject proteins so as to inhibit expression of that protein, e.g. by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes a functional TRBP protein. Alternatively, the antisense construct is an oligonucleotide probe which is generated ex vivo and which, when introduced into the cell causes inhibition of expression by hybridizing with the mRNA and/or genomic sequences of a TRBP gene.

Antisense molecules of the invention can be any nucleic acid or complement thereof described in the section entitled "Nucleic Acids and Gene Therapeutics". Antisense molecules within the scope of the invention can also be nucleic acids hybridizing to a portion of (a) a nucleic acid encoding a protein which regulates expression of a TRBP gene; (b) a gene whose expression is regulated by TRBP; or (c) a gene encoding a protein interacting with TRBP.

Such oligonucleotide probes are preferably modified oligonucleotides which are resistant to endogenous nucleases, e.g. exonucleases and/or endonucleases, and are therefore stable in vivo. Exemplary nucleic acid molecules for use as antisense oligonucleotides are phosphoramidate, phosphorothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) *Biotechniques* 6:958–976; and Stein et al. (1988) *Cancer Res* 48:2659–2668. With respect to antisense DNA, oligodeoxyribonucleotides derived from the translation initiation site, e.g., between the −10 and +10 regions of the TRBP translation initiation site are preferred.

Antisense approaches involve the design of oligonucleotides (either DNA or RNA) that are complementary to TRBP mRNA or mRNA of gene whose expression is modulated by TRBP or genes encoding proteins which interact with TRBP. The antisense oligonucleotides will bind to the mRNA transcript (e.g. a mutant transcript) and prevent translation. Absolute complementarity, although preferred, is not required. A sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides complementary to either the 5' or 3' untranslated, non-coding regions of a gene, e.g. TRBP gene can be used in an antisense approach to inhibit translation of endogenous mRNA, e.g. TRBP mRNA- Whether designed to hybridize to the 5', 3' or coding region of an mRNA, antisense nucleic acids should be at least six nucleotides in length, and are preferably oligonucleotides ranging from 6 to about 50 nucleotides in lengths In certain embodiments, the oligonucleotide is at least about 10 nucleotides, at least about 17 nucleotides, at least about 25 nucleotides, or at least about 50 nucleotides long.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, *Proc. Natl. Acad. Sci.* U.S.A. 86:6553–6556; Lemaitre et al., 1987, *Proc. Natl. Acad Sci.* 84:648–652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., 1988, BioTechniques 6:958–976) or intercalating agents. (See, e.g., Zon, 1988, *Pharm. Res.* 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5- oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

The antisense oligonucleotide can also contain a neutral peptide-like backbone. Such molecules are termed peptide nucleic acid (PNA)-oligomers and are described, e.g., in Perry-O'Keefe et al. (1996) Proc. Natl. Acad. Sci. U.S.A. 93:14670 and in Eglom et al. (1993) Nature 365:566. One advantage of PNA oligomers is their capability to bind to complementary DNA essentially independently from the ionic strength of the medium due to the neutral backbone of the DNA. In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, *Nucl. Acids Res.* 15:6625–6641). The oligonucleotide is a 2'-0-methylribonucleotide (Inoue et al., 1987, *Nucl. Acids Res.* 15:6131–6148), or a chimeric RNA-DNA analogue (Inoue et al., 1987, *FEBS Lett.* 215:327–330).

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, *Nucl. Acids Res.* 16:3209), methylphosphonate oligonucleotides can be prepared by use of controlled pore glass polymer supports (Sarin et al., 1988, *Proc. Natl. Acad. Sci. U.S.A.* 85:7448–7451), etc.

A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

A preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous transcript and thereby prevent translation of the mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA- Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, *Nature* 290:304–310), the promoter contained in the 3' long terminal repeat of Rous sarcoma virus (Yamamoto et al., 1980, *Cell* 22:787–797), the herpes thymidine kinase promoter (Wagner et al., 1981, *Proc. Natl. Acad Sci.* U.S.A 78:1441–1445), the regulatory sequences of the metallothionein gene (Brinster et al, 1982, *Nature* 296:39–42), etc. Any type of plasmid, cosmid, YAC or viral vector can be used to prepare the recombinant DNA construct which can be introduced directly into the tissue site. Alternatively, viral vectors can be used which selectively infect the desired tissue; (e.g., for brain, herpes virus vectors may be used), in which case administration may be accomplished by another route (e.g., systematically).

The invention further provides ribozymes for regulating a TRBP activity. Ribozymes are enzymatic RNA molecules capable of catalyzing the specific cleavage of RNA. The mechanism of ribozyme action involves sequence specific hybridization of the ribozyme molecule to complementary target RNA, followed by an endonucleolytic cleavage. The composition of ribozyme molecules must include one or more sequences complementary to the target gene mRNA, and must include the well known catalytic sequence responsible for mRNA cleavage. For this sequence, see U.S. Pat. No. 5,093,246, which is incorporated by reference herein in its entirety. As such within the scope of the invention are engineered hammerhead motif ribozyme molecules that specifically and efficiently catalyze endonucleolytic cleavage of RNA sequences encoding agonist or antagonist proteins (further described herein).

Specific ribozyme cleavage sites within any potential RNA target are initially identified by scanning the molecule of interest for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features, such as secondary structure, that may render the oligonucleotide sequence unsuitable. The suitability of candidate sequences may also be evaluated by testing their accessibility to hybridization with complementary oligonucleotides, using ribonuclease protection assays.

Ribozyme molecules are described in PCT International Publication WO90/11364, published Oct. 4, 1990; Sarver et al., 1990, and Science 247:1222–1225. While ribozymes that cleave mRNA at site specific recognition sequences can be used to destroy mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, *Nature*, 334:585–591. There are typically hundreds of potential hammerhead ribozyme cleavage sites within the nucleotide sequence of a gene, e.g. TRBP gene. Preferably the ribozyme is engineered so that the cleavage recognition site is located near the 5' end of the mRNA; i.e., to increase efficiency and minimize the intracellular accumulation of non-functional mRNA transcripts.

The ribozymes of the present invention also include RNA endoribonucleases (hereinafter "Cech-type ribozymes") such as the one which occurs naturally in *Tetrahymena thermophila* (known as the IVS, or L-19 IVS RNA) and which has been extensively described by Thomas Cech and collaborators (Zaug, et al., 1984, *Science*, 224:574–578; Zaug and Cech, 1986, *Science*, 231:470–475; Zaug, et al., 1986, *Nature*, 324:429–433; published International patent application No. WO88/04300 by University Patents Inc.; Been and Cech, 1986, *Cell*, 47:207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in a gene.

As in the antisense approach, the ribozymes can be composed of modified oligonucleotides (e.g. for improved stability, targeting, etc.) and should be delivered to cells which express the gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous TRBP messages and inhibit translation. Because ribozymes unlike antisense molecules, are catalytic, a lower intracellular concentration is required for efficiency.

Endogenous mutant TRBP gene expression can also be reduced by inactivating or "knocking out" the TRBP gene or its promoter using targeted homologous recombination. (e.g., see Smithies et al., 1985, *Nature* 317:230–234; Thomas & Capecchi, 1987, *Cell* 51:503–512; Thompson et al., 1989 *Cell* 5:313–321; each of which is incorporated by reference herein in its entirety). For example, a wildtype, functional TRBP (or a completely unrelated DNA sequence) flanked by DNA homologous to the endogenous mutant TRBP gene (either the coding regions or regulatory regions of the TRBP gene) can be used, with or without a selectable marker and/or a negative selectable marker, to transfect cells that express mutant TRBP in vivo. Insertion of the DNA construct, via targeted homologous recombination, results in inactivation of the mutant TRBP gene. Such approaches are particularly suited for generating transgenic animals, where modifications to ES (embryonic stem) cells can be used to generate animal offspring with an inactive TRBP e.g., see Thomas & Capecchi 1987 and Thompson 1989, supra). However this approach can be adapted for use in humans provided the recombinant DNA constructs are directly administered or targeted to the required site in vivo using appropriate viral vectors, e.g., herpes virus vectors for delivery to brain tissue.

Alternatively, endogenous (mutant or wildtype) gene expression can be reduced by targeting deoxyribonucleotide sequences complementary to the regulatory region of the gene (i.e., the promoter and/or enhancers) to form triple helical structures that prevent transcription of the gene in target cells in the body. (See generally, Helene, C. 1991, *Anticancer Drug Des.*, 6(6):569–84; Helene, C., et al., 1992, *Ann, N.Y. Accad. Sci.*, 660:27–36; and Maher, L. J., 1992, *Bioassays* 14(12):807–15).

Nucleic acid molecules to be used in triple helix formation for the inhibition of transcription are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

Antisense RNA and DNA, ribozyme, and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

4.6 Antibody Therapeutics

Another aspect of the invention pertains to antibodies or antigen binding agents, which are specifically reactive with a TRBP protein. The term "TRBP binding agent" as used herein, refers to an agent, e.g., a protein which interacts specifically with a TRBP protein. Preferred TRBP binding agents are antibodies or derivatives thereof, which are further described infra. TRBP binding agents can be used, e.g., for treating or preventing a disease caused by, or contributed to by an aberrant TRBP activity in a subject, by administering to the subject an effective amount of a TRBP binding agent or nucleic acid encoding a TRBP binding agent. For example, a TRBP binding agent can inhibit at least partly an aberrant activity of a mutated or overexpressed TRBP protein. Also within the scope of the invention are TRBP binding agents which are capable of interacting specifically with a mutated form of a TRBP protein. Preferably the antibody or TRBP binding agent is administered in a delivery complex or in conjunction with an agent that allows entry of the antibody into cell nuclei. Alternatively, it can be produced in the target cell.

In another embodiment, a TRBP binding agent is used as a target molecule. For example, a TRBP binding agent can be linked to cytotoxic molecule, such as to lyse a cell expressing or overexpressing TRBP or a mutated form thereof In yet another embodiment, a TRBP binding agent is used as a prognostic or diagnostic agent. For example, a TRBP binding agent can be used to determine the amount of TRBP or mutated TRBP in a subject. In one embodiment, the amount of TRBP protein or mutated TRBP protein is determined in vivo. Alternatively, the amount of TRBP protein or mutated protein is determined in a tissue sample that is obtained from the subject. In a specific embodiment, a TRBP binding agent is linked to a marker protein for detecting a TRBP protein or determining its protein level.

Various methods can be used to produce TRBP binding agents. For example, by using immunogens derived from a TRBP protein, anti-protein/anti-peptide antisera or monoclonal antibodies can be made by standard protocols (See, for example, *Antibodies: A Laboratory Manual* ed. by Harlow and Lane (Cold Spring Harbor Press: 1988)). A mammal, such as a mouse, a hamster or rabbit can be immunized with an immunogenic form of the peptide. Techniques for conferring immunogenicity on a protein or peptide include conjugation to carriers or other techniques well known in the art. An immunogenic portion of an agonist or antagonist protein can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of a TRBP protein of a mammal, e.g. antigenic determinants of a protein represented in Bach, I. et al., (1990) *Genomics* 8:155–164 or closely related homologs (e.g. at least 92% homologous, and more preferably at least 94% homologous).

Following immunization of an animal with an antigenic preparation of an agonist or antagonist polypeptide, antisera can be obtained and, if desired, polyclonal antibodies isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) *Nature*, 256:495–497), the human B cell hybridoma technique (Kozbar et al., (1983) *Immunology Today*, 4:72), and the EBV-hybridoma technique to produce human monoclonal antibodies (Cole et al., (1985) *Monoclonal Antibodies and Cancer Therapy*, Alan R Liss, Inc. pp. 77–96). Hybridoma cells can be screened immunochemically for production of antibodies specifically reactive with an agonist or antagonist polypeptide of the present invention and monoclonal antibodies isolated from a culture comprising such hybridoma cells.

The term "antibody" as used herein is intended to include fragments thereof which are also specifically reactive with one of the subject agonist or antagonist polypeptides. Antibodies can be fragmented using conventional techniques and the fragments screened for utility in the same manner as described above for whole antibodies. For example, F(ab)$_2$ fragments can be generated by treating antibody with pepsin. The resulting F(ab)$_2$ fragment can be treated to reduce disulfide bridges to produce Fab fragments. The term "antibody" is further intended to encompass modified forms or antibodies or fragments thereof derivatives of antibodies or fragments thereof. Such modified forms or derivatives include, but are not limited to, bispecific molecules or antibodies, chimeric molecules or antibodies, humanized molecules or antibodies, single chain molecules or antibodies, having affinity for a protein which is conferred by at least one CDR region of an antibody. Modified forms or derivatives of antibodies can be produced recombinantly according to methods known in the art.

TRBP binding agents can also be produced in the cell to be targeted, by introduction into the target cell of one or more nucleic acids encoding the one or more polypeptides of the TRBP binding agent. For example, intracellular antibodies can be produced in the target cell.

Antibodies which specifically bind agonist or antagonist epitopes can also be used in immunohistochemical staining of tissue samples in order to evaluate the abundance and pattern of expression of each of the subject agonist or antagonist polypeptides. Anti-agonist or antagonist antibodies can be used diagnostically in immuno-precipitation and immuno-blotting to detect and evaluate protein levels in tissue as part of a clinical testing procedure. For instance, such measurements can be useful in predictive valuations of the onset or progression of proliferative disorders. Likewise, the ability to monitor protein levels in an individual can allow determination of the efficacy of a given treatment regimen for an individual afflicted with such a disorder. The level of polypeptides may be measured from cells in bodily fluid, such as in samples of cerebral spinal fluid or amniotic fluid, or can be measured in tissue, such as produced by biopsy.

Another application of antibodies of the present invention is in the immunological screening of cDNA libraries constructed in expression vectors such as λgt11, λgt18-23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of an agonist or antagonist protein, e.g. other orthologs of a particular TRBP protein or other paralogs from the same species, can then be detected with antibodies, as, for example, reacting nitrocellulose filters lifted from infected plates with antibodies. Positive phage detected by this assay can then be isolated from the infected plate. Thus, the presence of TRBP homologs can be detected and cloned from other animals, as can alternate isoforms (including splicing variants) from humans.

4.7 Methods of Treating Diseases

A pharmaceutical composition of the present invention can be, as appropriate, any of the preparations described above, including isolated polypeptides, binding agents, gene therapy constructs, antisense, ribozyme or triplex molecules, peptidomimetics or agents (e.g. small molecules) identified in the drug assays provided herein.

In one aspect, the invention provides a method for preventing or treating in a subject, a disease or condition associated with an aberrant TRBP activity, by administering to the subject a therapeutically effective amount of a compound which modulates at least one TRBP activity.

Subjects having a disease, which is caused or contributed to by an aberrant TRBP activity can be treated by administration to the subject of a therapeutically effective amount of a TRBP therapeutic. Depending on the type of TRBP aberrancy, a TRBP agonist or TRBP antagonist therapeutic can be used for treating the subject. The appropriate therapeutic can be determined based on assays described herein. For example, a sample obtained from the subject can be analyzed to determine whether the subject has an abnormally high or low TRBP protein level or TRBP activity. Assays which can be used for this purpose are further described in the section drawn to prognostic and diagnostic assays. Where the subject has an abnormally high TRBP protein level and/or activity, a TRBP antagonist therapeutic is administered to the subject. On the other hand, where the subject has an abnormally low TRBP protein level and/or activity, a TRBP agonist is administered to the subject. Agonist and antagonist compounds are further described below.

In one embodiment, the disease is a thyroid-related disorder or a metabolic disorder. TRBP has a sequence homology with a portion of a protein termed TRBP which has been shown to interact with the thyroid hormone receptor (Lee et al. infra). This reference discloses that interaction of TRBP with the thyroid hormone receptor β1 is decreased upon binding of thyroid hormone to the receptor. Accordingly, the invention provides TRBP therapeutics which are capable of modulating binding of a TRBP protein to a nuclear hormone receptor which is not bound by its ligand. The invention also provides TRBP therapeutics which are capable of modulating binding of a TRBP protein to a nuclear hormone receptor which is bound by its ligand. Thus, the invention provides methods for modulating the effect of thyroid hormones on cells. For example, a TRBP therapeutic can increase the effect of thyroid hormone on cells, thereby resulting, e.g, in increased expression of genes regulated by thyroid hormone. Alternatively, TRBP therapeutics can decrease or inhibit the effect of thyroid hormones on cells.

Thyroid-related disorders include those which are characterized by excessive thyroid hormone production or excessive thyroid hormone response, generally referred to as thyroitoxicosis. Examples of such disorders include Grave's disease, goiters, or disorders resulting from intake of abnormal dosages of iodine. Other thyroid-related disorders are those resulting from a deficient secretion of thyroid hormones or a deficient response to thyroid hormones and include Hashimoto's thyroiditis, cretiuis, small stature, myxedonia. Other thyroid-related disorders or conditions that can be treated by the methods of the invention described in the Background of the Invention section, supra.

In another embodiment, the disease is diabetes. In a preferred embodiment, the diabetes is type II diabetes. In an even more preferred embodiment, type II diabetes is non-insulin dependent diabetes mellitus NIDMM). In yet another preferred embodiment, type II diabetes is mature onset diabetes of the young (MODY).

Accordingly, the invention provides methods for treating a subject having an aberrant level of thyroid hormones, resulting, e.g., from production of abnormal levels of thryroid hormones by, e.g., modulating a TRBP activity. The invention also provides methods for treating subjects which have an abnormal response to thyroid hormones, e.g., a response which is either increased or decreased relative to normal responsiveness. According to the invention, a subject is treated by administering to the subject an efficient amount of a compound which modulates a TRBP activity, to thereby regulate the responsiveness of cells in the subject to thyroid hormones. The compound which can be either an agonist or an antagonist can be, e.g., a polypeptide, a nucleic acid, or any small molecule, which can be identified according to the methods described herein.

It will be apparent that the methods of the invention have numerous advantages for treating disorders caused by or contributed to by an aberrant level of thyroid hormone or an abnormal responsiveness of cells to thyroid hormone. For example, the method of the invention provides less drastic methods for treating disorders caused or contributed to by excessive thyroid hormone levels relative to known methods of treatment for such disorders, e.g., surgical procedure. Accordingly, a subject having an abnormally high level of thyroid hormone, such as a subject having Grave's disease, is treated according to the method of the invention by administering to the subject an efficient amount of a compound which modulates a TRBP activity, to thereby inhibit or reduce the responsiveness of a cell to thyroid hormones.

In one aspect, the invention features compounds that are agonists of a normal (functional) TRBP bioactivity. Such agonists can increase a TRBP activity by, e.g., increasing the interation of TRBP to a nucleic acid or to a protein, e.g., a receptor, such as a thyroid hormone receptor. An agonist can also increase a TRBP activity by increasing the level of TRBP protein, by, e.g., stimulating expression of the TRBP gene in a cell or by introducing into the cell a transgene encoding a TRBP protein operably linked to adequate regulatory sequences. Accordingly, diseases caused by, or contributed to by, an abnormally low level of TRBP or an abnormally low activity of TRBP relative to the level and activity of wild-type TRBP, can be treated by administering to the subject having such a disease an efficient amount of a compound which increases the expression of a TRBP gene or an operable nucleic acid encoding a TRBP protein. Thus, a subject having a disease that is caused by, or contributed to by, a mutation in a TRBP gene, resulting in an abnormally low protein level of TRBP or an abnormally low TRBP activity can be treated by administration to the subject of an effective amount of a compound which increases the protein level of TRBP or which potentiates TRBP activity.

A TRBP activity can also be agonized by acting on a step located downstream or upstream of TRBP in the biochemical pathway in which TRBP is involved. For example, in some situations, an agonist of a TRBP activity can be a compound which increases the expression of a gene whose expression is regulated by TRBP via a nuclear receptor, such as the thyroid hormone receptor. Accordingly, disorders that are contributed to, or caused by, a mutation in TRBP that results in a protein that is less active than the wild-type TRBP, can be treated by administering to the subject a compound which regulates a step located downstream of TRBP in the biochemical pathway in which TRBP is involved. Similarly, disorders that are caused by, or contributed to, by a level of TRBP that is abnormally low relative to the level of TRBP in a normal subject, can be treated by administration to the subject having such a disorder of an effective amount of a compound which regulates a step located downstream of TRBP in the biochemical pathway in which TRBP is involved. Thus, a subject suffering from a disease that is caused by, or contributed to by, a mutation in the TRBP gene resulting in abnormally low levels of TRBP or abnormally low activity of TRBP can be treated by administration to the subject of a compound that effects a step located downstream of TRBP in the biochemical pathway in which TRBP is involved. The term "agonistic TRBP therapeutics" is intended to encompass such compounds.

In another aspect, the invention features compounds that are antagonists of a normal (functional) TRBP bioactivity. Such antagonists can decrease a TRBP activity by, e.g., decreasing the interation of TRBP to a protein, e.g., a receptor, such as a thyroid hormone receptor. An antagonists can also decrease a TRBP activity by decreasing the level of TRBP protein, by, e.g., inhibiting expression of the TRBP gene in a cell or by introducing into the cell a transgene encoding a nucleic acid or protein, capable of inhibiting transcription, translation, or protein activity of TRBP in a cell in which it is expressed. Accordingly, diseases caused by, or contributed to by, an abnormally high level of TRBP or an abnormally potent activity of TRBP relative to the level and activity of wild-type TRBP, can be treated by administering to the subject having such a disease an efficient amount of a compound which decreases the expression of a TRBP gene or an operable nucleic acid encoding a TRBP antagonistic protein or nucleic acid. Thus, a subject having a disease that is caused by, or contributed to by, a mutation in a TRBP gene, resulting in an abnormally high protein level of TRBP or an abnormally potent TRBP activity can be treated by administration to the subject of an efficient amount of a compound which decreases the protein level or activity of TRBP.

A TRBP activity can also be antagonized by acting on a step located downstream or upstream of TRBP in the biochemical pathway in which TRBP is involved. For example, in some situations, an antagonist of a TRBP activity can be a compound which decreases the expression of a gene whose expression is regulated by a nuclear receptor, such as the thyroid hormone receptor, and the gene contains, e.g., a thyroid hormone response element. Accordingly, disorders that are contributed to, or caused by, a mutation in TRBP that results in a protein that is more active than the wild-type TRBP, can be treated by administering to the subject a compound which regulates a step located downstream of TRBP in the biochemical pathway in which TRBP is involved. Similarly, disorders that are caused by, or contributed to, by a level of TRBP that is abnormally high relative to the level of TRBP in a normal subject, can be treated by administration to the subject having such a disorder of an effective amount of a compound which regulates a step located downstream of TRBP in the biochemical pathway in which TRBP is involved. Thus, a subject suffering from a disease that is caused by, or contributed by, a mutation in the TRBP gene resulting in abnormally high levels of TRBP or abnormally strong activity of TRBP can be treated by administration to the subject of a compound that effects a step located downstream of TRBP in the biochemical pathway in which TRBP is involved. The term "antagonist TRBP therapeutics" is intended to encompass such compounds.

In another embodiment of the invention, a TRBP protein can be used to regulate the activity of a member of the steroid/thyroid superfamily of proteins. In fact, it has been shown that the activity of certain members of the superfamlly can interfere with the activity of other members of the family. For example, mutually antagonistic interactions have been shown to exist between various pairs of the steroid receptors estrogen receptor (ER), glucocorticoid receptor (GR), and progesterone receptor (PR) and also between thyroid hormone receptors and the retinoic acid receptor (RAR) and GR (Meyer et al. (1989) Cell 57:433; Barettino et al. (1994) EMBO J. 13:3039; and Yen et al. (1995) Endocrinology 136:440). Accordingly, the invention provides methods for treating or preventing diseases or conditions which are characterized by an abnormal activity of a nuclear hormone receptor having an activity with which TRBP is capable of interfering. For example, a soluble TRBP protein which is capable of interfering with the interaction of a second nuclear hormone receptor with its target, e.g, a transcription element, can be used to treat a condition characterized by an excessive activity of the second nuclear hormone receptor.

A nucleic acid and amino acid sequence comparison of TRBP with known genes and proteins revealed that TRBP has a weak homology, which may nevertheless be significant, with the 2'-5' oligoadenylate synthase (2'-5' A synthase) gene and protein. The 2'-5' oligoadenylate synthase is an enzyme, which upon activation by double stranded (ds) RNA, catalyzes the formation of 2'-5' oligoadenylates, which are necessary for activating an RNase, termed RNase L. Upon activation by 2'-5' oligoadenylates, the RNase L is capable of degrading RNA molecules. The 2'-5'A synthase gene is induced in response to interferon and has been shown to be active to protect cells against at least certain types of viruses. Based on the sequence homology with the 2,5A synthase, the invention could also provide methods for protecting subjects against a viral infection, such as an infection by human immunodeficiency virus I) by administering to the subject an effective amount of a TRBP therapeutic.

A nucleic acid and amino acid sequence comparison has also revealed a weak homology, which may nevertheless be significant, with ubiquitin proteins. Thus, the invention also provides methods for preventing or treating diseases caused by, or contributed to by an aberrant ubiquitin function, e.g., protein degradation.

4.7.1 Effective Dose

Toxicity and therapeutic efficacy of such compounds can be determined by standard pharmaceutical procedures in cell cultures or experimental animals, e.g. for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

4.7.2 Formulation and Use

Pharmaceutical compositions for use in accordance with the present invention may be formulated in conventional manner using one or more physiologically acceptable carriers or excipients. Thus, the compounds and their physiologically acceptable salts and solvates may be formulated for administration by, for example, injection, inhalation or insufflation (either through the mouth or the nose) or oral, buccal, parenteral or rectal administration.

For such therapy, the oligomers of the invention can be formulated for a variety of loads of administration, including systemic and topical or localized administration. Techniques and formulations generally may be found in *Remmington's Pharmaceutical Sciences*, Meade Publishing Co., Easton, Pa. For systemic administration, injection is preferred, including intramuscular, intravenous, intraperitoneal, and subcutaneous. For injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

For oral administration, the pharmaceutical compositions may take the form of for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the oligomers of the invention are formulated into ointments, salves, gels, or creams as generally known in the art.

In clinical settings, the gene delivery systems for the therapeutic TRBP gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) PNAS 91:3054–3057). A TRBP gene, or a sequence homologous thereto can be delivered in a gene therapy construct by electroporation using techniques described, for example, by Dev et al. ((1994) Cancer Treat Rev 20:105–115).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery system.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

4.8 Diagnostic and Prognostic Assays

The invention further provides methods for determining whether a subject is at risk of developing a disease caused by, or contributed to by, an aberrant TRBP activity. In one embodiment, the invention provides methods for determining whether a subject is at risk of developing a thyroid disorder, such as thyroitoxicosis. In another embodiment, the invention provides methods for determining whether a subject is at risk of developing diabetes, e.g. type II diabetes, comprising determining whether the subject has an aberrant TRBP activity.

In one embodiment, the diagnostic method comprises determining whether a subject has an abnormal mRNA and/or protein level of TRBP, such as by Northern blot analysis, in situ hybridization, immunoprecipitation, Western blot hybridization, or immunohistochemistry. According to the method, cells are obtained from a subject and the protein or mRNA level of TRBP is determined and compared to the protein or mRNA level of TRBP in a healthy subject. An abnormal level of TRBP protein or mRNA level might be indicative of an aberrant TRBP activity.

In another embodiment, the diagnostic method comprises measuring at least one activity of TRBP. For example, the level of expression of genes which are regulated by TRBP can be determined. Alternatively, the extent of interaction of TRBP with another protein, e.g., the thyroid hormone receptor can be determined. Comparison with results from similar experiments performed in healthy subjects will be indicative whether a subject has an abnormal TRBP activity.

The invention also provides numerous diagnostic and prognostic methods comprising determining whether a genetic lesion is present in a TRBP gene in a subject. A genetic lesion can be any difference present in the gene of a subject which is not present in a healthy subject who is not at risk of developing a disease associated with aberrant TRBP activity. Thus, a genetic lesion can be a point mutation, such as a deletion, addition or substitution of a nucleotide. A genetic lesion can also be a deletion, addition, or substitution of more than one nucleotide. A genetic lesion can also be a chromosomal rearrangement, such as a translocation. The genetic lesion can be in any portion of the TRBP gene, e.g. promoter, enhancers, exons, introns, translated or untranslated regions. Accordingly, the invention provides methods for determining the presence of a genetic lesion in a TRBP gene and/or regulatory sequence thereof. These methods include, but are not limited to, methods involving sequence analysis, Southern blot hybridization, restriction enzyme site mapping, and methods involving detection of absence of nucleotide pairing between the nucleic acid to be analyzed and a probe. These and other methods are further described infra.

Also within the scope of the invention are probes and primers for use in prognostic or diagnostic assays. For instance, the present invention provides a probe and/or primer comprising a substantially purified oligonucleotide, which oligonucleotide comprises a region of nucleotide sequence that hybridizes under stringent conditions to at least approximately 12, preferably 25, more preferably 40, 50 or 75 consecutive nucleotides of a sense or anti-sense sequence of TRBP nucleic acid sequence.

In preferred embodiments, a probe comprises a label group attached thereto and able to be detected, e.g. the label group is selected from amongst radioisotopes, fluorescent compounds, enzymes, and enzyme co-factors.

In preferred embodiments, the methods for determining whether a subject is at risk for developing a disease associated with an aberrant TRBP activity is characterized as comprising detecting, in a sample of cells from the subject, the presence or absence of a genetic lesion characterized by at least one of(i) an alteration affecting the integrity of a gene encoding a TRBP protein, or (ii) the mis-expression of the TRBP gene. To illustrate, such genetic lesions can be detected by ascertaining the existence of at least one of (i) a deletion of one or more nucleotides from a TRBP gene, (ii) an addition of one or more nucleotides to a TRBP gene, (iii) a substitution of one or more nucleotides of a TRBP gene, (iv) a gross chromosomal rearrangement of a TRBP gene, (v) a gross alteration in the level of a messenger RNA transcript of a TRBP gene, (vii) aberrant modification of a TRBP gene, such as of the methylation pattern of the genomic DNA, (vii) the presence of a non-wild type splicing pattern of a messenger RNA transcript of a TRBP gene, (viii) a non-wild type level of a TRBP protein, (ix) allelic loss of a TRBP gene, and/or (x) inappropriate post-translational modification of a TRBP protein. As set out below, the present invention provides a large number of assay techniques for detecting lesions in a TRBP gene.

In an exemplary embodiment, there is provided a nucleic acid composition comprising a (purified) oligonucleotide probe including a region of nucleotide sequence which is capable of hybridizing to a sense or antisense sequence of a TRBP gene or naturally occurring mutants thereof, or 5' or 3' flanking sequences or intronic sequences naturally associated with the subject TRBP genes or naturally occurring mutants thereof. The nucleic acid of a cell is rendered accessible for hybridization, the probe is exposed to nucleic acid of the sample, and the hybridization of the probe to the sample nucleic acid is detected. Such techniques can be used to detect lesions at either the genomic or mRNA level, including deletions, substitutions, etc., as well as to determine mRNA transcript levels.

In certain embodiments, detection of the lesion comprises utilizing the probe/primer in a polymerase chain reaction (PCR) (see, e.g. U.S. Pat. Nos. 4,683,195 and 4,683,202), such as anchor PCR or RACE PCR, or, alternatively, in a ligase chain reaction (LCR) (see, e.g., Landegran et al. (1988) Science 241:1077–1080; and Nakazawa et al. (1994) PNAS 91:360–364), the latter of which can be particularly useful for detecting point mutations in the TRBP gene (see Abravaya et al. (1995) Nuc Acid Res 23:675–682). In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize to a TRBP gene under conditions such that hybridization and amplification of the TRBP gene (if present) occurs, and (iv) detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., 1990, Proc. Natl. Acad. Sci. USA 87:1874–1878), transcriptional amplification system (Kwoh, D. Y. et al., 1989, Proc. Natl. Acad. Sci. USA 86:1173–1177), Q-Beta Replicase (Lizardi P. M. et al., 1988, Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In a preferred embodiment of the subject assay, mutations in a TRBP gene from a sample cell are identified by alterations in restriction enzyme cleavage patterns. For example, sample and control DNA is isolated, amplified (optionally), digested with one or more restriction endonucleases, and fragment length sizes are determined by gel electrophoresis. Moreover, the use of sequence specific ribozymes (see, for example, U.S. Pat. No. 5,498,531) can be used to score for the presence of specific mutations by development or loss of a ribozyme cleavage site.

In yet another embodiment, any of a variety of sequencing reactions known in the art can be used to directly sequence the TRBP gene and detect mutations by comparing the sequence of the sample TRBP with the corresponding wild-type (control) sequence. Exemplary sequencing reactions include those based on techniques developed by Maxim and Gilbert (*Proc. Natl Acad Sci* USA (1977) 74:560) or Sanger (Sanger et al (1977) *Proc. Nat. Acad Sci* 74:5463). It is also contemplated that any of a variety of automated sequencing procedures may be utilized when performing the subject assays (*Biotechniques* (1995) 19:448), including sequencing by mass spectrometry (see, for example PCT publication WO 94/16101; Cohen et al. (1996) *Adv Chromatogr* 36:127–162; and Griffin et al. (1993) *Appl Biochem Biotechnol* 38:147–159). It will be evident to one skilled in the art that, for certain embodiments, the occurrence of only one, two or three of the nucleic acid bases need be determined in the sequencing reaction. For instance, A-tract or the like, e.g., where only one nucleic acid is detected, can be carried out.

In a further embodiment, protection from cleavage agents (such as a nuclease, hydroxylamine or osmium tetroxide and with piperidine) can be used to detect mismatched bases RNA/RNA or RNA/DNA heteroduplexes (Myers, et al. (1985) *Science* 230:1242). In general, the art technique of "mismatch cleavage" starts by providing heteroduplexes formed by hybridizing (labelled) RNA or DNA containing the wild-type TRBP sequence with potentially mutant RNA or DNA obtained from a tissue sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al (1988) *Proc. Natl Acad Sci USA* 85:4397; Saleeba et al (1992) Methods Enzymod. 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in TRBP cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a TRBP sequence, e.g., a wild-type TRBP sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in TRBP genes. For example, single strand conformation polymorphism (SSCP) may be used to detect differences in electrophoretic mobility between mutant and wild type nucleic acids (Orita et al. (1989) *Proc Natl. Acad. Sci USA* 86:2766, see also Cotton (1993) *Mutat Res* 285:125–144; and Hayashi (1992) *Genet Anal Tech Appl* 9:73–79). Single-stranded DNA fragments of sample and control TRBP nucleic acids will be denatured and allowed to renature. The secondary structure of single-stranded nucleic acids varies according to sequence, the resulting alteration in electrophoretic mobility enables the detection of even a single base change. The DNA fragments may be labelled or detected with labelled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet 7:5).

In yet another embodiment the movement of mutant or wild-type fragments in polyacrylamide gels containing a gradient of denaturant is assayed using denaturing gradient gel electrophoresis (DGGE) (Myers et al (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) Biophys Chem 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163); Saiki et al (1989) Proc. Natl Acad Sci USA 86:6230). Such allele specific oligonucleotide hybridization techniques may be used to test one mutation per reaction when oligonucleotides are hybridized to PCR amplified target DNA or a number of different mutations when the oligonucleotides are attached to the hybridizing membrane and hybridized with labelled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al (1989) Nucleic Acids Res. 17:2437–2448) or at the extreme 3' end of one primer where, under appropriate conditions, mismatch can prevent, or reduce polymerase extension (Prossner (1993) Tibtech 11:238. In addition it may be desirable to introduce a novel restriction site in the region of the mutation to create cleavage-based detection (Gasparini et al (1992) Mol. Cell Probes 6:1). It is anticipated that in certain embodiments amplification may also be performed using Taq ligase for amplification (Barany (1991) Proc. Natl. Acad Sci USA 88:189). In such cases, ligation will occur only if there is a perfect match at the 3' end of the 5' sequence making it possible to detect the presence of a known mutation at a specific site by looking for the presence or absence of amplification.

For mutations that produce premature termination of protein translation, the protein truncation test (PTT) offers an efficient diagnostic approach (Roest, et. al., (1993) Hum. Mol. Genet. 2:1719–21; van der Luijt, et. al., (1994) Genomics 20:1–4). For PTT, RNA is initially isolated from available tissue and reverse-transcribed, and the segment of interest is amplified by PCR The products of reverse transcription PCR are then used as a template for nested PCR amplification with a primer that contains an RNA polymerase promoter and a sequence for initiating eukaryotic translation. After amplification of the region of interest, the unique motifs incorporated into the primer permit sequential in vitro transcription and translation of the PCR products. Upon sodium dodecyl sulfate-polyacrylamide gel electrophoresis of translation products, the appearance of truncated polypeptides signals the presence of a mutation that causes premature termination of translation. In a variation of this technique, DNA (as opposed to RNA) is used as a PCR template when the target region of interest is derived from a single exon.

Another embodiment of the invention provides for a nucleic acid composition comprising a (purified) oligonucleotide probe including a region of nucleotide sequence which is capable of hybridizing to a sense or antisense sequence of a TRBP gene, or naturally occurring mutants thereof, or 5' or 3' flanking sequences or intronic sequences naturally associated with the subject TRBP genes or naturally occurring mutants thereof The nucleic acid of a cell is rendered accessible for hybridization, the probe is exposed to nucleic acid of the sample, and the hybridization of the probe to the sample nucleic acid is detected. Such techniques can be used to detect lesions at either the genomic or mRNA level, including deletions, substitutions, etc., as well as to determine mRNA transcript levels. Such oligonucleotide probes can be used for both predictive and therapeutic evaluation of allelic mutations which might be manifest in, for example, thyroid-related disorders.

The methods described herein may be performed, for example, by utilizing pre-packaged diagnostic kits comprising at least one probe nucleic acid, primer set; and/or antibody reagent described herein, which may be conveniently used, e.g., in clinical settings to diagnose patients exhibiting symptoms or family history of a disease or illness involving a TRBP protein.

Any cell type or tissue, in which a TRBP protein is expressed may be utilized in the diagnostics described below. For example, a subject's bodily fluid (e.g. blood) can be obtained by known techniques (e.g. venipuncture). Alternatively, nucleic acid tests can be performed on dry samples (e.g. hair or skin). Fetal nucleic acid samples can be obtained from maternal blood as described in International Patent Application No. WO91/07660 to Bianchi. Alternatively, amniocytes or chorionic villi may be obtained for performing prenatal testing.

Diagnostic procedures may also be performed in situ directly upon tissue sections (fixed and/or frozen) of patient tissue obtained from biopsies or resections, such that no nucleic acid purification is necessary. Nucleic acid reagents may be used as probes and/or primers for such in situ procedures (see, for example, Nuovo, G. J., 1992, PCR in situ hybridization: protocols and applications, Raven Press, N.Y.).

In addition to methods which focus primarily on the detection of one nucleic acid sequence, profiles may also be assessed in such detection schemes. Fingerprint profiles may be generated, for example, by utilizing a differential display procedure, Northern analysis and/or RT-PCR.

Antibodies directed against wild type or mutant TRBP proteins, which are discussed, above, may also be used in disease diagnostics and prognostics. Such diagnostic methods, may be used to detect abnormalities in the level of TRBP protein expression, or abnormalities in the structure and/or tissue, cellular, or subcellular location of a TRBP protein. Structural differences may include, for example, differences in the size, electronegativity, or antigenicity of the mutant TRBP protein relative to the normal TRBP protein. Protein from the tissue or cell type to be analyzed may easily be detected or isolated using techniques which are well known to one of skill in the art, including but not limited to western blot analysis. For a detailed explanation of methods for carrying out western blot analysis, see Sambrook et al, 1989, supra, at Chapter 18. The protein detection and isolation methods employed herein may also be such as those described in Harlow and Lane, for example, (Harlow, E. and Lane, D., 1988, "Antibodies: A Laboratory Manual", Cold Spring Harbor Laboratory Press, Cold Spring Harbor, N.Y.), which is incorporated herein by reference in its entirety.

This can be accomplished, for example, by immunofluorescence techniques employing a fluorescently labeled antibody (see below) coupled with light microscopic, flow cytometric, or fluorimetric detection. The antibodies (or fragments thereof) useful in the present invention may, additionally, be employed histologically, as in immunofluorescence or immunoelectron microscopy, for in situ detection of TRBP proteins. In situ detection may be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the TRBP protein, but also its distribution in the examined tissue. Using the present invention, one of ordinary skill will readily perceive that any of a wide variety of histological methods (such as staining procedures) can be modified in order to achieve such in situ detection.

Often a solid phase support or carrier is used as a support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

One means for labeling an anti-TRBP protein specific antibody is via linkage to an enzyme and use in an enzyme immunoassay (EIA) (Voller, "The Enzyme Linked Immunosorbent Assay (ELISA)", *Diagnostic Horizons* 2:1–7, 1978, Microbiological Associates Quarterly Publication, Walkersville, Md.; Voller, et al., J. Clin. Pathol. 31:507–520 (1978); Butler, Meth. Enzymol. 73:482–523 (1981); Maggio, (ed.) *Enzyme Immunoassay*, CRC Press, Boca Raton, Fla., 1980; Ishikawa, et al., (eds.) *Enzyme Immunoassay*, Kgaku Shoin, Tokyo, 1981). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by calorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect fingerprint gene wild type or mutant peptides through the use of a radioimmunoassay (RIA) (see, for example, Weintraub, B., *Principles of Radioimmunoassays*, Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Moreover, it will be understood that any of the above methods for detecting alterations in a gene or gene product can be used to monitor the course of treatment or therapy.

4.9 Drug Screening Assays

The present invention facilitates the development of assays which can be used to screen for drugs, i.e., TRBP therapeutics, that modulate the expression of a TRBP gene or the activity of a TRBP protein, which can then be used to treat diseases, e.g., diabetes type II or thyroid-related disorders.

The TRBP protein used in these assays can be a native or mutant protein isolated from a cell. Alternatively, the TRBP protein can be produced recombinantly. 4.9.1 Cell-free in vitro assays In one embodiment of the invention, a TRBP therapeutics is a drug which modulates the interaction of a TRBP protein with another molecule, such as a macromolecule. The molecule can be a protein, such as a nuclear hormone receptor. Preferred nuclear hormone receptors include the thyroid hormone receptor. Alternatively, if it can be shown that TRBP interacts with nucleic acids, a TRBP therapeutic can be a drug which modulates the interaction of a TRBP protein with a nucleic acid. The molecule with which TRBP protein interacts can be a molecule located upstream or downstream of TRBP in the biochemical pathway in which TRBP is involved. Yet other TRBP therapeutics are drugs which modulate expression of a TRBP gene.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with upstream or downstream molecules. Accordingly, in an exemplary screening assay of the present invention, the compound of interest is contacted with proteins which may function upstream (including both activators (enhancers) and repressors of its activity) or to proteins and/or nucleic acids (e.g. promoter) which may function downstream of the TRBP polypeptide, whether they are positively or negatively regulated by it. To the mixture of the compound and the upstream or downstream molecule (e.g., protein or nucleic acid) is then added a composition containing a TRBP polypeptide. Detection and quantification of complexes of TRBP with it's upstream or downstream molecules provide a means for determining a compound's efficacy at antagonizing (inhibiting) or agonizing (potentiating) complex formation between a TRBP and a TRBP binding molecule. The efficacy of the compound can be assessed by generating dose response curves from data obtained using various concentrations of the test compound. Moreover, a control assay can also be performed to provide a baseline for comparison. In the control assay, isolated and purified TRBP polypeptide is added to a composition containing the TRBP binding molecule, and the formation of a complex is quantitated in the absence of the test compound. Complex formation between the TRBP polypeptide and a binding molecule may be detected by a variety of techniques. Modulation of the formation of complexes can be quantitated using, for example, detectably labeled proteins such as radiolabeled, fluorescently labeled, or enzymatically labeled TRBP polypeptides, by immunoassay, or by chromatographic detection.

Typically, it will be desirable to immobilize either TRBP or its binding molecule to facilitate separation of complexes from uncomplexed forms, as well as to accommodate automation of the assay. Binding of TRBP to an upstream or downstream molecule, in the presence and absence of a candidate agent, can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. For example, glutathione-S-transferase/TRBP (GST/TRBP) fusion proteins can be adsorbed onto glutathione sepharose beads (Sigma Chemical, St. Louis, Mo.) or glutathione derivatized microtitre plates, which are then combined with the cell lysates, e.g. an $^{35}$S-labeled, and the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintilant), or in the supernatant after the complexes are subsequently dissociated. Alternatively, the complexes can be dissociated from the matrix, separated by SDS-PAGE, and the level of TRBP-binding protein found in the bead fraction quantitated from the gel using standard electrophoretic techniques.

Other techniques for immobilizing proteins on matrices are also available for use in the subject assay. For instance, a TRBP protein or its cognate binding molecule can be immobilized utilizing conjugation of biotin and streptavidin. For instance, biotinylated TRBP molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with TRBP but which do not interfere with binding of upstream or downstream molecule can be derivatized to the wells of the plate, and TRBP trapped in the wells by antibody conjugation. As above, preparations of a TRBP binding protein and a test compound are incubated in the TRBP presenting wells of the plate, and the amount of complex trapped in the well can be quantitated. Exemplary methods for detecting such complexes, in addition to those described above for the GST-immobilized complexes, include immunodetection of complexes using antibodies reactive with the TRBP binding element, or which are reactive with the TRBP protein and compete with the binding molecule; as well as enzyme-linked assays which rely on detecting an enzymatic activity associated with the binding element, either intrinsic or extrinsic activity. In the instance of the latter, the enzyme can be chemically conjugated or provided as a fusion protein with the TRBP binding partner. To illustrate, the TRBP binding partner can be chemically cross-linked or genetically fused with horseradish peroxidase, and the amount of polypeptide trapped in the complex can be assessed with a chromogenic substrate of the enzyme, e.g. 3,3'-diamino-benzadine terahydrochloride or 4-chloro-1-napthol. Likewise, a fusion protein comprising the polypeptide and glutathione-S-transferase can be provided, and complex formation quantitated by detecting the GST activity using 1-chloro-2, 4-dinitrobenzene (Habig et al (1974) J Biol Chem 249:7130).

For processes which rely on immunodetection for quantitating the molecule or TRBP protein trapped in the complex, antibodies against the protein, such as anti-TRBP antibodies, can be used. Alternatively, the protein to be detected in the complex can be "epitope tagged" in the form of a fusion protein which includes, in addition to the TRBP sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) *J Biol Chem* 266:21150–21157) which includes a 10-residue sequence from c-myc, as well as the pFLAG system (International Biotechnologies, Inc.) or the pEZZ-protein A system (Pharamacia, N.J.).

If TRBP is shown to interact with one or more nucleic acid sequences, compounds disrupting such interaction are within the scope of the invention. Assays for screening drugs which disrupts the interaction of a DNA binding protein with a nucleic acid can be performed using, e.g., transcription factor-DNA binding assays, such as those described in U.S. Pat. No. 5,563,036, which is owned by Tularik and is specifically incorporated by reference herein. Other assays for monitoring interaction of a DNA binding factor to DNA are within the skill in the art.

Further, an in vitro transcriptional control assay can be used to detect agonists or antagonists of TRBP which can be used for treatment of diseases caused by or contributed to by an aberrant TRBP activity. For example, an in vitro transcription array can be performed comprising TRBP, a TRBP-binding protein, e.g. a thyroid hormone receptor, a reporter construct comprises thyroid hormone receptor binding elements and a nuclear extract. A test compound can then be added to the transcription reaction and transcription of the reporter gene is determined according to methods known in the art.

Further, TRBP may be translationally or post-translationally modified by processes such as mRNA editing or protein truncation. Assays to specifically monitor these processes can be performed according to protocols, which are well-known in the art and compounds which modulate such modifications can be isolated using such assays.

In yet another aspect of the invention, the subject TRBP polypeptides can be used in a "two hybrid" assay (see, for example, U.S. Pat. No. 5,283,317; Zervos et al. (1993) Cell 72:223–232; Madura et al. (1993) J Biol Chem 268:12046–12054; Bartel et al. (1993) Biotechniques 14:920–924; Iwabuchi et al. (1993) Oncogene 8:1693–1696; and Brent WO94/10300), for isolating coding sequences for other cellular proteins which bind to or interact with a TRBP (e.g., TRBP binding proteins" or "TRBPbp"). Such proteins can then be used in an assay for isolating TRBP therapeutics which modulate TRBP activity.

Briefly, the two hybrid assay relies on reconstituting in vivo a functional transcriptional activator protein from two separate fusion proteins. In particular, the method makes use of chimeric genes which express hybrid proteins. To illustrate, a first hybrid gene comprises the coding sequence for a DNA-binding domain of a transcriptional activator fused in frame to the coding sequence for a TRBP polypeptide. The second hybrid protein encodes a transcriptional activation domain fused in frame to a sample gene from a cDNA library. If the bait and sample hybrid proteins are able to interact, e.g., form a TRBP dependent complex, they bring into close proximity the two domains of the transcriptional activator. This proximity is sufficient to cause transcription of a reporter gene which is operably linked to a transcriptional regulatory site responsive to the transcriptional activator, and expression of the reporter gene can be detected and used to score for the interaction of the TRBP and sample proteins. An exemplary tissue culture based reporter assay is described in further detail in the following Examples.

4.9.2 Cell based assays

In addition to cell-free assays, such as described above, cell-based assays for identifying small molecule agonists/antagonists and the like which modulate TRBP activity can be performed.

In one embodiment, test compounds are added to primary culture cells or to tissue culture cells expressing TRBP for an appropriate amount of time and at least one activity of TRBP is measured. For example, the amount of complex formed between TRBP and at least one other molecule, such as a nuclear hormone receptor is measured. This can be done by assays, such as immunoprecipitation assays and electrophoresis. In another embodiment, the TRBP activity that is measured is the expression of a gene which is modulated by TRBP binding to a molecule which can be genes which are regulated by the thyroid hormone receptor.

In another embodiment, cells can be caused to overexpress a recombinant TRBP protein in the presence and absence of a test agent of interest, with the assay scoring for modulation in TRBP responses by the target cell mediated by the test agent. As with the cell-free assays, agents which produce a statistically significant change in TRBP-dependent responses (either inhibition or potentiation) can be identified. In an illustrative embodiment, the expression or activity of a TRBP is modulated in cells and the effects of compounds of interest on the readout of interest (such as initiation of transcription) are measured. For example, to identify compounds which modulate the interaction of a TRBP protein with another protein, such as a nuclear hormone receptor, a cell, e.g., a yeast cell, is stably transfected with constructs encoding TRBP or a portion thereof and the second protein and other elements used in a two hybrid system. An analogous system can also be engineered in mammalian cells, e.g., human cells.

In another example, the expression of genes which are up- or down-regulated in response to a TRBP dependent signal cascade can be assayed in a cell which has been incubated with a test compound. In preferred embodiments, the regulatory regions of such genes, e.g., the 5' flanking promoter and enhancer regions, are operably linked to a detectable marker (such as luciferase) which encodes a gene product that can be readily detected.

For example, cells can be engineered to express TRBP genes and a second gene construct containing a TRBP response element in operative linkage with a reporter gene construct, such as luciferase or chloramphenicol acetyl transferase, or other reporter gene known in the art. Cells can then be contacted with test compounds. TRBP ligands will cause transcriptional activation of the reporter gene as compared to that seen in control cells in the absence of ligand or in the absence of the recombinant TRBP or TRBP response element-reporter gene construct. For testing antagonist compounds, cells can be contacted with an agonist prior to being contacted with test compounds and an inhibition of reporter gene transcription or product can be detected.

The transgenic or knock-out animals discussed herein may be used to generate cell lines, which can be used in the above-described cell based assays. While primary cultures derived from these transgenic animals of the invention may be utilized, the generation of continuous cell lines is preferred. For examples of techniques which may be used to derive a continuous cell fine from the transgenic animals, see Small et al., 1985, Mol. Cell Biol. 5:642–648.

Monitoring the influence of compounds on cells may be applied not only in basic drug screening, but also in clinical trials. In such clinical trials, the expression of a panel of genes may be used as a "read out" of a particular drug's therapeutic effect.

4.10 Transgenic and Knock-out animals

These systems may be used in a variety of applications. For example, the cell- and animal-based model systems may be used to further characterize TRBP genes and proteins, in particular their role in diseases associated with an aberrant TRBP activity. For example, a knock-out animal can be used to determine the effect of total absence of the TRBP protein in a animal. In particular, these mice will be monitored for the development of a thyroid-related disorder or diabetes. Such disorders could develop either spontaneously, or alternatively, such diseases can be induced in such mice when a second event occurs. The mice of the invention can be used to determine which second event is necessary to induce such diseases.

In a preferred embodiment, TRBP knock-out mice or cells thereof are used in screening assays for identifying drugs which can overcome the defect of a cell resulting from the absence of a TRBP protein. Such drugs can then be used to treat subjects having an absence of functional TRBP protein or decreased amounts of functional TRBP or a TRBP protein which is less active than wild-type TRBP protein.

Furthermore, crossing of TRBP knock-out mice with mice transgenic for a wild-type or mutated TRBP gene or portion thereof can have multiple applications. For example, a mouse or other animal, can be created which has only a mutated form of a TRBP protein similar to a mutated form found in humans. These mice could be used to identify drugs which remedy the cellular defect caused by this genetic defect.

Thus, the animal- and cell-based models may be used to identify drugs, pharmaceuticals, therapies and interventions which may be effective in treating disease.

One aspect of the present invention concerns transgenic animals which are comprised of cells (of that animal) which contain a transgene of the present invention and which preferably (though optionally) express an exogenous TRBP protein in one or more cells in the animal. A TRBP transgene can encode the wild-type form of the protein, or can encode homologs thereof, including both agonists and antagonists, as well as antisense constructs. In preferred embodiments, the expression of the transgene is restricted to specific subsets of cells, tissues or developmental stages utilizing, for example, cis-acting sequences that control expression in the desired pattern. In the present invention, such mosaic expression of a TRBP protein can be essential for many forms of lineage analysis and can additionally provide a means to assess the effects of, for example, lack of TRBP expression which might grossly alter development in small patches of tissue within an otherwise normal embryo. Toward this end, tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

Genetic techniques which allow for the expression of transgenes can be regulated via site-specific genetic manipulation in vivo are known to those skilled in the art. For instance, genetic systems are available which allow for the regulated expression of a recombinase that catalyzes the genetic recombination of a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of one of the subject TRBP proteins. For example, excision of a target sequence which interferes with the expression of a recombinant TRBP gene, such as one which encodes an antagonistic homolog or an antisense transcript, can be designed to activate expression of that gene. This interference with expression of the protein can result from a variety of mechanisms, such as spatial separation of the TRBP gene from the promoter element or an internal stop codon. Moreover, the transgene can be made wherein the coding sequence of the gene is flanked by recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation.

The transgenic animals of the present invention all include within a plurality of their cells a transgene of the present invention, which transgene alters the phenotype of the "host cell" with respect to regulation of cell growth, death and/or differentiation. Since it is possible to produce transgenic organisms of the invention utilizing one or more of the transgene constructs described herein, a general description will be given of the production of transgenic organisms by referring generally to exogenous genetic material. This general description can be adapted by those skilled in the art in order to incorporate specific transgene sequences into organisms utilizing the methods and materials described below.

In an illustrative embodiment, either the cre/loxP recombinase system of bacteriophage P1 (Lakso et al. (1992) *PNAS* 89:6232–6236; Orban et al. (1992) *PNAS* 89:6861–6865) or the FLP recombinase system of *Saccharomyces cerevisiae* (O'Gorman et al. (1991) *Science* 251:1351–1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al. (1984) *J. Biol. Chem.* 259:1509–1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation expression of a recombinant TRBP protein can be regulated via control of recombinase expression.

Use of the cre/loxP recombinase system to regulate expression of a recombinant TRBP protein requires the construction of a transgenic animal containing transgenes encoding both the Cre recombinase and the subject protein. Animals containing both the Cre recombinase and a recombinant TRBP gene can be provided through the construction of "double" transgenic animals. A convenient method for providing such animals is to mate two transgenic animals each containing a transgene, e.g., a TRBP gene and recombinase gene.

One advantage derived from initially constructing transgenic animals containing a TRBP transgene in a recombinase-mediated expressible format derives from the likelihood that the subject protein, whether agonistic or antagonistic, can be deleterious upon expression in the transgenic animal. In such an instance, a founder population, in which the subject transgene is silent in all tissues, can be propagated and maintained. Individuals of this founder population can be crossed with animals expressing the recombinase in, for example, one or more tissues and/or a desired temporal pattern. Thus, the creation of a founder population in which, for example, an antagonistic TRBP transgene is silent will allow the study of progeny from that founder in which disruption of TRBP mediated induction in a particular tissue or at certain developmental stages would result in, for example, a lethal phenotype.

Similar conditional transgenes can be provided using prokaryotic promoter sequences which require prokaryotic proteins to be simultaneous expressed in order to facilitate expression of the TRBP transgene. Exemplary promoters and the corresponding trans-activating prokaryotic proteins are given in U.S. Pat. No. 4,833,080.

Moreover, expression of the conditional transgenes can be induced by gene therapy-like methods wherein a gene encoding the trans-activating protein, e.g. a recombinase or a prokaryotic protein, is delivered to the tissue and caused to be expressed, such as in a cell-type specific manner. By this method, a TRBP transgene could remain silent into adulthood until "turned on" by the introduction of the trans-activator.

In an exemplary embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The specific line(s) of any animal used to practice this invention are selected for general good health, good embryo yields, good pronuclear visibility in the embryo, and good reproductive fitness. In addition, the haplotype is a significant factor. For example, when transgenic mice are to be produced, strains such as C57BL/6 or FVB lines are often used (Jackson Laboratory, Bar Harbor, Me.). Preferred strains are those with $H-2^b$, $H-2^d$ or $H-2^q$ haplotypes such as C57BL/6 or DBA/1. The line(s) used to practice this invention may themselves be transgenics, and/or may be knockouts (i.e., obtained from animals which have one or more genes partially or completely suppressed).

In one embodiment, the transgene construct is introduced into a single stage embryo. The zygote is the best target for micro-injection. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster et al. (1985) *PNAS* 82:4438–4442). As a consequence, all cells of the transgenic animal will carry the incorporated transgene. This will in general also be reflected in the efficient transmission of the transgene to offspring of the founder since 50% of the germ cells will harbor the transgene.

Normally, fertilized embryos are incubated in suitable media until the pronuclei appear. At about this time, the nucleotide sequence comprising the transgene is introduced into the female or male pronucleus as described below. In some species such as mice, the male pronucleus is preferred. It is most preferred that the exogenous genetic material be added to the male DNA complement of the zygote prior to its being processed by the ovum nucleus or the zygote female pronucleus. It is thought that the ovum nucleus or female pronucleus release molecules which affect the male DNA complement, perhaps by replacing the protamines of the male DNA with histones, thereby facilitating the combination of the female and male DNA complements to form the diploid zygote.

Thus, it is preferred that the exogenous genetic material be added to the male complement of DNA or any other complement of DNA prior to its being affected by the female pronucleus. For example, the exogenous genetic material is added to the early male pronucleus, as soon as possible after the formation of the male pronucleus, which is when the male and female pronuclei are well separated and both are located close to the cell membrane. Alternatively, the exogenous genetic material could be added to the nucleus of the sperm after it has been induced to undergo decondensation. Sperm containing the exogenous genetic material can then be added to the ovum or the decondensed sperm could be added to the ovum with the transgene constructs being added as soon as possible thereafter.

Introduction of the transgene nucleotide sequence into the embryo may be accomplished by any means known in the art such as, for example, microinjection, electroporation, or lipofection. Following introduction of the transgene nucleotide sequence into the embryo, the embryo may be incubated in vitro for varying amounts of time, or reimplanted into the surrogate host, or both. In vitro incubation to maturity is within the scope of this invention. One common method in to incubate the embryos in vitro for about 1–7 days, depending on the species, and then reimplant them into the surrogate host.

For the purposes of this invention a zygote is essentially the formation of a diploid cell which is capable of developing into a complete organism. Generally, the zygote will be comprised of an egg containing a nucleus formed, either naturally or artificially, by the fusion of two haploid nuclei from a gamete or gametes. Thus, the gamete nuclei must be ones which are naturally compatible, i.e., ones which result in a viable zygote capable of undergoing differentiation and developing into a functioning organism. Generally, a euploid zygote is preferred. If an aneuploid zygote is obtained, then the number of chromosomes should not vary by more than one with respect to the euploid number of the organism from which either gamete originated.

In addition to similar biological considerations, physical ones also govern the amount (e.g., volume) of exogenous genetic material which can be added to the nucleus of the zygote or to the genetic material which forms a part of the zygote nucleus. If no genetic material is removed, then the amount of exogenous genetic material which can be added is limited by the amount which will be absorbed without being physically disruptive. Generally, the volume of exogenous genetic material inserted will not exceed about 10 picoliters. The physical effects of addition must not be so great as to physically destroy the viability of the zygote. The biological limit of the number and variety of DNA sequences will vary depending upon the particular zygote and functions of the exogenous genetic material and will be readily apparent to one skilled in the art, because the genetic material, including the exogenous genetic material, of the resulting zygote must be biologically capable of initiating and maintaining the differentiation and development of the zygote into a functional organism.

The number of copies of the transgene constructs which are added to the zygote is dependent upon the total amount of exogenous genetic material added and will be the amount which enables the genetic transformation to occur. Theoretically only one copy is required; however, generally, numerous copies are utilized, for example, 1,000–20,000 copies of the transgene construct, in order to insure that one copy is functional. As regards the present invention, there will often be an advantage to having more than one functioning copy of each of the inserted exogenous DNA sequences to enhance the phenotypic expression of the exogenous DNA sequences.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art Reimplantation is accomplished using standard methods. Usually, the surrogate host is anesthetized, and the embryos are inserted into the oviduct. The number of embryos implanted into a particular host will vary by species, but will usually be comparable to the number of off spring the species naturally produces.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout; where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods.

The transgenic animals produced in accordance with the present invention will include exogenous genetic material. As set out above, the exogenous genetic material will, in certain embodiments, be a DNA sequence which results in the production of a TRBP protein (either agonistic or antagonistic), and antisense transcript, or a TRBP mutant. Further, in such embodiments, the sequence will be attached to a transcriptional control element, e.g., a promoter, which preferably allows the expression of the transgene product in a specific type of cell.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) *PNAS* 73:1260–1264). Efficient infection of the blastomeres is obtained by enzymatic treatment to remove the zona pellucida (*Manipulating the Mouse Embryo*, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) *PNAS* 82:6927–6931; Van der Putten et al. (1985) *PNAS* 82:6148–6152). Transfection is easily and efficiently obtained by culturing the blastomeres on a monolayer of virus-producing cells (Van der Putten, supra; Stewart et al. (1987) *EMBO* 6:383–388). Alternatively, infection can be performed at a later stage. Virus or virus-producing cells can be injected into the blastocoele (Jahner et al. (1982) *Nature* 298:623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonal stem cell (ES). ES cells are obtained from pre-implantation embryos cultured in vitro and fused with embryos (Evans et al. (1981) *Nature* 292:154–156; Bradley et al. (1984) Nature 309:255–258; Gossler et al. (1986) *PNAS* 83:9065–9069; and Robertson et al. (1986) *Nature* 322:445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) *Science* 240:1468–1474.

In one embodiment, gene targeting, which is a method of using homologous recombination to modify an animal's genome, can be used to introduce changes into cultured embryonic stem cells. By targeting a TRBP gene of interest in ES cells, these changes can be introduced into the germlines of animals to generate chimeras. The gene targeting procedure is accomplished by introducing into tissue culture cells a DNA targeting construct that includes a segment homologous to a target TRBP locus, and which also includes an intended sequence modification to the TRBP genomic sequence (e.g., insertion, deletion, point mutation). The treated cells are then screened for accurate targeting to identify and isolate those which have been properly targeted.

Gene targeting in embryonic stem cells is in fact a scheme contemplated by the present invention as a means for disrupting a TRBP gene function through the use of a targeting transgene construct designed to undergo homologous recombination with one or more TRBP1 genomic sequences. The targeting construct can be arranged so that, upon recombination with an element of a TRBP gene, a positive selection marker is inserted into (or replaces) coding sequences of the targeted gene. The inserted sequence functionally disrupts the TRBP gene, while also providing a positive selection trait.

Generally, the embryonic stem cells (ES cells ) used to produce the knockout animals will be of the same species as the knockout animal to be generated. Thus for example, mouse embryonic stem cells will usually be used for generation of knockout mice.

Embryonic stem cells are generated and maintained using methods well known to the skilled artisan such as those described by Doetschman et al. (1985) *J. Embryol. Exp. Morphol.* 87:27–45). Any line of ES cells can be used, however, the line chosen is typically selected for the ability of the cells to integrate into and become part of the germ line of a developing embryo so as to create germ line transmission of the knockout construct. Thus, any ES cell line that is believed to have this capability is suitable for use herein. One mouse strain that is typically used for production of ES cells, is the 129J strain. Another ES cell line is murine cell line D3 (American Type Culture Collection, catalog no.

CKL 1934) Still another preferred ES cell line is the WW6 cell line (Ioffe et al. (1995) *PNAS* 92:7357–7361). The cells are cultured and prepared for knockout construct insertion using methods well known to the skilled artisan, such as those set forth by Robertson in: Teratocarcinomas and Embryonic Stem Cells: A Practical Approach, E. J. Robertson, ed. IRL Press, Washington, D.C. [1987]); by Bradley et al. (1986) *Current Topics in Devel. Biol.* 20:357–371); and by Hogan et al. Manipulating the Mouse Embryo: A Laboratory Manual, Cold Spring Harbor Laboratory Press, Cold Spring Harbor, N.Y. [1986]).

Insertion of the knockout construct into the ES cells can be accomplished using a variety of methods well known in the art including for example, electroporation, microinjection, and calcium phosphate treatment. A preferred method of insertion is electroporation.

Each knockout construct to be inserted into the cell must first be in the linear form. Therefore, if the knockout construct has been inserted into a vector (described infra), linearization is accomplished by digesting the DNA with a suitable restriction endonuclease selected to cut only within the vector sequence and not within the knockout construct sequence.

For insertion, the knockout construct is added to the ES cells under appropriate conditions for the insertion method chosen, as is known to the skilled artisan. Where more than one construct is to be introduced into the ES cell, each knockout construct can be introduced simultaneously or one at a time.

If the ES cells are to be electroporated, the ES cells and knockout construct DNA are exposed to an electric pulse using an electroporation machine and following the manufacturer's guidelines for use. After electroporation, the ES cells are typically allowed to recover under suitable incubation conditions. The cells are then screened for the presence of the knockout construct.

Screening can be accomplished using a variety of methods. Where the marker gene is an antibiotic resistance gene, for example, the ES cells may be cultured in the presence of an otherwise lethal concentration of antibiotic. Those ES cells that survive have presumably integrated the knockout construct. If the marker gene is other than an antibiotic resistance gene, a Southern blot of the ES cell genomic DNA can be probed with a sequence of DNA designed to hybridize only to the marker sequence Alternatively, PCR can be used. Finally, if the marker gene is a gene that encodes an enzyme whose activity can be detected (e.g., β-galactosidase), the enzyme substrate can be added to the cells under suitable conditions, and the enzymatic activity can be analyzed. One skilled in the art will be familiar with other useful markers and the means for detecting their presence in a given cell. All such markers are contemplated as being included within the scope of the teaching of this invention.

The knockout construct may integrate into several locations in the ES cell genome, and may integrate into a different location in each ES cell's genome due to the occurrence of random insertion events. The desired location of insertion is in a complementary position to the DNA sequence to be knocked out, e.g., the TRBP coding sequence, transcriptional regulatory sequence, etc. Typically, less than about 1–5% of the ES cells that take up the knockout construct will actually integrate the knockout construct in the desired location. To identify those ES cells with proper integration of the knockout construct, total DNA can be extracted from the ES cells using standard methods. The DNA can then be probed on a Southern blot with a probe or probes designed to hybridize in a specific pattern to genomic DNA digested with particular restriction enzyme(s). Alternatively, or additionally, the genomic DNA can be amplified by PCR with probes specifically designed to amplify DNA fragments of a particular size and sequence (i.e., only those cells containing the knockout construct in the proper position will generate DNA fragments of the proper size).

After suitable ES cells containing the knockout construct in the proper location have been identified, the cells can be inserted into an embryo. Insertion may be accomplished in a variety of ways known to the skilled artisan, however a preferred method is by microinjection. For microinjection, about 10–30 cells are collected into a micropipet and injected into embryos that are at the proper stage of development to permit integration of the foreign ES cell containing the knockout construct into the developing embryo. For instance, as the appended Examples describe, the transformed ES cells can be microinjected into blastocytes.

The suitable stage of development for the embryo used for insertion of ES cells is very species dependent, however for mice it is about 3.5 days. The embryos are obtained by perfusing the uterus of pregnant females. Suitable methods for accomplishing this are known to the skilled artisan, and are set forth by, e.g., Bradley et al. (supra).

While any embryo of the right stage of development is suitable for use, preferred embryos are male. In mice, the preferred embryos also have genes coding for a coat color that is different from the coat color encoded by the ES cell genes. In this way, the offspring can be screened easily for the presence of the knockout construct by looking for mosaic coat color (indicating that the ES cell was incorporated into the developing embryo). Thus, for example, if the ES cell line carries the genes for white fur, the embryo selected will carry genes for black or brown fur.

After the ES cell has been introduced into the embryo, the embryo may be implanted into the uterus of a pseudopregnant foster mother for gestation. While any foster mother may be used, the foster mother is typically selected for her ability to breed and reproduce well, and for her ability to care for the young. Such foster mothers are typically prepared by mating with vasectomized males of the same species. The stage of the pseudopregnant foster mother is important for successful implantation, and it is species dependent. For mice, this stage is about 2–3 days pseudopregnant.

Offspring that are born to the foster mother may be screened initially for mosaic coat color where the coat color selection strategy (as described above, and in the appended examples) has been employed. In addition, or as an alternative, DNA from tail tissue of the offspring may be screened for the presence of the knockout construct using Southern blots and/or PCR as described above. Offspring that appear to be mosaics may then be crossed to each other, if they are believed to carry the knockout construct in their germ line, in order to generate homozygous knockout animals. Homozygotes may be identified by Southern blotting of equivalent amounts of genomic DNA from mice that are the product of this cross, as well as mice that are known heterozygotes and wild type mice.

Other means of identifying and characterizing the knockout offspring are available. For example, Northern blots can be used to probe the mRNA for the presence or absence of transcripts encoding either the gene knocked out, the marker gene, or both. In addition, Western blots can be used to assess the level of expression of the TRBP gene knocked out in various tissues of the offspring by probing the Western blot with an antibody against the particular TRBP protein, or an antibody against the marker gene product, where this gene is expressed. Finally, in situ analysis (such as fixing the cells and labeling with antibody) and/or FACS (fluorescence activated cell sorting) analysis of various cells from the offspring can be conducted using suitable antibodies to look for the presence or absence of the knockout construct gene product.

Yet other methods of making knock-out or disruption transgenic animals are also generally known. See, for example, Manipulating the Mouse Embryo, (Cold Spring Harbor Laboratory Press, Cold Spring Harbor, N.Y., 1986). Recombinase dependent knockouts can also be generated, e.g. by homologous recombination to insert target sequences, such that tissue specific and/or temporal control of inactivation of a TRBP gene can be controlled by recombinase sequences (described infra).

Animals containing more than one knockout construct and/or more than one transgene expression construct are prepared in any of several ways. The preferred manner of preparation is to generate a series of mammals, each containing one of the desired transgenic phenotypes. Such animals are bred together through a series of crosses, backcrosses and selections, to ultimately generate a single animal containing all desired knockout constructs and/or expression constructs, where the animal is otherwise congenic (genetically identical) to the wild type except for the presence of the knockout construct(s) and/or transgene(s).

The present invention is further illustrated by the following examples which should not be construed as limiting in any way. The contents of all cited references (including literature references, issued patents, published patent applications as cited throughout this application are hereby expressly incorporated by reference. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No: 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M Weir and C. C. Blackwell, eds., 1986) *Manipulating the Mouse Embryo*, (Cold Spring Harbor Laboratory Press, Cold Spring Harbor, N.Y., 1986).

5. Examples 5.1 Identification of a Gene Encoding the Human TRBP Protein

This example describes the identification of a gene encoding human TRBP by positional cloning. A cDNA comprising the sequence from about nucleotides 24 to the 3' end of SEQ ID No. 1 has been isolated. The 5' end of the TRBP nucleic acid was determined by sequencing a genomic clone. A high resolution "sequence ready" physical map of the regions of chromosome 12q between markers AfMa82Za5 and AFM165yb12 was created. This region was identified as containing one or more genes involved in type II diabetes, including MODY. The physical map was made by isolating DNA clones that span the genetic interval defined by the markers described above (AFMa82za5 and AFM165yb12).

YAC (yeast artificial chromosomes) maps were constructed using the publicly available markers in the region in an attempt to confirm the order of published YACs and markers. The YAC libraries were screened by PCR amplification of a DNA pool representing the libraries. (A description of the screening protocol can be found in Research Genetics Catalog #95001). Once the YAC map was assembled, a bubble vectorette and interspersing repeat sequence (IRS) were used to both clone the ends of the YACs and generate more markers throughout the region (*Current Protocols in Human Genetics First Edition*, (1994) John Wiley & Co., N. C. Dracopoli et al., eds). Primers were designed from these sequences and used to rescreen the YAC library by PCR to identify adjacent YACs.

In order to further aid in gene identification and to confirm the integrity of the YAC contig and marker order, BACs (bacterial artificial chromosome) and PACs (P1 artificial chromosomes) clones were isolated. The same STSs (sequence tag sites, used for PCR) used to construct the YAC contig were used to screen the Research Genetics human BAC library (Research Genetics, Huntsville, Ala.) and Genome Systems PAC library (Genome Systems) according to manufacturers' suggested screening protocols. Additional STSs were produced by cloning and sequencing the ends of the BAC and/or PACs. Random sequencing of BamHI/BglII restricted libraries of the BACs and PACs was also used to generate more STSs. Creation of over 400 PCR markers enabled the creation of a high resolution sequence ready physical map consisting of a minimal tiling path of 23 BAC and PAC clones with markers spaced approximately every 5 kb. The BAC and PAC that make up the minimal tiling path were sized by pulse gel electrophoresis and range in size from 40 to 230 kb. Sizing all the clones in the interval between the markers AFMa82za5 and GGAT1E2 determined the size of the region to be approximately 2.4 Mb.

The following techniques were employed to identify specific genes in the target region of chromosome 12q: i) sample (shotgun) sequencing; ii) exon trapping; iii) cDNA selection; and iv) transcription mapping. A brief description of each technique is provided below.

Sample (shotgun) sequencing

Random sheared libraries were made from all the BAC and PAC clones within the defined genetic interval by sonicating the DNA. Fragments in the size range of 3–5 kb were cloned into the vector pCDNAII (Invitrogen, San Diego, Calif.). Approximately 4000 subclones were sequenced with vector primers in order to generate 8-fold sequence coverage of each BAC or PAC clone. All sequences were processed through an automated sequence analysis pipeline that assessed quality, removed vector sequences, masked repetitive sequences. The sequences that passed through the automated sequence analysis pipeline were then aligned to public DNA and protein databases using BLAST algorithms (Altschul et al., 1990 J. Mol. Biol. 215:403). Both known and novel genes were identified in the relevant region between markers AFMa82za5 and GGAT1E2 on chromosome 12.

Exon trapping

Exon trapping was carried out by isolating internal exons from individual P1 and BAC clones carrying genomic DNA using the exon trapping vector D-pSPL3 as described in the Gibco BRL Exon Trapping System Instruction Manual (Cat. No. 18449-017). In this system, exons are trapped from genomic DNA subcloned into D-pSPL3 as a result of the interaction between vector splice sites and splice sites flanking exons in the genomic DNA. D-pSPL3 was derived from the splicing vector pSPL3 (Gibco BRL) by deletion of the NdeI (1119)-NheI (1976) fragment in the HIV tat intron to eliminate the cryptic splice-donor site at position 1134 in the pSPL3 sequence.

Briefly, the exon trapping procedure involves: subcloning the P1/Bac clone into D-pSPL3, plating of the resulting D-pSPL3 library and preparation of DNA, transfection of library DNA into COS-7 cells, RNA isolation after transient expression, first strand cDNA synthesis using a vector-specific primer by reverse transcriptase polymerase chain reaction (RT-PCR), cDNA amplification by an initial round of PCR, BstXI digestion of primary PCR products to eliminate vector-vector and cryptic splicing products, secondary amplification with dUMP-containing primers, and cloning of secondary PCR products into the phagemid vector pAMP10 (Gibco BRL) using uracil DNA glycosylase (UDG).

P1/BAC DNA was prepared from overnight cultures (1000 ml LB/kanamycin 25 $\mu$g/ml) by alkaline lysis, treated with RNase A, purified by phenol/chloroform/isoamyl alcohol (25:24:1) extraction, ethanol precipitated, rinsed in 70% ethanol, dried and resuspended in 400 $\mu$l deionized water. 5–10 $\mu$g P1/Bac DNA was cut with either BamHI and BglII, or PstI, as specified by the manufacturer (New England Biolabs). The digested DNA was phenol extracted, ethanol precipitated, and resuspended in 50 $\mu$l deionized water.

Stocks of BamHI-cut and PstI-cut D-pSPL3 DNA were prepared by digesting 50–100 $\mu$g DNA with the corresponding enzyme and dephosphorylating the linearized vector with calf intestine alkaline phosphatase as specified by the manufacturers (New England Biolabs and Boehringer Mannheim, respectively). The linearized vector was purified away from uncut plasmid DNA by agarose gel electrophoresis and electroelution and assayed to assess the level of uncut and self-ligated vector as described elsewhere (Pulido and Duyk, In *Current Protocols in Human Genetics* First Edition, (1994) John Wiley & Co., N. C. Dracopoli et al., eds).

Insert-vector ligation reactions contained 200 ng vector DNA, 20 ng insert DNA, 4 $\mu$l of 5×ligation buffer (Gibco BRL), and 0.6 units of T4 DNA ligase (Gibco BRL) in a total volume of 20 $\mu$l, and were incubated for 1–2 hours at room temperature. 2 $\mu$l of the ligation reaction was transformed into *Escherichia coli* XL-1B cells (New England Biolabs) by electroporation (Bio-Rad Instruction Manual Cat. No. 165-2098). Routinely, 0.1 and 0.01 ml of each transformation was plated on LB/carbenicillin (100 $\mu$g/ml) plates to obtain the library titer. For each library, plasmid DNA from at least 20 single transformants were restriction digested to assess the efficiency of the shotgun subcloning, and sequenced. The sequencing primers were: SPL3A (forward primer; 5'-CAT GCT CCT TGG GAT GT -3'; SEQ ID NO.3 Operon Technologies) and SPL3C (reverse primer; 5'-TGA GGA TTG CTT AAA GA-3'; SEQ ID NO. 4; Operon Technologies).

Each P1/BAC library was plated on three 150-mm LB/carbenicillin plates at a density of 7×10$^3$ colonies/plate (for a total of 2.1×10$^4$ colonies) and grown overnight at 37° C. The colonies were resuspended and pooled in a total of 20 ml LB medium. DNA was prepared from the pooled cell suspension using a Qiagen-tip 500 column as specified by the manufacturer (Qiagen Plasmid Handbook).

Transient transfections of COS-7 cells (American Type Culture Collection) were performed in 3.5-cm 6-well dishes using LipofectACE reagent (Gibco BRL) as described in the Gibco BRL Exon Trapping System Instruction Manual (Cat. No. 18449-017). The cells were passaged one day prior to transfection by placing 4×10$^5$ cells in 2 ml supplemented D-MEM into each well. 1–3 $\mu$g DNA mixed with 5 $\mu$l LipofectACE reagent in 1 ml Opti-MEM medium was added per well. In addition to P1/Bac library DNA, every round of transfections included as controls: D-pSPL3 DNA, the Gibco BRL exon control plasmid, and a "no DNA" transfection. After a 5-hour incubation, the lipid-DNA complexes were removed, and the cells were added 2 ml supplemented D-MEM and incubated for 24 hours.

Total RNA from transiently transfected COS-7 cells was isolated using TRIzol reagent (Gibco BRL) as described in the Gibco BRL Exon Trapping System Instruction Manual (Cat. No. 18449-017).

The reverse transcriptase polymerase chain reaction (RT-PCR) was performed as described in the Gibco BRL Exon Trapping System Instruction Manual (Cat. No. 18449-017) and contained in a total volume of 20 $\mu$l: 3 $\mu$g total RNA, 1 $\mu$l of 20 $\mu$M oligonucleotide SA2 (5'-ATC TCA GTG GTA TTT GTG AGC-3'; SEQ ID NO. 5 [Gibco BRL]), 4 $\mu$l of 5×first strand buffer, 2 $\mu$l of 0.1 M DTT, 1 $\mu$l of 10 mM dNTP mix (10 mM each dATP, dTTP, dCTP, dGTP), 1 $\mu$l of SuperScript II Reverse Transcriptase (Gibco BRL), and DEPC-treated water to a final volume of 20 $\mu$l. Following RT-PCR, the RNA template was degraded by addition of 1 $\mu$l RNase H (Gibco BRL) and incubation for 10 min at 55° C.

The primary PCR reaction contained in a total volume of 40 $\mu$l: 8 $\mu$l of RT-PCR mixture, 2 $\mu$l of 20 $\mu$M oligonucleotide SA2, 2 $\mu$l of 20 $\mu$M oligonucleotide SD6 (5'-TCT GAG TCA CCT GGA CAA CC-3×; SEQ ID NO. 6 [Gibco BRL]), 0.8 $\mu$l of 10 mM dNTP mix, 4 $\mu$l of 10×GeneAmp PCR buffer (Perkin Elmer) and 22.7 $\mu$l deionized water. The mixture was overlaid with 50 $\mu$l mineral oil, placed in a Perkin Elmer Cetus 480 thermal cycler preheated to 94° C., and incubated for 5 minutes. The temperature was reduced to 80° C., and 0.5 $\mu$l (2.5 units) of AmpliTaq DNA polymerase (Perkin Elmer) was added per tube. Six cycles of PCR amplification were performed as follows: 94° C. for 1 minute, 60° C. for 1 minute, and 72° C. for 5 minutes, with a final extension at 72° C. for 10 minutes. 10 $\mu$l of primary PCR reaction was removed (uncut primary PCR) and 2.5 $\mu$l (25 units) of BstXI (Gibco BRL) was added to the remaining reaction which was incubated at 55° C. overnight.

The secondary PCR reaction contained in a total volume of 50 $\mu$l: 5 $\mu$l of BstXI-treated primary PCR product, 1 $\mu$l of 20 $\mu$M secondary amplification primer mix [20 $\mu$M each dUSD2 (5'-CUA CUA CUA CUA GTG AAC TGC ACT GTG ACA AGC TGC-3' SEQ ID NO. 7 [Gibco BRL]) and dUSA4 (5'-CUA CUA CUA CUA CAC CTG AGG AGT GAA TTG GTC G-3'); SEQ ID NO. 8 [Gibco BRL]), 1 $\mu$l of 10 mM dNTP mix, 5 $\mu$l of 10×GeneAmp PCR buffer (Perkin Elmer), and 38 $\mu$l deionized water. The mixture was overlaid with 50 $\mu$l mineral oil, placed in a Perkin Elmer Cetus 480 thermal cycler preheated to 94° C., and incubated for 5 minutes. The temperature was reduced to 80° C., and 0.5 $\mu$l (2.5 units) of AmpliTaq DNA polymerase (Perkin Elmer) was added per tube. 30 cycles of PCR amplification were performed as follows: 94° C. for 1 minute, 60° C. for 1 minute, and 72° C. for 3 minutes, with a final extension at 72° C. for 10 minutes. As a control for the BstXI treatment, uncut primary PCR samples were amplified in parallel as described for BstXI-treated samples. The secondary PCR products were routinely analyzed by agarose gel electrophoresis (2% agarose).

The UDG cloning reaction contained: 6 μl of secondary PCR product, 2 μl of pAMP10 cloning vector (Gibco BRL), 1 μl of 10×GeneAmp PCR buffer (Perkin Elmer), and 1 μl (1 unit) of uracil DNA glycosylase (Gibco BRL). The reaction was incubated at 37° C. for 30 minutes. 2 μl of the reaction was transformed into DH11S cells (Gibco BRL) by electroporation (Bio-Rad). Transformants were selected on LB/carbenicillin plates and evaluated by colony PCR- The colony PCR reaction contained in 25 μl total volume: colony resuspended in 10 μl deionized water, 0.5 μl of 20 μM secondary amplification primer mix (see above), 0.5 μl of 10 mM dNTP mix, 2.5 μl of 10×GeneAmp PCR buffer (Perkin Elmer), 0.25 μl (1.25 units) AmpliTaq DNA Polymerase (Perkin Elmer), and 11.3 μl deionized water. PCR reactions were performed in the Perkin-Elmer Cetus GeneAmp PCR System 9600. The amplification parameters were: 94° C, for 5 min, followed by 30 cycles of: 94° C. for 45 seconds, 55° C. for 30 seconds, and 72° C. for 1 minute, with a final extension at 72° C. for 10 minutes. The colony PCR products were analyzed in 2% agarose gels. Clones with insert sizes greater than 177 bp were sequenced using M13 forward and reverse primers.

cDNA selection cDNA selection or screening of arrayed genomic fragments was designed for isolating genes with diverse expression patterns from large genomic regions. Clones that make up the minimal tiling path of the critical region were hybridized with cDNA probes quantitatively depleted of repetitive sequences. cDNA probes were synthesized from the following human tissues: adult and fetal brain, adult and fetal liver, fibroblast, Cacao cells (immortalized colon cancer cells), skeletal muscle, placenta, testis, pancreas, pancreatic islets, Jurkat cells (a lymphoblas cell line) and prostate. The cDNA selection technique was carried out as described in Current Protocols in Human Genetics, N. Dracopoli et al., eds.. Briefly, the radiolabeled cDNA probe was made by synthesizing first-strand cDNA by reverse transcription of mRNA isolated from the tissues described above. The first strand cDNA is used as a template to produce radiolabeled second-strand cDNA by random hexamer-primed synthesis. Highly repetitive sequences were removed from the radiolabeled probe by hybridization with DNA cellulose. Filters containing the BAC and PAC clones of the minimal tiling path were hybridized with the radiolabeled cDNA probes. The cDNA fragments that hybridized specifically were then cloned into the vector pAMP10 (Life Technologies, Gaithersburg, Md.) with the enzyme uracil DNA glycosylase as described by the manufacturer (Life Technologies, Gaithersburg, Md.). Approximately 3000 clones were sequenced. These clones fell into 470 "bins"—meaning that they were part of the same gene. Out of these 470 bins, 131 were shown to overlap to genomic clones in the critical region by PCR with primers specific for the cDNA fragment selected. These clones were also confirmed to be transcripts by RT-PCR on tissues from which they arose. Another 134 bins require confirmation. Still another 205 sequences were not followed, because they were shown to contain either repetitive sequences and/or made up of only polyA tracks.

The combination of sample sequencing, exon-trapping and cDNA selection allowed the identification of over 100 transcripts. A cDNA corresponding to one of these transcripts has been isolated and is specifically claimed herein. The cDNA is about 1733 base pairs long and has the nucleotide sequence from about nucleotide 24 to the end of SEQ ID No.1 shown in FIG. 1. The s' end of SEQ ID No. 1 was determined by sequencing of the genomic cDNA As shown in FIG. 1, the nucleic acid sequence SEQ ID No. 1 has an open reading frame from nucleotide 1 to nucleotide 1542, thus encoding a potential protein of 514 amino acids (SEQ ID No. 2).

A comparison of the nucleotide sequence SEQ ID No. 1 and the amino acid sequence SEQ ID No. 2 with nucleic acids and proteins against databases using Blastx revealed that two ESTs have sequence similarity with SEQ ID No. 1. One EST, having GenBank Accession No. F06909, is similar to the sequence from nucleotide 574 to nucleotide 877 of SEQ ID No. 1. EST F06909 is a 301 nucleotide long human DNA isolated from normalized infant brain cells in the Genexpress cDNA program. This sequence differs from the corresponding sequence in SEQ ID No. 2 in 16 nucleotides and are either nucleotide substitutions or deletions. Accordingly, there is 95% identity between the nucleotide sequence of F06909 and the nucleotide sequence from nucleotides 574 to 877 of SEQ ID No. 1. The second EST, having GenBank Accession No. AA115315, is similar to the sequence from nucleotide 1124 to nucleotide 1641 of SEQ ID NO. 1. EST AA115315 is a 514 nucleotide long human cDNA clone isolated from a colonic epithelial cell line in the WashU-Merck EST project. This nucleic acid differs from the corresponding region in SEQ ID No. 1 in 9 nucleotides: nucleotides 1134, 1433 and 1462, which are all located in a coding region of TRBP, are missing in the EST clone. The other 6 nucleotide differences are nucleotide substitutions or additions in the 3' untranslated regions of SEQ ID No. 1. Accordingly, there is 98% identity between the nucleotide sequence of AA115315 and the sequence from nucleotides 1124 to 1641 of SEQ ID No. 1.

The Blastx (Altschul et al. (1990) J. Mol. Biol. 215:403) search also showed that a portion of the isolated cDNA and putative protein encoded by the cDNA have a substantially similar homology to a 470 nucleotide long nucleic acid encoding a partial human protein termed "TRIP14", having GenBank Accession No. L40387. In the cDNA, the region of homology between SEQ ID No. 1 and the TRIP 14 nucleotide sequence corresponds to a sequence from about nucleotide 778 to about nucleotide 1248 of SEQ ID No. 1. An alignment of the two nucleotide sequences is shown in FIG. 2, which shows that the two nucleic acid sequences differ at 8 nucleotides. Accordingly, TRIP 14 nucleic acid has 98% identity with the sequence from nucleotides 778 to 1248 set forth in SEQ ID No. 1. At the protein level, the region of similarity between SEQ ID No. 2 and TRIP14 corresponds to the sequence from amino acid 260 to amino acid 416 of SEQ ID No. 2. An alignment of the amino acid sequence SEQ ID No. 2 and the amino acid sequence of TRIP14 is shown in FIG. 3. This alignment indicates that amino acids 260 to amino acid 381 of SEQ ID No. 2 differs from the amino acid sequence of TRIP14 in for 2 amino acids which are located at positions 335 and 336. As shown in FIG. 3, the $NH_2$terminus of TRIP 14 is only distantly related to SEQ ID No. 2, due to a frameshift difference between the two nucleic acid sequences.

The nucleic acid encoding the partial protein termed TRIP14 (Thyroid hormone receptor Interacting Protein 14) was isolated from a HeLa derived cDNA library using the yeast-two hybrid system called interaction trap to isolate proteins that interact with the complex ligand binding/ dimerization/transcriptional activation domain of the rat thyroid hormone receptor β1(TRβ1) (Lee et al. (1995) Endocrinology 9:243–254). Interestingly, TRIP14 interacts with the thyroid hormone receptor in the presence of thyroid hormone ($T_3$), but not in the absence of thyroid hormone. Contrary to most other TRIPs, no interaction between TRIP14 and the Retinoid X Receptor (RXR) was detectable in binding experiments. Thus, it is likely that the isolated cDNA encodes a protein from the same family as TRIP14. Accordingly, the protein encoded by the gene having SEQ ID No. 1 is referred to herein as TRBP protein.

Furthermore, a portion of the amino acid sequence SEQ ID No. 2 has a certain similarity to the 2'-5' oligoA synthase. A sequence alignment of SEQ ID No. 2 and the 2'-5' oligoA synthase (GenBank Accession No. D00068) is shown in FIG. 5. The 2'-5' oligoA synthase is a protein which is induced in response to interferon and which catalyzes 5 the formation of 2'-5' oligoadenylates which activate RNase L. Since the 2'-5' oligoA synthase comprises an ATP-binding domain and a double stranded RNA-binding domain, TRBP may also bind ATP and double stranded RNA.

The TRBP protein has also a weak homology to ubiquitin protein (Gen Bank Accession No. U49869) and could thus have at least some of the activities of ubiquitin proteins.

5.2 Determination of the intron/exon boundaries

Comparison of genomic nucleic acid sequences with cDNA sequences 4: indicated that the human TRBP gene comprises at least 6 introns. The, location of the 15 introns, and a portion of the nucleic acid sequences of some of the introns is shown in FIG. 4.

5.3 Expression of Recombinant TRBP in COS Cells

This example describes a method for producing recombinant full length human TRBP in mammalian expression system.

An expression construct containing a nucleic acid encoding a full length human TRBP protein can be constructed as follows. A nucleic acid encoding the full length human TRBP protein is obtained by reverse transcription (RT-) PCR of mRNA extracted from HeLa cells or other cell expressing TRBP using PCR primers based on the sequence set forth in SEQ ID No. 1. The PCR primers further contain appropriate restriction sites for introduction into the expression plasmid. The amplified nucleic acid is then inserted in a eukaryotic expression plasmid such as pcDNAI/Amp (Invitrogen) containing: 1) SV40 origin of replication, 2) ampicillin resistance gens, 3) *E. coli* replication origin, 4) CMV promoter followed by a polylinker region, a SV40 intron and polyadenylation site. A DNA fragment encoding the full length human TRBP and a HA or myc tag fused in frame to its 3' end is then cloned into the polylinker region. The HA tag correspond to an epitope derived from the influenza hemagglutinin protein as previously described (I. Wilson, H. Niman, R. Heighten, A Cherenson, M. Connolly, and R. Lerner, 1984, Cell 37, 767).

For expression of the recombinant TRBP, COS cells are transfected with the expression vector by DEAE-DEXTRAN method. (J. Sambrook, E. Fritsch, T. Maniatis, Molecular Cloning: A Laboratory Manual, Cold Spring Laboratory Press, (1989)). The expression of the TRBP -HA protein can be detected by radiolabelling and immunoprecipitation method. (E. Harlow, D. Lane, Antibodies: A Laboratory Manual, Cold Spring Harbor Laboratory Press, (1988)). For this, transfected cells are labelled for 8 hours with 35S-cysteine two days post transfection. Culture media is then collected and cells are lysed with detergent (RIPA buffer (150 mM NaCI 1% NP-40, 0.1% SDS, 1% NP-40, 0.5% DOC, 50 mM Tris, pH 7.5). (Wilson, I. et al., Id. 37:767 (1984)). Both cell lysate and culture media are precipitated with an HA specific monoclonal antibody. Proteins precipitated are analyzed on SDS-PAGE gels.

Equivalents

Those skilled in the art will recognize, or be able to ascertain using no more than routine experimentation, many equivalents of the specific embodiments of the invention described herein. Such equivalents are intended to be encompassed by the following claims.

I claim:

1. An isolated nucleic acid molecule that encodes an amino acid sequence comprising SEQ ID NO: 2.

2. An isolated nucleic acid molecule that encodes an amino acid sequence consisting of SEQ ID NO: 2.

3. An isolated nucleic acid molecule that is comprised of at least 500 nucleotides and specifically hybridizes at a stringency of 0.2×sodium chloride sodium citrate (SSC) at 50° C., followed by a wash of 2.0×SSC at 50° C. to SEQ ID NO: 1.

4. The isolated nucleic acid molecule of claim 1, wherein said nucleic acid molecule comprises the nucleotide sequence of SEQ ID NO: 1.

5. The isolated nucleic acid molecule of claim 1, wherein said nucleic acid molecule consists of the nucleotide sequence of SEQ ID NO: 1.

6. The isolated nucleic acid molecule of claim 2, wherein said nucleic acid molecule consists of the nucleotide sequence of SEQ ID NO: 1.

7. A vector comprising the nucleic acid molecule of claim 1.

8. A vector comprising the nucleic acid molecule of claim 2.

9. A vector comprising the nucleic acid molecule of claim 4.

10. A vector comprising the nucleic acid molecule of claim 5.

11. A vector comprising the nucleic acid molecule of claim 6.

12. A host cell comprising the vector of claim 7.

13. A host cell comprising the vector of claim 8.

14. A host cell comprising the vector of claim 9.

15. A host cell comprising the vector of claim 10.

16. A host cell comprising the vector of claim 11.

* * * * *